(12) United States Patent
Boyne et al.

(10) Patent No.: US 12,365,733 B2
(45) Date of Patent: Jul. 22, 2025

(54) METHOD FOR IMPROVING PRODUCTION OF CAR T CELLS

(71) Applicant: CELLECTIS, Paris (FR)

(72) Inventors: Alex Boyne, Jersey City, NJ (US); Laurent Poirot, Paris (FR); Philippe Duchateau, Draveil (FR); Alexandre Juillerat, New York, NY (US)

(73) Assignee: Cellectis, Paris (FR)

( * ) Notice: Subject to any disclaimer, the term of this patent is extended or adjusted under 35 U.S.C. 154(b) by 994 days.

(21) Appl. No.: 16/958,250

(22) PCT Filed: Dec. 28, 2018

(86) PCT No.: PCT/EP2018/097080
§ 371 (c)(1),
(2) Date: Jun. 26, 2020

(87) PCT Pub. No.: WO2019/129851
PCT Pub. Date: Jul. 4, 2019

(65) Prior Publication Data
US 2020/0332004 A1    Oct. 22, 2020

Related U.S. Application Data

(60) Provisional application No. 62/611,987, filed on Dec. 29, 2017.

(30) Foreign Application Priority Data

Jan. 10, 2018    (DK) .................................. 201870015

(51) Int. Cl.
| | | |
|---|---|---|
| C07K 16/28 | (2006.01) |
| A61K 40/11 | (2025.01) |
| A61K 40/22 | (2025.01) |
| A61K 40/31 | (2025.01) |
| A61K 40/41 | (2025.01) |
| A61K 40/42 | (2025.01) |
| A61K 40/50 | (2025.01) |
| A61P 35/00 | (2006.01) |
| C12N 5/0783 | (2010.01) |
| C12N 15/86 | (2006.01) |
| C12N 15/87 | (2006.01) |

(52) U.S. Cl.
CPC .......... *C07K 16/2809* (2013.01); *A61K 40/11* (2025.01); *A61K 40/22* (2025.01); *A61K 40/31* (2025.01); *A61K 40/418* (2025.01); *A61K 40/4202* (2025.01); *A61K 40/421* (2025.01); *A61K 40/4212* (2025.01); *A61P 35/00* (2018.01); *C07K 16/2815* (2013.01); *C07K 16/2878* (2013.01); *C12N 5/0636* (2013.01); *C12N 15/86* (2013.01); *C12N 15/87* (2013.01); *A61K 40/50* (2025.01); *A61K 2239/31* (2023.05); *A61K 2239/38* (2023.05); *A61K 2239/48* (2023.05); *C07K 2317/622* (2013.01); *C07K 2319/03* (2013.01); *C07K 2319/60* (2013.01); *C12N 2510/00* (2013.01); *C12N 2750/14143* (2013.01)

(58) Field of Classification Search
CPC ........ A61K 35/17; A61K 40/11; A61K 40/22; A61K 40/31; A61K 40/418; A61K 40/4202; A61K 40/421; A61K 40/4212; A61K 40/50; A61K 2239/31; A61K 2239/38; A61K 2239/48; C07K 16/2809; C07K 16/2815; C07K 16/2878; C07K 2317/622; C07K 2319/03; C07K 2319/60; A61P 35/00; C12N 5/0636; C12N 15/86; C12N 15/87; C12N 2510/00; C12N 2750/14143

See application file for complete search history.

(56) References Cited

FOREIGN PATENT DOCUMENTS

| | | |
|---|---|---|
| WO | WO 2015/132598 | 9/2015 |
| WO | WO 2016/069282 | 5/2016 |
| WO | WO 2016/126213 | 8/2016 |
| WO | WO 2018/115906 | 6/2018 |
| WO | WO-2019129851 A1 * | 7/2019 ............. A61K 35/17 |

OTHER PUBLICATIONS

Rasaiyaah et al. (JCI. Insight. Jul. 12, 2018; 3 (13): e99442; pp. 1-14).*
Harrer et al. (BMC Cancer. Aug. 17, 2017; 17 (1): 551; pp. 1-17).*
Beatty et al. (Cancer Immunol. Res. Feb. 2014; 2 (2): 112-20).*
Beatty et al. (Gastroenterology. Jul. 2018; 155 (1): 29-32).*
Zah et al. (Cancer Immunol. Res. Jun. 2016; 4 (6): 498-508).*
Mamonkin et al. (Blood. Aug. 20, 2015; 126 (8): 983-92; printer-friendly copy; pp. 1-19).*
Gu et al. (Int. J. Mol. Sci. Nov. 2018; 19 (11): 3455; pp. 1-12).*
Eyquem et al. (Nature. Mar. 2, 2017; 543 (7643): 113-117).*
Poirot et al. (Cancer Res. Sep. 15, 2015; 75 (18): 3853-64).*
Stone et al. (Front. Immunol. Aug. 21, 2013; 4: 244; pp. 1-16).*
Echchannaoui et al. (Mol. Ther. Jan. 2, 2019; 27 (1): 261-71).*

(Continued)

*Primary Examiner* — Janet L Epps -Smith
*Assistant Examiner* — Carol Ann Chase
(74) *Attorney, Agent, or Firm* — Casimir Jones, S.C.; Peter J. Schlueter

(57) ABSTRACT

A method for engineering less alloreactive immune cells, including T-cells that express chimeric antigen receptors (CARs), using a nucleotide sequence in form of an RNA encoding a anti-TCR CAR to achieve the transient expression of anti-TCR CAR at the cell surface. The transient expression of the anti-TCR CAR recognized by the alpha beta TCR on the cell surface unexpectedly enabled the a purification of the TCR-negative CAR expressing cells. The TCR-negative CAR expressing immune cells can be used in adoptive therapy to treat diseases associated with cell surface antigens, such as cancer with less side effects, in particular less GVHD.

12 Claims, 7 Drawing Sheets

Specification includes a Sequence Listing.

(56) References Cited

OTHER PUBLICATIONS

Walseng et al. (Sci. Rep. Sep. 6, 2017; 7 (1): 10713; pp. 1-10).*
Pulford et al. (Blood. Feb. 1, 1995; 85 (3): 675-84).*
Wang et al. (Nucleic Acids Res. Feb. 18, 2016; 44 (3): e30; pp. 1-9).*
Sanber et al. (Br. J. Haematol. Dec. 2021; 195 (5): 660-668).*
Ghosh et al. (Nat. Med. Feb. 2017; 23 (2): 242-249; author manuscript; pp. 1-20).*
Cooper et al. (Leukemia. Sep. 2018; 32 (9): 1970-83; author manuscript; pp. 1-23).*
Valton et al. (Mol. Ther. Sep. 2015; 23 (9): 1507-18).*
International Search Report and Written Opinion for PCT/EP2018/097080. Mailed Apr. 8, 2019. 10 pages.
Qasim et al., Molecular remission of infant B-ALL after infusion of universal TALEN gene-edited CAR T cells. Sci Transl Med. Jan. 25, 2017; 9(374):eaaj2013. 9 pages.

* cited by examiner

A

B

SEQUENCE LISTING

```
<160> NUMBER OF SEQ ID NOS: 22

<210> SEQ ID NO 1
<211> LENGTH: 63
<212> TYPE: DNA
<213> ORGANISM: artificial sequence
<220> FEATURE:
<223> OTHER INFORMATION: CD8 signal seq

<400> SEQUENCE: 1
atggctttgc ctgtcactgc cttgctgctt ccacttgctc tgttgttgca cgccgcaaga    60
ccc                                                                  63

<210> SEQ ID NO 2
<211> LENGTH: 723
<212> TYPE: DNA
<213> ORGANISM: artificial sequence
<220> FEATURE:
<223> OTHER INFORMATION: anti-CD3 scFv

<400> SEQUENCE: 2
gatattcaga tgacccagtc cccctcctcc ctgtccgctt ccgtcggcga tagagtcacc    60
attacctgtt cagccagtag ttccgtgtct tacatgaact ggtatcagca gaccccaggc   120
aaggcaccta agcggtggat ctacgacaca tccaagctgg cctctggagt gcccagccgg   180
ttctccggct ctggcagcgg caccgactat acctttacaa tcagctccct gcagcctgag   240
gacatcgcca catactattg ccagcagtgg tctagcaatc cattcacctt tggccaggga   300
acaaagctgc agatcggagg aggaggcagc ggcggaggag gctccggcgg cggcggctct   360
caggtgcagc tggtgcagtc cggaggagga gtggtgcagc ccggcagaag cctgcggctg   420
agctgtaagg ccagcggcta caccttcaca cggtatacca tgcactgggt gagacaggca   480
ccaggcaagg gcctggagtg gatcggctac atcaacccca gcagaggcta cacaaactat   540
aatcagaagg tgaaggacag gttcaccatc tcccgcgata ctctaagaa tacagccttt   600 ctgcagatgg actccctgag gcctgaggat accgccgtgt atttttgcgc ccgctattat   660
gatgaccatt actgtctgga ctattggggg cagggaacac ccgtgactgt gagctcggat   720
ccc                                                                  723

<210> SEQ ID NO 3
```

<211> LENGTH: 135
<212> TYPE: DNA
<213> ORGANISM: artificial sequence
<220> FEATURE:
<223> OTHER INFORMATION: CD8 hinge

<400> SEQUENCE: 3

```
accacaaccc cgctccaag gcccctacc cccgcaccaa ctattgcctc ccagccactc    60
tcactgcggc ctgaggcctg tcggcccgct gctggaggcg cagtgcatac aaggggcctc   120
gatttcgcct gcgat                                                   135
```

<210> SEQ ID NO 4
<211> LENGTH: 72
<212> TYPE: DNA
<213> ORGANISM: artificial sequence
<220> FEATURE:
<223> OTHER INFORMATION: CD8 trans

<400> SEQUENCE: 4

```
atttacatct gggcacccct cgccggcacc tgcggggtgc ttctcctctc cctggtgatt    60
accctgtatt gc                                                       72
```

<210> SEQ ID NO 5
<211> LENGTH: 465
<212> TYPE: DNA
<213> ORGANISM: artificial sequence
<220> FEATURE:
<223> OTHER INFORMATION: 41BB-CD3z

<400> SEQUENCE: 5

```
agacggggcc ggaagaagct cctctacatt tttaagcagc ctttcatgcg gccagtgcag    60
acaacccaag aggaggatgg gtgttcctgc agattccctg aggaagagga aggcgggtgc   120
gagctgagag tgaagttctc caggagcgca gatgccccccg cctatcaaca gggccagaac   180
cagctctaca cgagcttaa cctcggggag cgcgaagaat acgacgtgtt ggataagaga   240
aggggggcggg accccgagat gggaggaaag ccccggagga agaaccctca ggagggcctg   300
tacaacgagc tgcagaagga taagatggcc gaggcctact cagagatcgg gatgaagggg   360
gagcggcgcc gcgggaaggg gcacgatggg ctctaccagg ggctgagcac agccacaaag   420
gacacatacg acgccttgca catgcaggcc cttccacccc gggaa                   465
```

<210> SEQ ID NO 6
<211> LENGTH: 75
<212> TYPE: DNA
<213> ORGANISM: artificial sequence
<220> FEATURE:
<223> OTHER INFORMATION: 2A

<400> SEQUENCE: 6

```
tcccatggag gaagcggaga gggacgagga agcctgctga cctgcgggga cgtggaggaa    60
aacccaggac ctcat                                                    75
```

<210> SEQ ID NO 7
<211> LENGTH: 702
<212> TYPE: DNA
<213> ORGANISM: artificial sequence
<220> FEATURE:
<223> OTHER INFORMATION: BFP

<400> SEQUENCE: 7

```
atgatgagcg agctgattaa ggagaacatg cacatgaagc tgtacatgga gggcaccgtg    60
```

```
gacaaccatc acttcaagtg cacatccgag ggcgaaggca agccctacga gggcacccag      120
accatgagaa tcaaggtggt cgagggcggc cctctcccct tcgccttcga catcctggct      180
actagcttcc tctacggcag caagaccttc atcaaccaca cccagggcat ccccgacttc      240
ttcaagcagt ccttccctga gggcttcaca tgggagagag tcaccacata cgaggacggg      300
ggcgtgctga ccgctaccca ggacaccagc ctccaggacg ctgcctcat ctacaacgtc      360 aagatcagag gggtgaactt cacatccaac ggccctgtga tgcagaagaa aacactcggc      420
tgggaggcct tcaccgagac gctgtacccc gctgacggcg gcctggaagg cagaaacgac      480
atggccctga agtcgtgggg cgggagccat ctgatcgcaa acatcaagac acatataga      540 tccaagaaac ccgctaagaa cctcaagatg cctggcgtct actatgtgga ctacagactg      600
gaaagaatca aggaggccaa caacgagacc tacgtcgagc agcacgaggt ggcagtggcc      660
agatactgcg acctccctag caaactgggg cacaagctga at                       702

<210> SEQ ID NO 8
<211> LENGTH: 2235
<212> TYPE: DNA
<213> ORGANISM: artificial sequence
<220> FEATURE:
<223> OTHER INFORMATION: 30527

<400> SEQUENCE: 8
atggctttgc ctgtcactgc cttgctgctt ccacttgctc tgttgttgca cgccgcaaga      60
cccgatattc agatgaccca gtccccctcc tccctgtccg cttccgtcgg cgatagagtc      120
accattacct gttcagccag tagttccgtg tcttacatga actggtatca gcagacccca      180
ggcaaggcac ctaagcggtg gatctacgac acatccaagc tggcctctgg agtgcccagc      240
cggttctccg gctctggcag cggcaccgac tatacctta caatcagctc cctgcagcct      300
gaggacatcg ccacatacta ttgccagcag tggtctagca atccattcac ctttggccag      360
ggaacaaagc tgcagatcgg aggaggaggc agcggcggag gaggctccgg cggcggcggc      420
tctcaggtgc agctggtgca gtccggagga ggagtggtgc agcccggcag aagcctgcgg      480
ctgagctgta aggccagcgg ctacaccttc acacggtata ccatgcactg ggtgagacag      540
gcaccaggca agggcctgga gtggatcggc tacatcaacc ccagcagagg ctacacaaac      600
tataatcaga aggtgaagga caggttcacc atctcccgcg ataactctaa gaatacagcc      660
tttctgcaga tggactccct gaggcctgag gataccggcg tgtatttttg cgcccgctat      720
tatgatgacc attactgtct ggactattgg ggcagggaa cacccgtgac tgtgagctcg      780
gatcccacca caacccccgc tccaaggccc ctaccccg caccaactat gcctcccag      840 ccactctcac tgcggcctga ggctgtcggg cccgctgctg gaggcgcagt gcatacaagg      900
ggcctcgatt tcgcctgcga tatttacatc tgggcacccc tcgccggcac ctgcggggtg      960 cttctccctct ccctggtgat taccctgtat tgcagacggg ccggaagaa gctcctctac      1020 attttaagc agcctttcat gcggccagtg cagacaaccc aagaggagga tggtgttcc      1080 tgcagattcc ctgaggaaga ggaaggcggg tgcgagctga gagtgaagtt ctccaggagc      1140
gcagatgccc ccgcctatca acagggccag aaccagctct acaacgagct taacctcggg      1200
aggcgcgaag aatacgacgt gttggataag agaaggggc gggaccccga gatggggagga      1260 aagccccgga ggaagaaccc tcaggagggc ctgtacaacg agctgcagaa ggataagatg      1320
gccgaggcct actcagagat cgggatgaag ggggagcggc gccgcgggaa ggggcacgat      1380
```

```
gggctctacc aggggctgag cacagccaca aaggacacat acgacgcctt gcacatgcag    1440
gcccttccac cccgggaatc ccatggagga agcggagagg gacgaggaag cctgctgacc    1500
tgcggggacg tggaggaaaa cccaggacct catatgatga gcgagctgat taaggagaac    1560
atgcacatga agctgtacat ggagggcacc gtggacaacc atcacttcaa gtgcacatcc    1620
gagggcgaag gcaagcccta cgagggcacc cagaccatga gaatcaaggt ggtcgagggc    1680
ggccctctcc ccttcgcctt cgacatcctg gctactagct tcctctacgg cagcaagacc    1740
ttcatcaacc acacccaggg catccccgac ttcttcaagc agtccttccc tgagggcttc    1800
acatgggaga gagtcaccac atacgaggac ggggggcgtgc tgaccgctac ccaggacacc    1860
agcctccagg acggctgcct catctacaac gtcaagatca gaggggtgaa cttcacatcc    1920
aacggccctg tgatgcagaa gaaaacactc ggctgggagg ccttcaccga cgcgctgtac    1980
cccgctgacg gcggcctgga aggcagaaac gacatggccc tgaagctcgt gggcgggagc    2040
catctgatcg caaacatcaa gaccacatat agatccaaga aacccgctaa gaacctcaag    2100
atgcctggcg tctactatgt ggactacaga ctggaaagaa tcaaggaggc caacaacgag    2160
acctacgtcg agcagcacga ggtggcagtg ccagatact gcgacctccc tagcaaactg    2220
gggcacaagc tgaat                                                    2235

<210> SEQ ID NO 9
<211> LENGTH: 17
<212> TYPE: DNA
<213> ORGANISM: artificial sequence
<220> FEATURE:
<223> OTHER INFORMATION: T7 promoter

<400> SEQUENCE: 9
taatacgact cactata                                                  17

<210> SEQ ID NO 10
<211> LENGTH: 93
<212> TYPE: DNA
<213> ORGANISM: artificial sequence
<220> FEATURE:
<223> OTHER INFORMATION: mouse hba 3UTR

<400> SEQUENCE: 10
gctgccttct gcggggcttg ccttctggcc atgcccttct tctctcccctt gcacctgtac    60 ctcttggtct ttgaataaag cctgagtagg aag                                93

<210> SEQ ID NO 11
<211> LENGTH: 125
<212> TYPE: DNA
<213> ORGANISM: artificial sequence
<220> FEATURE:
<223> OTHER INFORMATION: 120A polyA

<400> SEQUENCE: 11
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa    120
aaaaa                                                               125

<210> SEQ ID NO 12
<211> LENGTH: 2527
<212> TYPE: DNA
<213> ORGANISM: artificial sequence
<220> FEATURE:
<223> OTHER INFORMATION: 30697
```

<400> SEQUENCE: 12

```
taatacgact cactataggc tagcgccgcc accatggctt tgcctgtcac tgccttgctg      60
cttccacttg ctctgttgtt gcacgccgca agacccgata ttcagatgac ccagtccccc     120
tcctccctgt ccgcttccgt cggcgataga gtcaccatta cctgttcagc cagtagttcc     180
gtgtcttaca tgaactggta tcagcagacc ccaggcaagg cacctaagcg gtggatctac     240
gacacatcca agctggcctc tggagtgccc agccggttct ccggctctgg cagcggcacc     300
gactatacct ttacaatcag ctccctgcag cctgaggaca tcgccacata ctattgccag     360
cagtggtcta gcaatccatt cacctttggc cagggaacaa agctgcagat cggaggagga     420
ggcagcggcg aggaggctc cggcggcggc ggctctcagg tgcagctggt gcagtccgga     480
ggaggagtgg tgcagcccgg cagaagcctg cggctgagct gtaaggccag cggctacacc     540
ttcacacggt ataccatgca ctgggtgaga caggcaccag gcaagggcct ggagtggatc     600
ggctacatca accccagcag aggctacaca aactataatc agaaggtgaa ggacaggttc     660
accatctccc gcgataactc taagaataca gcctttctgc agatggactc cctgaggcct     720
gaggataccg cgtgtatttt tgcgcccgc tattatgatg accattactg tctggactat     780
tgggggcagg gaacacccgt gactgtgagc tcggatccca ccacaacccc cgctccaagg     840
ccccctaccc ccgcaccaac tattgcctcc cagccactct cactgcggcc tgaggcctgt     900
cggcccgctg ctggaggcgc agtgcataca aggggcctcg atttcgcctg cgatatttac     960
atctgggcac ccctcgccgg cacctgcggg gtgcttctcc tctccctggt gattaccctg    1020
tattgcagac ggggccggaa gaagctcctc tacattttta gcagcctttt catgcggcca    1080
gtgcagacaa cccaagagga ggatgggtgt cctgcagat tccctgagga agaggaaggc    1140
gggtgcgagc tgagagtgaa gttctccagg agcgcagatg cccccgccta tcaacagggc    1200
cagaaccagc tctacaacga gcttaacctc gggaggcgcg aagaatacga cgtgttggat    1260
aagagaaggg ggcgggaccc cgagatggga ggaaagcccc ggaggaagaa ccctcaggag    1320
ggcctgtaca cgagctgca gaaggataag atggccgagg cctactcaga gatcgggatg    1380
aagggggagc ggcgccgcgg gaaggggcac gatgggctct accaggggct gagcacagcc    1440
acaaaggaca catacgacgc cttgcacatg caggcccttc caccccggga atcccatgga    1500
ggaagcggag agggacgagg aagcctgctg acctgcgggg acgtggagga aaacccagga    1560
cctcatatga tgagcgagct gattaaggag aacatgcaca tgaagctgta catggagggc    1620
accgtggaca accatcactt caagtgcaca tccgagggcg aaggcaagcc ctacgagggc    1680
acccagacca tgagaatcaa ggtggtcgag ggcggccctc tccccttcgc cttcgacatc    1740
ctggctacta gcttcctcta cggcagcaag accttcatca accacaccca gggcatcccc    1800
gacttcttca gcagtccctt ccctgagggc ttcacatggg agagagtcac cacatacgag    1860
gacgggggcg tgctgaccgc tacccaggac accagcctcc aggacggctg cctcatctac    1920
aacgtcaaga tcagaggggt gaacttcaca tccaacggcc ctgtgatgca aagaaaaca    1980
ctcggctggg aggccttcac cgagacgctg taccccgctg acggcggcct ggaaggcaga    2040
aacgacatgg ccctgaagct cgtgggcggg agccatctga tcgcaaacat caagaccaca    2100
tatagatcca agaaacccgc taagaacctc aagatgcctg gcgtctacta tgtggactac    2160
agactggaaa gaatcaagga ggccaacaac gagacctacg tcgagcagca cgaggtggca    2220
gtggccagat actgcgacct ccctagcaaa ctggggcaca agctgaattg acggccgact    2280
```

```
gataactcga ggctgccttc tgcggggctt gccttctggc catgcccttc ttctctccct    2340
tgcacctgta cctcttggtc tttgaataaa gcctgagtag gaaggtcgag gcggccaaca    2400
acaaaaaaaa aaaaaaaaaa aaaaaaaaaa aaaaaaaaaa aaaaaaaaaa aaaaaaaaaa    2460
aaaaaaaaaa aaaaaaaaaa aaaaaaaaaa aaaaaaaaaa aaaaaaaaaa aaaaaaaaaa    2520
aaaaaaa                                                               2527

<210> SEQ ID NO 13
<211> LENGTH: 56
<212> TYPE: DNA
<213> ORGANISM: artificial sequence
<220> FEATURE:
<223> OTHER INFORMATION: oligo1

<400> SEQUENCE: 13
gcatcgtaat acgactcact atagggcagg ccaccatggc tttgcctgtc actgcc        56

<210> SEQ ID NO 14
<211> LENGTH: 21
<212> TYPE: DNA
<213> ORGANISM: artificial sequence
<220> FEATURE:
<223> OTHER INFORMATION: oligo2

<400> SEQUENCE: 14
tcaattcagc ttgtgcccca g                                               21

<210> SEQ ID NO 15
<211> LENGTH: 21
<212> TYPE: PRT
<213> ORGANISM: artificial sequence
<220> FEATURE:
<223> OTHER INFORMATION: CD8 signal seq

<400> SEQUENCE: 15
```

Met Ala Leu Pro Val Thr Ala Leu Leu Leu Pro Leu Ala Leu Leu
1               5                   10                  15

His Ala Ala Arg Pro
            20

```
<210> SEQ ID NO 16
<211> LENGTH: 241
<212> TYPE: PRT
<213> ORGANISM: artificial sequence
<220> FEATURE:
<223> OTHER INFORMATION: anti-CD3 scFv

<400> SEQUENCE: 16
```

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Gly Gly Gly Gly Ser Gly Gly

```
                    100                 105                 110
Gly Gly Ser Gly Gly Gly Ser Gln Val Gln Leu Val Gln Ser Gly
            115                 120                 125
Gly Gly Val Val Gln Pro Gly Arg Ser Leu Arg Leu Ser Cys Lys Ala
            130                 135                 140
Ser Gly Tyr Thr Phe Thr Arg Tyr Thr Met His Trp Val Arg Gln Ala
145                 150                 155                 160
Pro Gly Lys Gly Leu Glu Trp Ile Gly Tyr Ile Asn Pro Ser Arg Gly
                165                 170                 175
Tyr Thr Asn Tyr Asn Gln Lys Val Lys Asp Arg Phe Thr Ile Ser Arg
                180                 185                 190
Asp Asn Ser Lys Asn Thr Ala Phe Leu Gln Met Asp Ser Leu Arg Pro
            195                 200                 205
Glu Asp Thr Gly Val Tyr Phe Cys Ala Arg Tyr Tyr Asp Asp His Tyr
            210                 215                 220
Cys Leu Asp Tyr Trp Gly Gln Gly Thr Pro Val Thr Val Ser Ser Asp
225                 230                 235                 240
Pro

<210> SEQ ID NO 17
<211> LENGTH: 45
<212> TYPE: PRT
<213> ORGANISM: artificial sequence
<220> FEATURE:
<223> OTHER INFORMATION: CD8 hinge

<400> SEQUENCE: 17

Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
                20                  25                  30
Gly Ala Val His Thr Arg Gly Leu Asp Phe Ala Cys Asp
            35                  40                  45

<210> SEQ ID NO 18
<211> LENGTH: 24
<212> TYPE: PRT
<213> ORGANISM: artificial sequence
<220> FEATURE:
<223> OTHER INFORMATION: CD8 trans

<400> SEQUENCE: 18

Ile Tyr Ile Trp Ala Pro Leu Ala Gly Thr Cys Gly Val Leu Leu Leu
1               5                   10                  15
Ser Leu Val Ile Thr Leu Tyr Cys
                20

<210> SEQ ID NO 19
<211> LENGTH: 155
<212> TYPE: PRT
<213> ORGANISM: artificial sequence
<220> FEATURE:
<223> OTHER INFORMATION: 41BB-CD3z

<400> SEQUENCE: 19

Arg Arg Gly Arg Lys Lys Leu Leu Tyr Ile Phe Lys Gln Pro Phe Met
1               5                   10                  15
Arg Pro Val Gln Thr Thr Gln Glu Glu Asp Gly Cys Ser Cys Arg Phe
                20                  25                  30
```

```
Pro Glu Glu Glu Gly Gly Cys Glu Leu Arg Val Lys Phe Ser Arg
         35                  40                  45

Ser Ala Asp Ala Pro Ala Tyr Gln Gln Gly Gln Asn Gln Leu Tyr Asn
 50                  55                  60

Glu Leu Asn Leu Gly Arg Arg Glu Glu Tyr Asp Val Leu Asp Lys Arg
 65                  70                  75                  80

Arg Gly Arg Asp Pro Glu Met Gly Gly Lys Pro Arg Arg Lys Asn Pro
                 85                  90                  95

Gln Glu Gly Leu Tyr Asn Glu Leu Gln Lys Asp Lys Met Ala Glu Ala
                100                 105                 110

Tyr Ser Glu Ile Gly Met Lys Gly Glu Arg Arg Gly Lys Gly His
                115                 120                 125

Asp Gly Leu Tyr Gln Gly Leu Ser Thr Ala Thr Lys Asp Thr Tyr Asp
            130                 135                 140

Ala Leu His Met Gln Ala Leu Pro Pro Arg Glu
145                 150                 155

<210> SEQ ID NO 20
<211> LENGTH: 25
<212> TYPE: PRT
<213> ORGANISM: artificial sequence
<220> FEATURE:
<223> OTHER INFORMATION: 2A

<400> SEQUENCE: 20

Ser His Gly Gly Ser Gly Glu Gly Arg Gly Ser Leu Leu Thr Cys Gly
 1               5                  10                  15

Asp Val Glu Glu Asn Pro Gly Pro His
             20                  25

<210> SEQ ID NO 21
<211> LENGTH: 234
<212> TYPE: PRT
<213> ORGANISM: artificial sequence
<220> FEATURE:
<223> OTHER INFORMATION: BFP

<400> SEQUENCE: 21

Met Met Ser Glu Leu Ile Lys Glu Asn Met His Met Lys Leu Tyr Met
 1               5                  10                  15

Glu Gly Thr Val Asp Asn His His Phe Lys Cys Thr Ser Glu Gly Glu
             20                  25                  30

Gly Lys Pro Tyr Glu Gly Thr Gln Thr Met Arg Ile Lys Val Val Glu
         35                  40                  45

Gly Gly Pro Leu Pro Phe Ala Phe Asp Ile Leu Ala Thr Ser Phe Leu
 50                  55                  60

Tyr Gly Ser Lys Thr Phe Ile Asn His Thr Gln Gly Ile Pro Asp Phe
 65                  70                  75                  80

Phe Lys Gln Ser Phe Pro Glu Gly Phe Thr Trp Glu Arg Val Thr Thr
                 85                  90                  95

Tyr Glu Asp Gly Gly Val Leu Thr Ala Thr Gln Asp Thr Ser Leu Gln
                100                 105                 110

Asp Gly Cys Leu Ile Tyr Asn Val Lys Ile Arg Gly Val Asn Phe Thr
            115                 120                 125

Ser Asn Gly Pro Val Met Gln Lys Lys Thr Leu Gly Trp Glu Ala Phe
        130                 135                 140

Thr Glu Thr Leu Tyr Pro Ala Asp Gly Gly Leu Glu Gly Arg Asn Asp
145                 150                 155                 160
```

```
Met Ala Leu Lys Leu Val Gly Gly Ser His Leu Ile Ala Asn Ile Lys
            165                 170                 175

Thr Thr Tyr Arg Ser Lys Lys Pro Ala Lys Asn Leu Lys Met Pro Gly
            180                 185                 190

Val Tyr Tyr Val Asp Tyr Arg Leu Glu Arg Ile Lys Glu Ala Asn Asn
            195                 200                 205

Glu Thr Tyr Val Glu Gln His Glu Val Ala Val Ala Arg Tyr Cys Asp
            210                 215                 220

Leu Pro Ser Lys Leu Gly His Lys Leu Asn
225                 230

<210> SEQ ID NO 22
<211> LENGTH: 745
<212> TYPE: PRT
<213> ORGANISM: artificial sequence
<220> FEATURE:
<223> OTHER INFORMATION: 30527

<400> SEQUENCE: 22

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Ser Ala Ser Ser
            35                  40                  45

Ser Val Ser Tyr Met Asn Trp Tyr Gln Gln Thr Pro Gly Lys Ala Pro
        50                  55                  60

Lys Arg Trp Ile Tyr Asp Thr Ser Lys Leu Ala Ser Gly Val Pro Ser
65                  70                  75                  80

Arg Phe Ser Gly Ser Gly Ser Gly Thr Asp Tyr Thr Phe Thr Ile Ser
                85                  90                  95

Ser Leu Gln Pro Glu Asp Ile Ala Thr Tyr Tyr Cys Gln Gln Trp Ser
            100                 105                 110

Ser Asn Pro Phe Thr Phe Gly Gln Gly Thr Lys Leu Gln Ile Gly Gly
            115                 120                 125

Gly Gly Ser Gly Gly Gly Ser Gly Gly Gly Ser Gln Val Gln
            130                 135                 140

Leu Val Gln Ser Gly Gly Gly Val Val Gln Pro Gly Arg Ser Leu Arg
145                 150                 155                 160

Leu Ser Cys Lys Ala Ser Gly Tyr Thr Phe Thr Arg Tyr Thr Met His
            165                 170                 175

Trp Val Arg Gln Ala Pro Gly Lys Gly Leu Glu Trp Ile Gly Tyr Ile
            180                 185                 190

Asn Pro Ser Arg Gly Tyr Thr Asn Tyr Asn Gln Lys Val Lys Asp Arg
            195                 200                 205

Phe Thr Ile Ser Arg Asp Asn Ser Lys Asn Thr Ala Phe Leu Gln Met
            210                 215                 220

Asp Ser Leu Arg Pro Glu Asp Thr Gly Val Tyr Phe Cys Ala Arg Tyr
225                 230                 235                 240

Tyr Asp Asp His Tyr Cys Leu Asp Tyr Trp Gly Gln Gly Thr Pro Val
                245                 250                 255

Thr Val Ser Ser Asp Pro Thr Thr Thr Pro Ala Pro Arg Pro Pro Thr
            260                 265                 270

Pro Ala Pro Thr Ile Ala Ser Gln Pro Leu Ser Leu Arg Pro Glu Ala
            275                 280                 285
```

```
Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Arg Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg Glu Ser His Gly Gly Ser Gly Glu Gly Arg Gly
                485                 490                 495

Ser Leu Leu Thr Cys Gly Asp Val Glu Glu Asn Pro Gly Pro His Met
            500                 505                 510

Met Ser Glu Leu Ile Lys Glu Asn Met His Met Lys Leu Tyr Met Glu
        515                 520                 525

Gly Thr Val Asp Asn His His Phe Lys Cys Thr Ser Glu Gly Glu Gly
530                 535                 540

Lys Pro Tyr Glu Gly Thr Gln Thr Met Arg Ile Lys Val Val Glu Gly
545                 550                 555                 560

Gly Pro Leu Pro Phe Ala Phe Asp Ile Leu Ala Thr Ser Phe Leu Tyr
                565                 570                 575

Gly Ser Lys Thr Phe Ile Asn His Thr Gln Gly Ile Pro Asp Phe Phe
            580                 585                 590

Lys Gln Ser Phe Pro Glu Gly Phe Thr Trp Glu Arg Val Thr Thr Tyr
        595                 600                 605

Glu Asp Gly Gly Val Leu Thr Ala Thr Gln Asp Thr Ser Leu Gln Asp
610                 615                 620

Gly Cys Leu Ile Tyr Asn Val Lys Ile Arg Gly Val Asn Phe Thr Ser
625                 630                 635                 640

Asn Gly Pro Val Met Gln Lys Lys Thr Leu Gly Trp Glu Ala Phe Thr
                645                 650                 655

Glu Thr Leu Tyr Pro Ala Asp Gly Gly Leu Glu Gly Arg Asn Asp Met
            660                 665                 670

Ala Leu Lys Leu Val Gly Gly Ser His Leu Ile Ala Asn Ile Lys Thr
        675                 680                 685

Thr Tyr Arg Ser Lys Lys Pro Ala Lys Asn Leu Lys Met Pro Gly Val
690                 695                 700
```

```
-continued

Tyr Tyr Val Asp Tyr Arg Leu Glu Arg Ile Lys Glu Ala Asn Asn Glu
705                 710                 715                 720

Thr Tyr Val Glu Gln His Glu Val Ala Val Ala Arg Tyr Cys Asp Leu
            725                 730                 735

Pro Ser Lys Leu Gly His Lys Leu Asn
            740             745
```

METHOD FOR IMPROVING PRODUCTION OF CAR T CELLS

TECHNICAL FIELD

The current disclosure relates generally to the field of immunology and relates in part to a method for reducing the proportion of TCR-positive cells, thus purifying TCR-negative (TCR−)-T cells, in particular in cell preparations for allogeneic immunotherapy wherein the TCR expression is inhibited but few cells still express a TCR using an exogenous polynucleotide or synthetic RNA encoding an anti-TCR chimeric antigen receptor (CAR) for a transient and controlled expression at the cell surface and eventually suppression of T cells still expressing a TCR.

SEQUENCE LISTING

The instant application contains a Sequence Listing which has been submitted electronically in ASCII format and is hereby incorporated by reference in its entirety.

BACKGROUND OF THE INVENTION

Chimeric antigen receptors (CARs) are artificial antibody-like molecules designed to convey antigen specificity to T cells. T cells expressing CARs have shown long-term efficacy for the treatment of particular types of cancer (Eshhar, 1997, Cancer Immunol Immunother 45(3-4) 131-1)36; Eshhar et al, 1993, Proc Natl Acad Sci USA 90(2): 720-724; Brocker and Karjalainen, 1998, Adv Immunol 68:257-269). The first generation of CARs include an antigen binding domain, a transmembrane domain and an intracellular domain, such as CD3ζ, selected to activate the T cell and provide specific immunity. However, the expansion and persistence of these CAR-modified T cells in vivo was hampered by the lack of costimulatory signals after engagement with target antigens, as many tumor cells downregulate their expression of the costimulatory molecules required for optimal and sustained T-cell function, proliferation and persistence. A second and third generation of CAR constructs were created to boost the T cell response, they have included one and two secondary costimulatory signals in tandem with CD3ζ. The costimulatory molecule mimics a "second signal" such as CD28, 4-1BB, OX-40, and CD27, that amplifies the activation of the CAR T cells to expand to high numbers and maintain long term functional persistence (Carpenito et al., 2009, Proc. Natl. Acad. Sci. USA 106:3360-3365; Song et al., 2012, Blood 119:696-706) and in clinical studies (Porter et al., 2011, N. Engl. J. Med. 365:725-733; Kalos et al., 2011, Sci. Transl. Med. 3:95ra73; Savoldo et al., 2011, J. Clin. Invest. 121:1822-1826); Hwu P, Yang J C, Cowherd R, Treisman J, Shafer G E, Eshhar Z, Rosenberg S A, 1995, "In vivo antitumor activity of T cells redirected with chimeric antibody/T-cell receptor genes." Cancer Res; 55:3369-73). However, these highly activated T cells resulted in enhanced toxicity due to cytokine storm and tumor lysis syndrome.

CD19 (Cluster of Differentiation 19) glycoprotein specific to the B-cell lineage, is one of the first target against which a CAR was prepared and used in cancer immunotherapies (Nadler, et al., 1983 J Immunol 131(1):244-250). The vast majority of B-acute lymphoblastic leukemia (B-ALL) uniformly express CD19, whereas expression is absent on non hematopoietic cells, as well as myeloid, erythroid, and T cells, and bone marrow stem cells. Clinical trials targeting CD19 on B-cell malignancies are underway with encouraging anti-tumor responses. Accordingly, CD19 represents an attractive target for immune-based therapies. Since, numerous other CARs were designed and their activity against pathological cells tested, including CAR specific for a specific TCR subunit as disclosed in EP3125934 A1.

One of the problems observed with CAR targeting an antigen expressed in T cells e.g., TCR, CD38, is T cell sororicide, that is cells kill each other.

To reduce CD38CAR+ T cells from committing sororicide, the inventors have previously described a method of preparing anti-CD38 CAR+ in T cells for immunotherapy, wherein endogenous CD38 gene is inactivated with a nuclease, resulting in T cells of CD38-CAR+ CD38-negative phenotype, thus, avoiding their mutual destruction, autostimulation or aggregation, as described in WO201515121454. However, the activity of such system is not controlled.

Another problem observed in patients treated with allogeneic CAR-T cells is the appearance Graft-versus-host disease (GvHD). GVHD is a medical complication following the receipt of transplanted tissue from a genetically different person. Immune cells (white blood cells) in the donated tissue (the graft) recognize the recipient (the host) as foreign (nonself). The transplanted immune cells then attack the host's body cells. GvHD can also occur after a blood transfusion if the blood products used have not been irradiated or treated with an approved pathogen reduction system. Whereas transplant rejection occurs when the host rejects the graft, GvHD occurs when the graft rejects the host. To remedy this, it is known to engineer the T cells by modifying one or more genes to reduce or abolish graft versus host disease (GvHD), by specifically targeting genes of the T cell Receptor (TCR) complex, such as the constant region of the TCR alpha subunit of TRAC gene using rare cutting endonucleases. This can be prepared, for example, by using a rare-cutting endonuclease transiently expressed from an mRNA electroporated into the cells. If well designed and specific, the rare-cutting endonuclease by introducing a mutation a deletion or allowing the insertion of an exogenous nucleotide, will interrupt the expression of the TCR subunit and ultimately TCR expression at the cell surface.

So far, the most accurate and safest technique to delete a TCR gene has been the use of a TALEN® gene editing tool which is highly specific and efficient. More than 90 percent of the cells can be engineered using this technique with undetectable level of off target as determined by guide seq. analysis. Cells are subsequently grown for about 10 to 12 days to obtain enough injectable doses.

The final step of the manufacturing process typically consists in purifying the TCR-negative cell fraction from grown cells before vialing the product.

The step of purification is crucial for depleting the alpha beta TCR-positive T cell fraction as much as possible, as this fraction could be directly responsible for GvHD when the engineered cells are injected into patients. Moreover, because the final product will undergo amplification once in a patient, even a tiny number of TCR-positive cells when amplified will result in the occurrence of GvHD. Despite sophisticated and cost-effective techniques of purification, homogenous populations devoid of detrimental activity when transplanted into a patient, are difficult to obtain and remains a challenge.

Thus, there is important a need to improve the manufacturing of such gene-modified cells for therapy.

SUMMARY OF THE INVENTION

The inventors have identified means to improve the compositions comprising allogeneic cells or to improve methods to prepare such medicaments.

As a general method the present invention provides

1. A method for destroying TCR-positive cells comprising:
   (a) a supply step of providing a population of cells comprising TCR-positive cells,
   (b) a transformation step comprising transiently expressing an anti-TCR chimeric antigen receptor (anti-TCR CAR) at the surface of cells, preferably anti-alpha beta TCR,
   (c) —a step of contacting cells transiently expressing the anti-TCR CAR with said population of cells comprising TCR-positive cell.

2. The method according to item 2 comprising a step of introducing an exogenous or a synthetic polynucleotide encoding said anti-TCR CAR into cells.

3. The method according to item 1 or 2 wherein said exogenous or synthetic polynucleotide encoding said anti-TCR CAR is a mRNA or a DNA comprising a sequence coding said anti-TCR CAR under the control of a conditional promoter.

Cells transiently expressing said anti-TCR CAR are cytotoxic cells or become cytotoxic upon binding of anti-TCR CAR to TCR and kill TCR-positive cells upon binding of anti-TCR CAR to TCR.

In some embodiments, the method for destroying TCR-positive cells described herein is part of a general method for manufacturing engineered cells for therapy.

Because the method of the invention is highly sensitive and allows the killing of very few TCR−+ cells, it is useful for the preparation of any cells or organs intended for engraftment into a patient to get rid of TCR+ cells.

A DNA comprising a sequence coding said anti-TCR CAR under the control of a conditional promoter means a transgene which expression is conditional and can be controlled by a drug. This uses a promoter whose expression is sensitive to an exogenous agent. As an example, a number of promoters may be suitable for this purpose, but two commonly used promoters include regulatory elements that are sensitive to tetracycline (an antibiotic) or ecdysone (a steroid hormone made by insects). Since there are no endogenous genes that respond to these compounds in mammalian cells, the presence of these promoters and the expression of tet-binding proteins or ecdysone binding proteins will have little effect on the function of endogenous genes. Generally, this strategy results in coordinate expression in all tissues, but more complex constructs can restrict expression to unique tissue types.

The present invention provides

4. A method for manufacturing engineered cells, comprising at least:
   a supply step, wherein immune cells from a donor are provided;
   a disruption step, wherein the cells are engineered by disrupting at least one gene encoding an endogenous T Cell Receptor (TCR) component; followed by or concomitantly to,
   a first transformation step, wherein the cells are modified by introducing at least one exogenous polynucleotide encoding a recombinant chimeric antigen receptor (CAR) into the genome of said cells, followed by:
   a second transformation step for transiently expressing an anti-TCR chimeric antigen receptor (anti-TCR CAR).

In one embodiment the disruption step and first transformation step are carried out at the same time.

In a preferred embodiment the disruption step takes place at least 12 hours, or at least one day before the first transformation step, or at least two days before the first transformation step, or at least three days before the first transformation step, or at least four days before the first transformation step.

The disruption step is carried out using a rare cutting endonuclease, preferably a TAL-effector endonuclease or a CRISPR related endonuclease.

In particular embodiments, the second transformation step takes place after the first transformation step.

In one embodiment the first and second transformation step are carried out at the same time.

In a preferred embodiment the first transformation step takes place at least one day before the second transformation step, or at least two days before the second transformation step, or at least three days before the second transformation step, or at least four days before the second transformation step.

Thus, in a preferred embodiment, the first transformation step to introduce a gene encoding a CAR into the cells means introducing a CAR into a gene encoding the TCR.

The method of item 4 wherein the second transformation step comprises: introducing into the cells an exogenous or a synthetic polynucleotide encoding an anti-TCR CAR, such as a synthetic mRNA encoding an anti-TCR CAR or a DNA comprising a sequence coding said anti-TCR CAR under the control of a conditional promoter.

In a preferred embodiment, the first transformation step to introduce an exogenous gene encoding a CAR means inserting a CAR encoding sequence into a gene encoding the TCR, consequently the disruption step to inactivate the TCR is achieved by inserting an open reading frame into the TCR gene, preferably the sequence encoding the constant region of the alpha TCR subunit (TRAC gene).

According to the present invention, other endogenous (or genomic) sequences may be engineered (additional disruption step), additional exogenous sequence(s) may be introduced into the genome (third transformation step).

Preferably cells transiently expressing an anti-TCR CAR have a potential to be cytotoxic against TCR-positive cells.

A TCR component to be inactivated may be an alphaTCR subunit, a beta1 TCR subunit, a beta2 TCR subunit, a gamma TCR subunit, a delta TCR subunit, a combination thereof, preferably an alphaTCR subunit, a beta1 TCR subunit, a beta2 TCR subunit, a combination thereof, more preferably an alphaTCR subunit, 5. The method of any one of item 4 or 5 comprising successively:
   the supply step;
   optionally, an activation step;
   the disruption step to inactivate a TCR component;
   the first transformation step; for introducing a CAR
   the second transformation step for transiently expressing an anti-TCR CAR,
   an additional disruption step;
   an expansion step;
   an optional purification step;
   a fill and finish step.

In particular embodiments, the method of the invention comprises successively:

the supply step;
optionally, the activation step;
the disruption step;
a purification step;
the additional disruption step;
the first transformation step;
the expansion step;
the second transformation step for transiently expressing an anti-TCR CAR,
the fill and finish step.
or which successively comprises:
the supply step;
optionally, the activation step;
the disruption step;
the first transformation step;
the additional disruption step;
an expansion step;
a differentiation and/or maturing step
an optional purification step;
the second transformation step for transiently expressing an anti-TCR CAR,
the fill and finish step;
or which successively comprises:
the supply step;
optionally, the activation step;
the disruption step;
the additional disruption step;
the first transformation step;
an expansion step;
a differentiation and/or maturing step
the second transformation step for transiently expressing an anti-TCR CAR,
a fill and finish step.

The present invention encompasses any combination of steps comprising those of the general method, provided that transient expression of anti-TCR CAR takes place in cells with a cytotoxic activity, preferably with a cytolytic activity, and in the presence of TCR positive cells.

The invention relates to:

6. The method for manufacturing engineered cells according to any one of items 4 to 6, comprising at least:
   a supply step, wherein cells from a healthy donor are provided; wherein the donor is not a patient
   a disruption step, wherein the cells are modified by disrupting at least one gene encoding an endogenous T Cell Receptor (TCR) component; followed by, before, after or concomitantly,
   a first transformation step, wherein the cells are modified by introducing at least one polynucleotide encoding a recombinant chimeric receptor into said cells
   followed by:
      second transformation step for transiently expressing an anti-TCR CAR, a fill and finish step.

7. The method according to any one of items 4 to 7 wherein said anti-TCR CAR
   is specific for an epitope of a TCR,
   is specific for an epitope of a TCR-associated protein,
   is specific for an epitope of a CD3 subunit,
   is specific for an epitope of a TCR subunit,
   is specific for a combination of TCR subunits,
   is specific for an epitope of a TCR alpha subunit,
   is specific for an epitope of a TCR beta 1 or TCR beta 2 subunit
   is specific for a (common) epitope of a TCR alpha beta subunit.

CD3 consists of a protein complex and is composed of four distinct chains. In mammals, the complex contains a CD3γ chain, a CD3δ chain, and two CD3ε chains. CD3γ, CD3δ, and CD3ε chains are highly related cell-surface proteins of the immunoglobulin superfamily containing a single extracellular immunoglobulin domain. These chains associate with the T-cell receptor (TCR) and the ζ-chain (zeta-chain) to generate an activation signal in T lymphocytes. The TCR, ζ-chain, and CD3 molecules together constitute the TCR complex.

8. The method of any one of items 4 to 8 wherein said exogenous or a synthetic polynucleotide encoding said anti-TCR CAR comprises a sequence of SEQ ID NO 2, or a succession of the following sequences: SEQ ID NO 1-SEQ ID NO 2-SEQ ID NO 3-SEQ ID NO 4, and SEQ ID NO 5.

The present invention encompasses an anti-TCR CAR comprising
   a. an extra cellular ligand binding-domain comprising a VH and a VL from a monoclonal antibody directed against a TCR (alpha beta TCR, gamma delta TCR, beta TCR, TCR subunit (alpha, or beta 1, or beta 2 or gamma or delta), or a TCR-associated protein; (CD3, CD28),
   b. a hinge chosen in the group consisting of CD8α, FcERIII gamma and IgG1;
   c. a CD8α transmembrane domain;
   d. a cytoplasmic domain including a CD37 signaling domain and;
   a 4-1BB co-stimulatory domain,
   An anti-TCR CAR of SEQ ID NO 22

The present invention encompasses a vector coding an anti-TCR CAR, preferably, a vector of SEQ ID NO 8 or 12.

The present invention encompasses a scfv encoding an anti-TCR scfv, preferably of SEQ ID NO 2 or a sequence encoding said scfv, preferably of SEQ ID NO 16.

The present invention encompasses means for preparing a scfv or an anti-TCR CAR according to the present invention, preferably means of SEQ ID NO 13 and SEQ ID NO 14.

In one embodiment the following sequences are produced and used according to the invention:

| | |
|---|---|
| CD8 signal seq | ATGGCTTTGCCTGTCACTGCCTTGCTGCTTCCACTTGCTCTGTTGTTGCACGCCGCAAGACCC (SEQ ID NO: 1) |
| anti-CD3 scFv | GATATTCAGATGACCCAGTCCCCCTCCTCCCTGTCCGCTTCCGTCGGCGATAGAGTCACCATTA<br>CCTGTTCAGCCAGTAGTTCCGTGTCTTACATGAACTGGTATCAGCAGACCCCAGGCAAGGCACC<br>TAAGCGGTGGATCTACGACACATCCAAGCTGGCCTCTGGAGTGCCCAGCCGGTTCTCCGGCTC<br>TGGCAGCGGCACCGACTATACCTTTACAATCAGCTCCCTGCAGCCTGAGGACATCGCCACATAC<br>TATTGCCAGCAGTGGTCTAGCAATCCATTCACCTTTGGCCAGGGAACAAAGCTGCAGATCGGAG<br>GAGGAGGCAGCGGCGGAGGAGGCTCCGGCGGCGGCGGCTCTCAGGTGCAGCTGGTGCAGTC<br>CGGAGGAGGAGTGGTGCAGCCCGGCAGAAGCCTGCGGCTGAGCTGTAAGGCCAGCGGCTACA<br>CCTTCACACGGTATACCATGCACTGGGTGAGACAGGCACCAGGCAAGGGCCTGGAGTGGATCG<br>GCTACATCAACCCCAGCAGAGGCTACACAAACTATAATCAGAAGGTGAAGGACAGGTTCACCAT<br>CTCCCGCGATAACTCTAAGAATACAGCCTTTCTGCAGATGGACTCCCTGAGGCCTGAGGATACC |

-continued

GGCGTGTATTTTTGCGCCCGCTATTATGATGACCATTACTGTCTGGACTATTGGGGGCAGGGAA
CACCCGTGACTGTGAGCTCGGATCCC (SEQ ID NO: 2)

CD8 hinge
ACCACAACCCCCGCTCCAAGGCCCCCTACCCCCGCACCAACTATTGCCTCCCAGCCACTCTCAC
TGCGGCCTGAGGCCTGTCGGCCCGCTGCTGGAGGCGCAGTGCATACAAGGGGCCTCGATTTC
GCCTGCGAT (SEQ ID NO: 3)

CD8 trans
ATTTACATCTGGGCACCCCTCGCCGGCACCTGCGGGGTGCTTCTCCTCTCCCTGGTGATTACCC
TGTATTGC (SEQ ID NO: 4)

41BB-CD3z
AGACGGGGCCGGAAGAAGCTCCTCTACATTTTTAAGCAGCCTTTCATGCGGCCAGTGCAGACAA
CCCAAGAGGAGGATGGGTGTTCCTGCAGATTCCCTGAGGAAGAGGAAGGCGGGTGCGAGCTGA
GAGTGAAGTTCTCCAGGAGCGCAGATGCCCCCGCCTATCAACAGGGCCAGAACCAGCTCTACA
ACGAGCTTAACCTCGGGAGGCGCGAAGAATACGACGTGTTGGATAAGAGAAGGGGGCGGGACC
CCGAGATGGGAGGAAAGCCCCGGAGGAAGAACCCTCAGGAGGGCCTGTACAACGAGCTGCAG
AAGGATAAGATGGCCGAGGCCTACTCAGAGATCGGGATGAAGGGGGAGCGGCGCCGCGGGAA
GGGGCACGATGGGCTCTACCAGGGGCTGAGCACAGCCACAAAGGACACATACGACGCCTTGCA
CATGCAGGCCCTTCCACCCCGGGAA (SEQ ID NO: 5)

2A
TCCCATGGAGGAAGCGGAGAGGGACGAGGAAGCCTGCTGACCTGCGGGGACGTGGAGGAAAA
CCCAGGACCTCAT (SEQ ID NO: 6)

BFP
ATGATGAGCGAGCTGATTAAGGAGAACATGCACATGAAGCTGTACATGGAGGGCACCGTGGACA
ACCATCACTTCAAGTGCACATCCGAGGGCGAAGGCAAGCCCTACGAGGGCACCCAGACCATGA
GAATCAAGGTGGTCGAGGGCGGCCCTCTCCCCTTCGCCTTCGACATCCTGGCTACTAGCTTCCT
CTACGGCAGCAAGACCTTCATCAACCACACCCAGGGCATCCCCGACTTCTTCAAGCAGTCCTTC
CCTGAGGGCTTCACATGGGAGAGAGTCACCACATACGAGGACGGGGGCGTGCTGACCGCTACC
CAGGACACCAGCCTCCAGGACGGCTGCCTCATCTACAACGTCAAGATCAGAGGGGTGAACTTCA
CATCCAACGGCCCTGTGATGCAGAAGAAAACACTCGGCTGGGAGGCCTTCACCGAGACGCTGT
ACCCCGCTGACGGCGGCCTGGAAGGCAGAAACGACATGGCCCTGAAGCTCGTGGGCGGGAGC
CATCTGATCGCAAACATCAAGACCACATATAGATCCAAGAAACCCGCTAAGAACCTCAAGATGCC
TGGCGTCTACTATGTGGACTACGACTGGAAAGAATCAAGGAGGCCAACAACGAGACCTACGTC
GAGCAGCACGAGGTGGCAGTGGCCAGATACTGCGACCTCCCTAGCAAACTGGGGCACAAGCTG
AAT (SEQ ID NO: 7)

30527
ATGGCTTTGCCTGTCACTGCCTTGCTGCTTCCACTTGCTCTGTTGTTGCACGCCGCAAGACCCG
ATATTCAGATGACCCAGTCCCCCTCCTCCCTGTCCGCTTCCGTCGGCGATAGAGTCACCATTAC
CTGTTCAGCCAGTAGTTCCGTGTCTTACATGAACTGGTATCAGCAGACCCCAGGCAAGGCACCT
AAGCGGTGGATCTACGACACATCCAAGCTGGCCTCTGGAGTGCCCAGCCGGTTCTCCGGCTCT
GGCAGCGGCACCGACTATACCTTTACAATCAGCTCCCTGCAGCCTGAGGACATCGCCACATACT
ATTGCCAGCAGTGGTCTAGCAATCCATTCACCTTTGGCCAGGGAACAAAGCTGCAGATCGGAGG
AGGAGGCAGCGGCGGAGGAGGCTCCGGCGGCGGCGGCTCTCAGGTGCAGCTGGTGCAGTCC
GGAGGAGGAGTGGTGCAGCCCGGCAGAAGCCTGCGGCTGAGCTGTAAGGCCAGCGGCTACAC
CTTCACACGGTATACCATGCACTGGGTGAGACAGGCACCAGGCAAGGGCCTGGAGTGGATCGG
CTACATCAACCCCAGCAGAGGCTACACAAACTATAATCAGAAGGTGAAGGACAGGTTCACCATC
TCCCGCGATAACTCTAAGAATACAGCCTTTCTGCAGATGGACTCCCTGAGGCCTGAGGATACCG
GCGTGTATTTTTGCGCCCGCTATTATGATGACCATTACTGTCTGGACTATTGGGGGCAGGGAAC
ACCCGTGACTGTGAGCTCGGATCCCACCACAACCCCCGCTCCAAGGCCCCCTACCCCCGGCACC
AACTATTGCCTCCCAGCCACTCTCACTGCGGCCTGAGGCCTGTCGGCCCGCTGCTGGAGGCGC
AGTGCATACAAGGGGCCTCGATTTCGCCTGCGATATTTACATCTGGGCACCCCTCGCCGGCACC
TGCGGGGTGCTTCTCCTCTCCCTGGTGATTACCCTGTATTGCAGACGGGGCCGGAAGAAGCTC
CTCTACATTTTTAAGCAGCCTTTCATGCGGCCAGTGCAGACAACCCAAGAGGAGGATGGGTGTT
CCTGCAGATTCCCTGAGGAAGAGGAAGGCGGGTGCGAGCTGAGAGTGAAGTTCTCCAGGAGCG
CAGATGCCCCCGCCTATCAACAGGGCCAGAACCAGCTCTACAACGAGCTTAACCTCGGGAGGC
GCGAAGAATACGACGTGTTGGATAAGAGAAGGGGGCGGGACCCCGAGATGGGAGGAAAGCCC
CGGAGGAAGAACCCTCAGGAGGGCCTGTACAACGAGCTGCAGAAGGATAAGATGGCCGAGGC
CTACTCAGAGATCGGGATGAAGGGGGAGCGGCGCCGCGGGAAGGGGCACGATGGGCTCTACC
AGGGGCTGAGCACAGCCACAAAGGACACATACGACGCCTTGCACATGCAGGCCCTTCCACCCC
GGGAATCCCATGGAGGAAGCGGAGAGGGACGAGGAAGCCTGCTGACCTGCGGGGACGTGGAG
GAAAACCCAGGACCTCATATGATGAGCGAGCTGATTAAGGAGAACATGCACATGAAGCTGTACA
TGGAGGGCACCGTGGACAACCATCACTTCAAGTGCACATCCGAGGGCGAAGGCAAGCCCTACG
AGGGCACCCAGACCATGAGAATCAAGGTGGTCGAGGGCGGCCCTCTCCCCTTCGCCTTCGACA
TCCTGGCTACTAGCTTCCTCTACGGCAGCAAGACCTTCATCAACCACACCCAGGGCATCCCCGA
CTTCTTCAAGCAGTCCTTCCCTGAGGGCTTCACATGGGAGAGAGTCACCACATACGAGGACGGG
GGCGTGCTGACCGCTACCCAGGACACCAGCCTCCAGGACGGCTGCCTCATCTACAACGTCAAG
ATCAGAGGGGTGAACTTCACATCCAACGGCCCTGTGATGCAGAAGAAAACACTCGGCTGGGAG
GCCTTCACCGAGACGCTGTACCCCGCTGACGGCGGCCTGGAAGGCAGAAACGACATGGCCCTG
AAGCTCGTGGGCGGGAGCCATCTGATCGCAAACATCAAGACCACATATAGATCCAAGAAACCCG
CTAAGAACCTCAAGATGCCTGGCGTCTACTATGTGGACTACGACTGGAAAGAATCAAGGAGGC
CAACAACGAGACCTACGTCGAGCAGCACGAGGTGGCAGTGGCCAGATACTGCGACCTCCCTAG
CAAACTGGGGCACAAGCTGAAT (SEQ ID NO: 8)

T7 promoter
TAATACGACTCACTATA (SEQ ID NO: 9)

mouse hba 3'UTR
GCTGCCTTCTGCGGGGCTTGCCTTCTGGCCATGCCCTTCTTCTCTCCCTTGCACCTGTACCTCTT
GGTCTTTGAATAAAGCCTGAGTAGGAAG (SEQ ID NO: 10)

```
120A          AAAAAAAAAAAAAAAAAAAAAAAAAAAAAAAAAAAAAAAAAAAAAAAAAAAAAAAAAAAA
polyA         AAAAAAAAAAAAAAAAAAAAAAAAAAAAAAAAAAAAAAAAAAAAAAAAAAAAAA
              (SEQ ID NO: 11)

30697         TAATACGACTCACTATAGGCTAGCGCCGCCACCATGGCTTTGCCTGTCACTGCCTTGCTGCTTC
              CACTTGCTCTGTTGTTGCACGCCGCAAGACCCGATATTCAGATGACCCAGTCCCCCTCCTCCCT
              GTCCGCTTCCGTCGGCGATAGAGTCACCATTACCTGTTCAGCCAGTAGTTCCGTGTCTTACATGA
              ACTGGTATCAGCAGACCCCAGGCAAGGCACCTAAGCGGTGGATCTACGACACATCCAAGCTGG
              CCTCTGGAGTGCCCAGCCGGTTCTCCGGCTCTGGCAGCGGCACCGACTATACCTTTACAATCAG
              CTCCCTGCAGCCTGAGGACATCGCCACATACTATTGCCAGCAGTGGTCTAGCAATCCATTCACC
              TTTGGCCAGGGAACAAAGCTGCAGATCGGAGGAGGAGGCAGCGGCGGAGGAGGCTCCGGCGG
              CGGCGGCTCTCAGGTGCAGCTGGTGCAGTCCGGAGGAGGAGTGGTGCAGCCCGGCAGAAGCC
              TGCGGCTGAGCTGTAAGGCCAGCGGCTACACCTTCACACGGTATACCATGCACTGGGTGAGAC
              AGGCACCAGGCAAGGGCCTGGAGTGGATCGGCTACATCAACCCCAGCAGAGGCTACACAAACT
              ATAATCAGAAGGTGAAGGACAGGTTCACCATCTCCCGCGATAACTCTAAGAATACAGCCTTTCTG
              CAGATGGACTCCCTGAGGCCTGAGGATACCGGCGTGTATTTTGCGCCCGCTATTATGATGACC
              ATTACTGTCTGGACTATTGGGGGCAGGGAACACCCGTGACTGTGAGCTCGGATCCCACCACAAC
              CCCCGCTCCAAGGCCCCCTACCCCCGCACCAACTATTGCCTCCCAGCCACTCTCACTGCGGCC
              TGAGGCCTGTCGGCCCGCTGCTGGAGGCGCAGTGCATACAAGGGGCCTCGATTTCGCCTGCGA
              TATTTACATCTGGGCACCCCTCGCCGGCACCTGCGGGGTGCTTCTCCTCTCCCTGGTGATTACC
              CTGTATTGCAGACGGGGCCGGAAGAAGCTCCTCTACATTTTTAAGCAGCCTTTCATGCGGCCAG
              TGCAGACAACCCAAGAGGAGGATGGGTGTTCCTGCAGATTCCCTGAGGAAGAGGAAGGCGGGT
              GCGAGCTGAGAGTGAAGTTCTCCAGGAGCGCAGATGCCCCCGCCTATCAACAGGGCCAGAACC
              AGCTCTACAACGAGCTTAACCTCGGGAGGCGCGAAGAATACGACGTGTTGGATAAGAGAAGGG
              GGCGGGACCCCGAGATGGGAAAGCCCCGGAGGAAGAACCCTCAGGAGGGCCTGTACAAC
              GAGCTGCAGAAGGATAAGATGGCCGAGGCCTACTCAGAGATCGGGATGAAGGGGGAGCGGCG
              CCGCGGGAAGGGGCACGATGGGCTCTACCAGGGGCTGAGCACAGCCACAAAGGACACATACG
              ACGCCTTGCACATGCAGGCCCTTCCACCCCGGGAATCCCATGGAGGAAGCGGAGAGGGACGA
              GGAAGCCTGCTGACCTGCGGGGACGTGGAGGAAAACCCAGGACCTCATATGATGAGCGAGCTG
              ATTAAGGAGAACATGCACATGAAGCTGTACATGGAGGGCACCGTGGACAACCATCACTTCAAGT
              GCACATCCGAGGGCGAAGGCAAGCCCTACGAGGGCACCCAGACCATGAGAATCAAGGTGGTCG
              AGGGCGGCCCTCTCCCCTTCGCCTTCGACATCCTGGCTACTAGCTTCCTCTACGGCAGCAAGAC
              CTTCATCAACCACACCCAGGGCATCCCCGACTTCTTCAAGCAGTCCTTCCCTGAGGGCTTCACA
              TGGGAGAGAGTCACCACATACGAGGACGGGGCGTGCTGACCGCTACCCAGGACACCAGCCT
              CCAGGACGGCTGCCTCATCTACAACGTCAAGATCAGAGGGGTGAACTTCACATCCAACGGCCCT
              GTGATGCAGAAGAAAACACTCGGCTGGGAGGCCTTCACCGAGACGCTGTACCCCGCTGACGGC
              GGCCTGGAAGGCAGAAACGACATGGCCCTGAAGCTCGTGGGCGGGAGCCATCTGATCGCAAAC
              ATCAAGACCACATATAGATCCAAGAAACCCGCTAAGAACCTCAAGATGCCTGGCGTCTACTATGT
              GGACTACAGACTGGAAAGAATCAAGGAGGCCAACAACGAGACCTACGTCGAGCAGCACGAGGT
              GGCAGTGGCCAGATACTGCGACCTCCCTAGCAAACTGGGGCACAAGCTGAATTGACGGCCGAC
              TGATAACTCGAGGCTGCCTTCTGCGGGGCTTGCCTTCTGGCCATGCCCTTCTTCTCTCCCTTGC
              ACCTGTACCTCTTGGTCTTTGAATAAAGCCTGAGTAGGAAGGTCGAGGCGGCCAACAACAAAAA
              AAAAAAAAAAAAAAAAAAAAAAAAAAAAAAAAAAAAAAAAAAAAAAAAAAAAAAAAAAAA
              AAAAAAAAAAAAAAAAAAAAAAAAAAAAAAAAAAAAAAAAAAAAAAAAAA (SEQ ID NO: 12)

oligo1        GCATCGTAATACGACTCACTATAGGGCAGGCCACCatggctttgcctgtcactgcc
              (SEQ ID NO: 13)

oligo2        TCAATTCAGCTTGTGCCCCAG (SEQ ID NO: 14)

CD8           MALPVTALLLPLALLLHAARP (SEQ ID NO: 15)
signal
seq anti-         DIQMTQSPSSLSASVGDRVTITCSASSSVSYMNVVYQQTPGKAPKRWIYDTSKLASGVPSRFSGSGS
CD3           GTDYTFTISSLQPEDIATYYCQQWSSNPFTFGQGTKLQIGGGGSGGGGSGGGGSQVQLVQSGGGV
scFv          VQPGRSLRLSCKASGYTFTRYTMHWVRQAPGKGLEWIGYINPSRGYTNYNQKVKDRFTISRDNSKN
              TAFLQMDSLRPEDTGVYFCARYYDDHYCLDYWGQGTPVTVSSDP (SEQ ID NO: 16)

CD8           TTTPAPRPPTPAPTIASQPLSLRPEACRPAAGGAVHTRGLDFACD (SEQ ID NO: 17)
hinge CD8           IYIWAPLAGTCGVLLLSLVITLYC (SEQ ID NO: 18)
trans 41BB-         RRGRKKLLYIFKQPFMRPVQTTQEEDGCSCRFPEEEEGGCELRVKFSRSADAPAYQQGQNQLYNEL
CD3z          NLGRREEYDVLDKRRGRDPEMGGKPRRKNPQEGLYNELQKDKMAEAYSEIGMKGERRRGKHDG
              LYQGLSTATKDTYDALHMQALPPRE (SEQ ID NO: 19)

2A            SHGGSGEGRGSLLTCGDVEENPGPH (SEQ ID NO: 20)

BFP           MMSELIKENMHMKLYMEGTVDNHHFKCTSEGEGKPYEGTQTMRIKVVEGGPLPFAFDILATSFLYGS
              KTFINHTQGIPDFFKQSFPEGFTWERVTTYEDGGVLTATQDTSLQDGCLIYNVKIRGVNFTSNGPVM
              QKKTLGWEAFTETLYPADGGLEGRNDMALKLVGGSHLIANIKTTYRSKKPAKNLKMPGVYYVDYRLE
              RIKEANNETYVEQHEVAVARYCDLPSKLGHKLN (SEQ ID NO: 21)

30527         MALPVTALLLPLALLLHAARPDIQMTQSPSSLSASVGDRVTITCSASSSVSYMNVVYQQTPGKAPKRW
              IYDTSKLASGVPSRFSGSGSGTDYTFTISSLQPEDIATYYCQQWSSNPFTFGQGTKLQIGGGGSGGGG
```

-continued

```
GSGGGGSQVQLVQSGGGVVQPGRSLRLSCKASGYTFTRYTMHWVRQAPGKGLEWIGYINPSRGY
TNYNQKVKDRFTISRDNSKNTAFLQMDSLRPEDTGVYFCARYYDDHYCLDYWGQGTPVTVSSDPTT
TPAPRPPTPAPTIASQPLSLRPEACRPAAGGAVHTRGLDFACDIYIWAPLAGTCGVLLLSLVITLYCRR
GRKKLLYIFKQPFMRPVQTTQEEDGCSCRFPEEEEGGCELRVKFSRSADAPAYQQGQNQLYNELNL
GRREEYDVLDKRRGRDPEMGGKPRRKNPQEGLYNELQKDKMAEAYSEIGMKGERRRGKGHDGLY
QGLSTATKDTYDALHMQALPPRESHGGSGEGRGSLLTCGDVEENPGPHMMSELIKENMHMKLYME
GTVDNHHFKCTSEGEGKPYEGTQTMRIKVVEGGPLPFAFDILATSFLYGSKTFINHTQGIPDFFKQSF
PEGFTWERVTTYEDGGVLTATQDTSLQDGCLIYNVKIRGVNFTSNGPVMQKKTLGWEAFTETLYPAD
GGLEGRNDMALKLVGGSHLIANIKTTYRSKKPAKNLKMPGVYYVDYRLERIKEANNETYVEQHEVAV
ARYCDLPSKLGHKLN (SEQ ID NO: 22)
```

The method according to any one of items 4 to 9 wherein cells are T cells, more preferably T cells exhibiting a cytolytic activity to obtain anti-TCR CAR expressing cells exhibiting a cytolytic activity upon binding of said anti-TCR CAR to TCR positive cells.

The method according to any one of items 4 to 10 wherein the step of introducing an exogenous or synthetic polynucleotide is carried out by electroporation.

The method of any one of items 4 to 9, wherein the introduction of said mRNA is obtained by transduction using a viral vector or transfection or lipofection The method according to any one of items 4 to 11 wherein the half-life of said anti-TCR CAR is from more than 12 hours to 10 days.

The method according to any one of items 4 to 12 wherein the half-life of said anti-TCR CAR mRNA is from 3 hours to 72 hours.

The method according to any one of items 1 to 9 wherein said mRNA transiently expresses the anti-TCR CAR for about 2 days or for a time period in a range of from about 1 to about 7 days, or about 2 to 5 days.

11. The method according to any one of items 4 to 13 wherein introducing a mRNA encoding an anti-TCR CAR specific for a TCR, a TCR subunit or combination of TCR subunits results in a transient expression of said anti-TCR CAR on the cell surface, binding of said anti-TCR CAR to CD3, to endogenous alpha beta, to gamma/delta TCR expressing cells and lyse of CD3, alpha beta and/or gamma TCR expressing cells.

12. The method according to any one of items 1 to 10 comprising a step of introducing a mutation, a deletion or an insertion affecting cell surface expression of the alpha beta TCR protein, preferably introducing an insertion of an exogenous polynucleotide into the TRAC (TCR alpha subunit) gene, more preferably introducing an insertion of an exogenous polynucleotide encoding a chimeric antigen receptor (CAR).

13. The method according to any one of items 1 to 12 comprising an optional step of purifying TCR-negative cells or separating TCR-negative cells from TCR positive cells, [to achieve between undetectable level of TCR-positive cells to 40% of TCR-positive cells],
   followed by
   the transformation step comprising introducing a mRNA encoding an anti-TCR chimeric antigen receptor (CAR) that recognized and binds to CD3, recognized and binds to endogenous alpha beta TCR and/or to gamma/delta TCR to achieve a transient expression of said anti-TCR CAR on the cell surface, binding to TCR expressing target cells, and lyse of TCR+ cells.

14. The method according to any one of items 4 to 13 to reach less than 5% or 0.05% or less of alpha beta TCR positive cells to preferably undetectable level of TCR-positive cells.

The method according to any one of the above to reach 0.05 for 100 total cells % or less alpha beta TCR positive cells to undetectable level of TCR-positive cells in a total of 1015 cells, 1014 cells, 1013 cells, 1012 cells, 1011 cells, 1010 cells, 109 cells, 108 cells, 107 cells, 106 cells, 105 cells.

15. The method according to any one of items 4 to 14 wherein a step of disruption comprises introducing a mRNA encoding a rare cutting endonuclease specific for a genomic sequence.

16. The method according to any one of items 4 to 15 wherein the rare cutting endonuclease is a TAL-effector protein or a CRISPR CAS9.

17. The method any one of items 4 to 16 comprising a transformation step of introducing into said cell an exogenous gene encoding a CAR, using a viral vector, preferably a viral vector comprising a AAV6 viral vector.

18. The method according to any one of items 4 to 17 wherein said gene targeted by said endonuclease is specific for a sequence comprised in a gene selected from the group consisting of a TCR gene, beta 2 microglobulin gene, a gene conferring sensitivity or resistance to a drug, a cytokine gene a combination thereof.

19. The method of any one of items 4 to 18, wherein amount of the antigen-encoding mRNA are within the range of 0.1 to 50 µg RNA for transfection of between 10×4 and 10×15 cells or for the transfection of between 10×6 and 10×7 cells.

20. The method of any one of items 4 to 19, wherein said genetically modified immune cells obtained are directly administered to a patient or to several patients.

21. the method according to any one of items 4 to 20, wherein said cells in the supply step comprise or are derived from T cells, inflammatory T-lymphocytes, cytotoxic T-lymphocytes, regulatory T-lymphocytes or helper T-lymphocytes, NK T cells.

22. The method according to any one of items 4 to 21, wherein said T-cells comprises or are derived from CD4+ T-lymphocytes and/or CD8+ T-lymphocytes.

The method of to any one of the above, wherein said cells are immune cells, and preferably, T cells or natural killer (NK) cells.

The method above, comprising a differentiation and/or maturing step and wherein said cells are a hematopoietic stem cells.

The method of any one of the above wherein said a cell is further defined as autologous or allogeneic in relation to recipient.

23. The method of any one of items 4 to 22, wherein the CAR, is specific for a cell surface antigen target selected from the group consisting of ROR1, EGFRvIII, BCMA, CD33, GD3, CD19, CD38, HSP70, CD30, FAP, HER2, CD79a, CD79b, CD123, CD22, CLL-1, MUC-1 GD2, O acetyl GD2, CS1.

The method of any one of item 1 to 24, wherein the CAR, is specific for a cell surface antigen target selected from the group consisting of CD19, BCMA, CD33, EGFRVIII, Flt3, WT1, CD70, MUC16, PRAME, TSPAN10, CLAUDIN18.2, DLL3, LY6G6D, Liv-1, CHRNA2, ADAM10, CD38, HSP70, CD30, FAP, HER2, CD79, CD123, CD22, CLL-1, MUC-1 GD2, O acetyl GD2, CS1, and combination thereof.

The method of any one of items 1 to 24, wherein the CAR, is specific for a cell surface antigen target selected from the group consisting of CD19, BCMA, CD33, EGFRVIII, Flt3, WT1, CD70, MUC16, PRAME, TSPAN10, CLAUDIN18.2, DLL3, LY6G6D, Liv-1, CHRNA2, ADAM10, and combination thereof.

24. The method of any one of items 4 to 23, wherein said CAR is a single-chain CAR (scCAR) or a multichain CAR (mcCAR);

The method of any one of item 4 to 24, wherein said scCAR has one of the polypeptide structure said structure comprising at least:
- an extra cellular ligand binding-domain comprising a VH and a VL from a monoclonal antibody directed against a cell surface antigen target;
- a hinge chosen in the group consisting of CD8α, FcERIII gamma and IgG1;
- a CD8α transmembrane domain;
- a cytoplasmic domain including a CD34 signaling domain and;
- a 4-1BB co-stimulatory domain.

The preferred CARs are specific for any one of the following antigens: CD38, HSP70, CD30, FAP, HER2, CD79a or CD79b, CD123, CD22, CLL-1, MUC-1 GD2, O acetyl GD2, CS1.

The preferred CAR architecture is adapted to the accessibility of said antigen on pathological cells and may be a CAR as described in WO2015107075A1.

25. The method of any one of item 4 to 24, wherein said method includes a further step of inactivating at least one gene involved in alloreactivity such as TCR, beta2M, regulatory factor X-associated ankyrin-containing protein (RFXANK), regulatory factor 5 (RFX5), regulatory factor X-associated protein (RFXAP), and class II transactivator (CIITA), TAP-1, a combination thereof).

Editing the following genes is adapted from WO2013158292 and relates to editing regulatory factor X-associated ankyrin-containing protein (RFXANK), regulatory factor 5 (RFX5), regulatory factor X-associated protein (RFXAP), class II transactivator (CIITA), or a combination thereof using specific TAL-effector protein designed for the purpose of the present invention.

26. The method of any one of items 4 to 25, wherein said method includes a further additional disruption step of inactivating at least one gene such as PDL1, Programmed Death 1 (PD-1), Cytotoxic T-Lymphocyte Antigen 4 (CTLA-4), LAG3 Tim3, BTLA, BY55, TIGIT, B7H5, LAIR1, SIGLEC10, 2B4.

27. The method of any one of items 4 to 26, wherein said method includes a further step of inactivating or overexpressing at least one gene involved in drug resistance selected from deoxycytidine kinase (dCk), hypoxanthine guanine phosphoribosyl transferase (HPRT), glucocorticoid receptor (GR), CD52, and a combination thereof.

28. The method of any one of items 4 to 27, wherein said method includes a further step of inactivating of at least one gene in the immune cell involved in drug hypersensitivity, such the genes encoding GGH, RhoA, CDK5, CXCR3, NR1H2, URG4, PARP14, AMPD3, CCDC38, NFU1 or CACNG5 protein.

29. A population of TCR negative CAR expressing immune cells obtainable according to a method according to any one of item 1 to 28.

30. A population of TCR negative CAR expressing immune cells according to item 29 for use as a medicament.

31. A pharmaceutical composition comprising a population of TCR negative CAR expressing immune cells according to item 29 or 30 and a pharmaceutically acceptable vehicle.

32. The population of TCR negative CAR expressing immune cells according to any of the item 29 to 30 or the pharmaceutical composition according to item 33 for use in the treatment of cancer, infection or immune disease.

33. The population of TCR negative CAR expressing immune cells according to any of the item 1 to 30 or the pharmaceutical composition according to item 32 for use in the treatment or prophylaxis of cancer, wherein said cancer is selected from Acute myeloid leukemia (AML), Chronic myeloid leukemia (CML), Acute lymphoblastic leukemia (ALL), Hodgkin lymphoma (HL) (relapsed, refractory), Non-Hodgkin lymphoma (NHL) (relapsed, refractory), Neuroblastoma, Ewing sarcoma, Multiple myeloma, Myelodysplastic syndromes, BPDCN, Gliomas, other solid tumors, including pancreatic or lung cancer, bladder cancer, colon cancer, breast cancer.

34. A method for treating a patient comprising:
Diagnosing said patient for the presence of pathological cells expressing an antigen marker on the cell surface;
Preparing a population of genetically modified CAR expressing immune cells according to any of the item 1 to 28; and
Administering said genetically modified cells to said patient diagnosed for said pathological cells.

The inventors have established that the number of TCR-positive cells, in particular the number of TCR-positive cells in a cells population comprising 5% or less TCR-positive cells can be further greatly reduced to undetectable level with the transient expression of a Chimeric antigen receptor (CAR) targeting the endogenous TCR supplied as mRNA, i.e., using anti-TCR CAR+ immune cells for a controlled amount of time. The anti-TCR CAR-encoding mRNA expression is self-limited and can be controlled using the techniques used herein. Following transient expression of the anti-TCR CAR on the cell surface of the TCR+ immune cells, a lysis among the TCR+ T-cells would be expected, since the anti-TCR CAR responds directly against the TCR presented on its cells. As observed by the inventors, the enrichment of TCR− T cells was accompanied with an improved antitumor activity in vitro and a significant decrease in GVHD when TCR_negative cells were used for immunotherapy.

The method of the present invention results in cells preparation that avoids many of the drawbacks of earlier CAR-based treatments. The invention is also providing a method that does not require a step of TCR− T cell purification that is cost effective, and prevent or limit expansion of the CAR+ immune cells once administered to a patient. That is, transfecting TCR+ immune cells with an mRNA encoding a CAR targeting a TCR on the cell surface for a limited time of about 1 to about 11 days, as presently described herein, would allow for autoactivation of the anti-TCR CAR+ cells in the presence of TCR+ expressing cells; lysis of TCR+ cells, ultimately degradation of the expressed mRNA in the absence of target TCR and enrichments of TCR-negative (TCR−) cells.

One advantage of the present invention is that there is no requirement to purify the expanded TCR− immune cells before administering to a patient. Another advantage is that there is no need to further expand the CAR+ immune cells by exogenous cytokines.

In one embodiment, the methods and compositions of the invention comprise genetically modified cells wherein the TCR gene was inactivated, and a CAR is integrated into the genome to be stably expressed in TCR-negative cells. In one embodiment, the methods and compositions of the invention comprise genetically modified CAR-expressing T cells.

The CAR that can be used with the method of the present invention (anti-TCR CAR and CAR for stable expression) and compositions of the invention include all types of the chimeric proteins, including first, second and third generation designs. The CARs introduced into the immune cells according to the methods described herein can also adopt designs such as single-chain or multi-chain structures as described in WO2014039523 incorporated herein by reference.

Immune cells include, but are not limited to, T cells, helper T cells (e.g., CD4+ cells), cytotoxic T cells (e.g., CD8+), memory T cells, regulatory T cells, tumor infiltrating lymphocytes (TILs, CD3+), CD8+ T cells, CD4+ T cells, Natural Killer-type T cells (NK-T), TCR-expressing or Natural Killer (NK) cells.

Immune cells include, but are not limited to, human primary immune cell, human primary immune T cell, human primary lymphoid cell, human primary stem cell, human primary progenitor cell.

In one embodiment, the method and compositions of the invention comprise genetically modified CAR+ natural killer (NK) cells lacking T-cell receptors (CD56+CD3 negative).

In one embodiment, the method and compositions of the invention comprise genetically modified CAR+ T cells expressing cell surface alpha beta T-cell receptors.

In one embodiment, the method and compositions of the invention comprise genetically modified CAR+ T cells expressing cell surface alpha beta T-cell receptors and comprising a TCR alpha gene with an insertion in the gene encoding the constant region of the TCR alpha subunit (TRAC gene).

In one embodiment, the composition and method of the invention comprise human primary cells wherein the TRAC gene comprises a genetic insertion generated by a rare cutting endonuclease and affecting cell surface expression of the endogenous alpha beta TCR, said genomic TRAC gene comprising from 5' to 3':
  (a) a 5' region of said human genomic TRAC gene upstream,
  (b) optionally, a domain targeted by said rare cutting endonuclease,
  (c) an insertion as compared to the wild type TRAC gene affecting the cell surface expression of the extracellular domain of the alpha beta TCR or the transmembrane domain of the alpha beta TCR,
  said insertion comprising an exogenous polynucleotide encoding a chimeric antigen receptor and an exogenous polynucleotide sequence selected from a stop codon, an IRES, a self-cleaving peptide in frame with the TRAC open reading frame, a termination sequence, a combination thereof.

In one embodiment, the composition and method of the invention comprise TAL-protein-modified human primary cells with undetectable off site cut as determined by guide seq analysis.

In one embodiment, the method and compositions of the invention comprise genetically modified CAR+ T cells lacking T-cell receptors, preferably are least 95% of genetically modified CAR+ T cells lacking T-cell receptors, at least 96%, at least 97%, at least 98%, at least 99%, at least 99.99% of genetically modified CAR+ T cells lacking T-cell receptors (to undetectable level of TCR positive cells).

In preferred embodiments, the compositions of the invention, such as those obtained using the method according to the present invention, comprise more than 95% genetically modified CAR+ T cells lacking T-cell receptors, more than 96%, more than 97%, more than 98%, more than 99%, more than 99.99% of genetically modified CAR+ T cells lacking T-cell receptors even more preferably undetectable level of TCR positive cells.

In another embodiment, the method and compositions of the invention comprise genetically modified CAR+ hematopoietic stem cells.

In particular, the invention includes compositions and methods comprising a nucleic acid molecule or a polynucleotide comprising an mRNA sequence encoding an anti-TCR CAR transiently expressed wherein the anti-TCR CAR comprises an antigen binding domain specific for a TCR, a transmembrane domain, and an intracellular domain of a costimulatory molecule to achieve expression of the anti-TCR CAR on the cell surface for a limited amount of time. In some embodiments, between the extracellular domain and the transmembrane domain of the CAR, or between the cytoplasmic domain and the transmembrane domain of the CAR, there may be incorporated a spacer domain or a hinge and/or an epitope specific a molecular antibody as described in WO2016120216A1.

The present invention relates generally to the use of T cells that stably express a CAR, e.g., the CAR is delivered to a cell in a lentivirus or AAV for insertion into the TCR gene and inactivation of the TCR gene while the anti-TCR CAR recognized by the TCR is supplied as mRNA. It is contemplated using cells RNA-engineered T cells in that the anti-TCR CAR is expressed for a limited time in the cell that is to say for 1 day to 7 days post transduction in vitro. It is also contemplated using genetically modified cells in which the anti-TCR CAR gene was inserted in a safe harbor gene by using nucleases and comprises a conditional promotor.

In one embodiment, the method for producing a population of CAR+ TCR− immune cells comprises (a) providing a cell; (b) transducing a CAR into the immune cell, (c) transfecting a mRNA encoding an anti-TCR CAR into the CAR+ immune cell to achieve a transient expression of the anti-TCR CAR on the cell surface, thus, for a limited time of about 1 to about 11 days the phenotype of these cells is anti-TCR CAR+); following transient expression of the mRNA, the phenotype of the cell returns to CAR+, anti-TCR-CAR-cells; (d) optionally, expanding the CAR+ cells obtained from step (c); and (e) subsequently to the step (c), or (d), the CAR+ cells are directly administered to the patient or otherwise cryopreserved.

In one embodiment, the method, for inducing a population of CAR+ TCR− immune cells, comprises: (a) providing the cell; (b) transfecting the mRNA encoding anti-TCR CAR into the cell to achieve the transient expression of the anti-TCR CAR on the cell surface; (c) transducing the CAR into the cell obtained by step (b); (d) optionally, expanding the CAR+ cell; and (e) subsequently to the step (c), or (d), the CAR+ cells are directly administered to the patient or otherwise cryopreserved.

In another embodiment, following step (b) of introducing the anti-TCR CAR encoding mRNA, the cells transiently express the antigen target of the CAR on the cell surface for a duration in the range of about 1 to about 11 days before being administered to the patient or otherwise cryopreserved.

In one embodiment, the antigen binding domain of the CAR binds to CD123, CD19, CS1, CD38, CLL1, hsp70, CD22, ROR1, EGFRvIII, BCMA, CD33, FLT3, CD70, WT1, MUC16, PRAME, TSPAN10, ROR1, GD3, CT83, mesothelin.

In one embodiment, the antigen binding domain of the CAR binds to an antigen expressed on pathological T cells, CS1, and the mRNA encodes an anti-TCR CAR and a rare cutting endonuclease targeting CS1.

In one embodiment, the antigen binding domain of the CAR binds to an antigen expressed on pathological T cells, CD38, and the mRNA encodes an anti-TCR CAR and a rare cutting endonuclease targeting CD38.

In one embodiment, the antigen binding domain of the CAR binds to any cluster of differentiation molecules selected from CD16, CD19, CD20, CD22, CD30, CD40, CD64, CD78, CD96, CLL1, CD116, CD117, CD71, CD45, CD123 and CD138), a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD20, CD40, disialoganglioside GD2, ductal-epithelial mucine, gp36, TAG-72, glycosphingolipids, glioma-associated antigen, β-human chorionic gonadotropin, alphafetoprotein (AFP), lectin-reactive AFP, thyroglobulin, RAGE-1, MN-CA IX, human telomerase reverse transcriptase, RUI, RU2 (AS), intestinal carboxyl esterase, mut hsp70-2, M-CSF, prostate specific antigen (PSA), PAP, NY-ESO-1, LAGA-Ia, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, RORI, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), GM-CSF, cytokine receptors, endoglin, a major histocompatibility complex (MHC) molecule, BCMA (CD269, TNFRSF 17), or a virus-specific surface antigen such as an HIV specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface markers. Antigens are not necessarily surface marker antigens but can be also endogenous small antigens presented by HLA class I at the surface of the cells.

By way of example, the present invention encompasses single-chain CARs which target specifically a cell surface marker, such as CD38, CS1, together with an inactivation of the genes encoding respectively CD38, CS1 and/or CD70 in the cells expressing said CARs.

By way of example, the present invention encompasses single-chain CARs which target specifically a cell surface marker, such as CD38, HSP70, CD30, FAP, HER2 CD79a or CD79b, CD123, CD22, CLL-1, MUC-1 GD2, O acetyl GD2, CS1 or CD70.

By way of example, the present invention encompasses single-chain CARs which target specifically a cell surface marker, such as BCMA-CD33-EGFRVIII-Flt3-WT1-CD70, MUC16-PRAME-TSPAN10, CLAUDIN18.2-DLL3-LY6G6D, Liv-1-CHRNA2-ADAM10.

Multi-chain CARs may in particular be derived from FεERI. In this architecture, the high affinity IgE binding domain of FεERI alpha chain is replaced by an extracellular ligand-binding domain such as scFv to redirect T cell specificity against cell targets and the N and/or C-termini tails of FεERI beta chain are used to place costimulatory signals in normal juxtamembrane positions.

Multi-chain CARs may in particular comprise at least two of the following components:
a) one polypeptide comprising the transmembrane domain of FεERI alpha chain and an extracellular ligand-binding domain,
b) one polypeptide comprising a part of N- and C-terminal cytoplasmic tail and the transmembrane domain of FεERI beta chain and/or
c) at least two polypeptides comprising each a part of intracytoplasmic tail and the transmembrane domain of FεERI gamma chain, whereby different polypeptides multimerize together spontaneously to form a dimeric, trimeric or tetrameric CAR.

According to such architectures, ligand binding domains and signaling domains are borne on separate polypeptides. The different polypeptides are anchored into the membrane in a close proximity allowing interactions with each other. In such architectures, the signaling and costimulatory domains can be in juxtamembrane positions (i.e. adjacent to the cell membrane on its internal side), which is deemed to allow improved function of co-stimulatory domains. The multi-subunit architecture also offers more flexibility and possibilities of designing CARs with more control on T cell activation. For instance, it is possible to include several extracellular antigen recognition domains having different specificity to obtain a multi-specific CAR architecture.

It is also possible to control the relative ratio between the different subunits in a multi-chain CAR. This type of architecture is described in document WO 2014/039523, which is incorporated herein by reference.

The assembly of the different chains as part of a single multi-chain CAR is made possible, for instance, by using the different alpha, beta and gamma chains of the high affinity receptor for IgE (FεERI) to which the signaling and co-stimulatory domains are fused. The gamma chain comprises a transmembrane region and cytoplasmic tail containing one immunoreceptor tyrosine-based activation motif (ITAM).

The multi-chain CAR can comprise several extracellular ligand-binding domains, to simultaneously bind different elements in a target thereby augmenting immune cell activation and function. In some embodiments, the extracellular ligand-binding domains can be placed in tandem on the same transmembrane polypeptide, and optionally can be separated by a linker. In other embodiments, said different extracellular ligand-binding domains can be placed on different transmembrane polypeptides composing the multi-chain CAR.

The cells may express multi-chain CARs comprising different extracellular ligand binding domains. In particular embodiments, they may express at least a part of FεERI beta and/or gamma chain fused to a signal-transducing domain and several parts of FcERI alpha chains fused to different extracellular ligand binding domains on their surface. In other embodiments, they may express a FεERI beta and/or gamma chain fused to a signal-transducing domain and several FεERI alpha chains fused to different extracellular ligand binding domains.

Thus, two, three, four, five, six or more multi-chain CARs, each one comprising different extracellular ligand binding domains, may be expressed in the cells, so as to preferably simultaneously bind different elements in a target, thereby augmenting immune cell activation and function.

As a preferred embodiment of the invention, polynucleotides encoding the endonucleases of the present invention or the mRNA encoding an anti-TCR CAR of the invention are transfected under a mRNA form by electroporation in order to obtain a transient expression and avoid chromosomal integration of foreign DNA. The inventors have determined different optimal conditions for mRNA electroporation in primary cell. The inventor used the cytoPulse technology which allows, by the use of pulsed electric fields, to transiently permeabilize living cells for delivery of material into the cells (U.S. Pat. No. 6,010,613 and WO 2004/083379). Pulse duration, intensity as well as the interval between pulses can be modified in order to reach the best conditions for high transfection efficiency in primary cells with minimal mortality. Generally, the first high electric field pulses allow pore formation, while subsequent lower electric field pulses allow to moving the polynucleotide into the cell.

In one aspect of the present invention, the inventor describes the steps that led to achievement of >95% transfection efficiency of mRNA in T cells, and the use of the electroporation protocol to transiently express different kind of proteins in T cells. In particular the invention relates to a method of transforming T cell comprising contacting said T cell with an RNA and applying to T cell an agile pulse sequence consisting of:
one electrical pulse with a voltage range from 500 to 3000 V per centimeter, preferably 800 V/cm, a pulse width of 0.1 ms and a pulse interval of 0.2 to 10 ms between the electrical pulses of step (a) and (b);
one electrical pulse with a voltage range from 500 to 3000 V per centimeter, preferably 800 V, with a pulse width of 100 ms and a pulse interval of 100 ms between the electrical pulse of step (b) and the first electrical pulse of step (c); and
4 electrical pulses with a voltage of 150-325V, preferably 130 V with a pulse width of 0.2 ms and a pulse interval of 2 ms between each of 4 electrical pulses.

In a preferred embodiment, primary cells are transfected 4 to 5 days after activation, for example 5×106 cells are transfected with 10 μg of each mRNA encoding left and right arms of TALEN.

In particular embodiments, the method of transforming T cell comprising contacting said T cell with RNA and applying to T cell an agile pulse sequence consisting of:
(a) one electrical pulse with a voltage of 500, 600, 700, 800, 900, 1000, 1200, 1400, 1800, 2000, 2250, 2300, 2350, 2400, 2450, 2500, 2550, 2400, 2450, 2500, 2600, 2700, 2800, 2900 or 3000V per centimeter, a pulse width of 0.1 ms and a pulse interval of 0.2, 0.5, 1, 2, 3, 4, 5, 6, 7, 8, 9 or 10 ms between the electrical pulses of step (a) and (b);
(b) one electrical pulse with a voltage range of 500, 600, 700, 800, 900, 1000, 1200, 1400, 1800, 2000, 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and
(c) 4 electrical pulses with a voltage of 50, 100, 110, 120, 130, 140, 150, 160, 170, 180, 190, 200, 220, 250, 300, 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

The following electroporation process is provided here

|  | Group 1 | Group 2 | Group 3 | unit |
|---|---|---|---|---|
| Amplitude | 800 | 800 | 130 | V |
| Duration | 0.1 | 0.1 | 0.2 | ms |
| Interval | 0.2 | 100 | 2 | ms |
| Number | 1 | 1 | 4 | |

In one embodiment, the transfection of an exogenous polynucleotide, such as an mRNA encoding the anti-TCR CAR is performed by electroporation.

In one embodiment, the transient expression of the mRNA encoding the antigen target of the CAR on the cell surface lasts between about 1 and 11 days, preferably between about 2 and 5 days, and more preferably for about more than 2 days.

In one embodiment, a range between 0.5 μg and 1 μg of mRNA encoding the antigen target of the CAR is transfected into from $10^{\times 4}$ to $10^{\times 10}$ immune cells.

The method of the present invention further comprises a step of incubation, wherein the cells comprising between 90% and 0.00001% of TCR-positive cells (such as alpha beta TCR positive cells) are incubated in the presence of immune cells expressing an anti-TCR CAR of the invention that binds to alpha beta TCR-positive cells, or selectively to alpha beta TCR expressing cells, to CD3 expressing cells, to the alpha TCR expressing cells, to the beta TCR expressing cells, or to an antigen of the alpha betaTCR expressed at the cell surface.

In one embodiment, dosing the mRNA encoding the anti-TCR CAR determines the rate and magnitude of proliferation and activation of the anti-TCR CAR+ immune cells. Thus, the method for autoactivating anti-TCR CAR+ immune cell includes a determination of the optimal level of autoactivation of the anti-TCR CAR+ immune cells. The method comprises the steps of (a) applying a dose between 0.5 μg and 1 μg of mRNA encoding the anti-TCR CAR; (b) determining the yield of activated anti-TCR CAR+ immune cells for each dose of the mRNA used in (a) for transfection; and (c) selecting the dose of mRNA capable of producing the highest yield of autoactivated CAR+ cells obtained from (b).

In one embodiment, the method for autoactivating CAR+ immune cells in addition to the introduction of the anti-TCR CAR-encoding mRNA further includes inactivation of at least one gene involved as an immune checkpoint such as PD1, PDL1 ligand or CTLA-4, this additional step is performed subsequently to step (a) and before step (d).

The at least one additional gene disrupted in TRAC KO CAR+ T cells, may be one of the gene including, but not limited to Programmed Death 1 (PD-1, also known as PDCD1 or CD279, GENBANK accession number: NM_005018), Cytotoxic T-Lymphocyte Antigen 4 (CTLA-4, also known as CD152, GENBANK accession number AF414120.1), LAG3 (also known as CD223, GENBANK accession number: NM_002286.5), Tim3 (also known as HAVCR2, GENBANK accession number: JX049979.1), BTLA (also known as CD272, GENBANK accession number: NM_181780.3), BY55 (also known as CD160, GENBANK accession number: CR541888.1), TIGIT (also known as VSTM3, GENBANK accession number:

NM_173799), B7H5 (also known as C10orf54, homolog of mouse vista gene, GENBANK accession number: NM_022153.1), LAIR1 (also known as CD305, GENBANK accession number: CR542051.1), SIGLEC10 (GENBANK accession number: AY358337.1), 2B4 (also known as CD244, GENBANK accession number: NM_001166664.1), which directly inhibit immune cells.

In particular embodiments, a disruption step of the method according to the present invention relies on the inactivation of one additional gene, (in addition to the TRAC gene), preferably two genes selected from the group consisting of PD1, CTLA-4, LAG3, Tim3, BTLA, BY55, TIGIT, B7H5, LAIR1, SIGLEC10, 2B4, and TCR beta 1 and TCR beta 2. In some embodiments, the genetic modification step of the method relies on the inactivation of two genes selected from the group consisting of PD1 and TCR alpha, PD1 and TCR beta, CTLA-4 and TCR alpha, CTLA-4 and TCR beta, LAG3 and TCR alpha, LAG3 and TCR beta, Tim3 and TCR alpha, Tim3 and TCR beta, BTLA and TCR alpha, BTLA and TCR beta, BY55 and TCR alpha, BY55 and TCR beta, TIGIT and TCR alpha, TIGIT and TCR beta, B7H5 and TCR alpha, B7H5 and TCR beta, LAIR1 and TCR alpha, LAIR1 and TCR beta, SIGLEC10 and TCR alpha, SIGLEC10 and TCR beta, 2B4 and TCR alpha, 2B4 and TCR beta. In another embodiment, the genetic modification step of the method relies on the inactivation of more than two genes. The genetic modification is preferably operated ex-vivo.

Table 1 below, without being exhaustive, show genes which are genes that can be inactivated or over expressed according to the teaching of the present invention in order to improve the efficiency and fitness of the engineered TCR-negative T-cells.

The immune checkpoints gene are preferably selected from such genes having identity to those listed in this table involved into co-inhibitory receptor function, cell death, cytokine signaling, arginine tryptophan starvation, TCR signaling, Induced T-reg repression, transcription factors controlling exhaustion or anergy, and hypoxia mediated tolerance. In a human system the edited genes are human edited genes.

TABLE 1

Genes that make allogeneic TCR-negative T cells more active for immunotherapy when engineered (KO, inactivated, overexpressed . . .) according to the present invention.

| Pathway | Genes that can be inactivated in pathway | NCBI database gene ID (*Homo sapiens*) on May 13th, 2014 |
|---|---|---|
| Co-inhibitory receptors | LAG3 (CD223) | 3902 |
| | HAVCR2 (TIM3) | 84868 |
| | BTLA (CD272) | 151888 |
| | CD160 (NK1) | 11126 |
| | TIGIT (VSIG9) | 201633 |
| | CD96 (TACTILE) | 10225 |
| | CRTAM (CD355) | 56253 |
| | LAIR1 (CD305) | 3903 |
| | SIGLEC7 (CD328) | 27036 |
| | A2A (IGKV2-29) | 28882 |
| | SIGLEC9 (CD329) | 27180 |
| | CD244 (2B4)) | 51744 |
| Cell death | TNFRSF10B (CD262) | 8795 |
| | TNFRSF10A (CD261) | 8797 |
| | CASP3 | 836 |
| | CASP6 | 839 |
| | CASP7 | 840 |
| | CASP8 | 841 |
| | CASP10 | 843 |

TABLE 1-continued

Genes that make allogeneic TCR-negative T cells more active for immunotherapy when engineered (KO, inactivated, overexpressed . . .) according to the present invention.

| Pathway | Genes that can be inactivated in pathway | NCBI database gene ID (*Homo sapiens*) on May 13th, 2014 |
|---|---|---|
| | Arhgap5 (GFI2) | 394 |
| | Akap8i | 10270 |
| | FADD (GIG3) | 8772 |
| | FAS (RP11) | 355 |
| | Stk17b (DRAK2) | 9262 |
| Cytokine signalling | TGFBRII (AAT3) | 7048 |
| | TGFBRI | 7046 |
| | SMAD2 (JV18) | 4087 |
| | SMAD3 | 4088 |
| | SMAD4 | 4089 |
| | SMAD10 (SMAD7) | 394331 |
| | SKI (SGS) | 6497 |
| | SKIL (SNO) | 6498 |
| | TGIF1 (HPE4) | 7050 |
| | IL10RA (CD210) | 3587 |
| | IL10RB | 3588 |
| | HMOX2 (HO-2) | 3163 |
| | Jun (AP1) | 3725 |
| | Ppp3cc | 5533 |
| | Ppm1g | 5496 |
| | Socs1 | 8651 |
| | Soc3 | 9021 |
| | IL6R (CD126) | 3570 |
| | IL6ST (CD130) | 3572 |
| | Lck | 3932 |
| | Fyn | 2534 |
| | ADAP (FYB) | 2533 |
| | Carma1 (CARD11) | 84433 |
| | Bcl10 | 8915 |
| | Malt1 (IMD12) | 10892 |
| | TAK1 (NR2C2) | 7182 |
| arginine/tryptophan starvation | EIF2AK4 (GCN2) | 440275 |
| | Nuak2 | 81788 |
| TCR signalling | CSK | 1445 |
| | PAG1 (CBP) | 55824 |
| | SIT1 | 27240 |
| | CRTAM (CD355) | 56253 |
| | Egr2 (AT591) | 1959 |
| | DGK-a (DAGK) | 1606 |
| | DGK-z | 8525 |
| | Cblb | 868 |
| | Inpp5b | 3633 |
| | Ptpn2 (PTN2) | 5771 |
| | Vamp7 | 6845 |
| | Mast2 | 23139 |
| | tnk1 | 8711 |
| | stk17b (DRAK2) | 9262 |
| | Mdfic (HIC) | 29969 |
| | F11r (CD321) | 50848 |
| Induced Treg | FOXP3 (JM2) | 50943 |
| | Entpd1 (CD39) | 953 |
| Transcription factors controlling exhaustion/anergy | PRDM1 (blimp1) | 12142 |
| | BATF | 10538 |
| | Ypel2 | 388403 |
| | Ppp2r2d | 55844 |
| | Rock1 | 6093 |
| | Sbf1 | 6305 |
| | Hipk1 (MYAK) | 204851 |
| | Map3k3 | 4215 |
| | Grk6 | 2870 |
| | Eif2ak3 (PEK) | 9451 |
| | Fyn | 2534 |
| | NFAT1 (NFATC2) | 4773 |
| Hypoxia mediated tolerance | GUCY1A2 | 2977 |
| | GUCY1A3 | 2982 |
| | GUCY1B2 | 2974 |
| | GUCY1B3 | 2983 |

In particular embodiments, TCR-negative engineered T cells are provided said engineered cells express a CAR and comprises at least one genetic modification to reduce or inactivate the expression of at least one endogenous polynucleotide sequence selected from:
  a) polynucleotide sequence(s), which transcription and/or translation is (are) involved into reduction of glycolysis and calcium signaling in response to a low glucose condition, such as SERCA3 to increase calcium signaling, miR101 and mir26A to increase glycolysis, BCAT to mobilize glycolytic reserves; and/or
  b) polynucleotide sequence(s), which expression up regulate(s) immune checkpoint proteins (e.g. TIM3, CEACAM, LAG3, TIGIT) expression, such as IL27RA, STAT1, STAT3; and/or
  c) polynucleotide sequence(s), which expression mediate(s) interaction with HLA-G, such as ILT2 or ILT4; and/or
  d) polynucleotide sequence(s), which expression is(are) involved into the down regulation of T-cell proliferation such as SEMA7A, SHARPIN to reduce Treg proliferation, STAT1 to lower apoptosis, PEA15 to increase IL-2 secretion and RICTOR to favor CD8 memory differentiation; and/or
  e) polynucleotide sequence(s), which expression is (are) involved into the down regulation of T-cell activation, such as mir21; and/or
  f) polynucleotide sequence(s), which expression is (are) involved in signaling pathways responding to cytokines, such as JAK2 and AURKA; and/or
  g) polynucleotide sequence(s), which expression is (are) involved in T-cell exhaustion, such as DNMT3, miRNA31, MT1A, MT2A, PTGER2.

In particular embodiments, said TCR-negative engineered immune T cell express a chimeric antigen receptor (CAR) inserted into the TRAC gene and comprises a genetic modification reducing or inactivating the expression of a microRNA genomic sequence, more particularly said microRNA genomic sequences are selected from miR21, mir26A and miR101.

In particular embodiments, said engineered cell express a chimeric antigen receptor (CAR) inserted into the TRAC gene and comprises a genetic modification making cells resistant to a drug and/or hypersensitive to a (another) drug.

In one embodiment, the method of the invention in addition to the introduction of the anti-TCR CAR mRNA further includes inactivation of at least one gene involved in drug resistance such as deoxycytidine kinase (dCk), hypoxanthine guanine phosphoribosyl transferase (HPRT), glucocorticoid receptor (GR) and CD52.

In one embodiment, the method of the invention in addition to the introduction of the anti-TCR CAR further includes inactivation of at least one gene involved in drug hypersensitivity, such the genes encoding GGH, RhoA, CDK5, CXCR3, NR1H2, URG4, PARP14, AMPD3, CCDC38, NFU1 and CACNG5 protein.

In one embodiment, the method of the invention in addition to the introduction of the anti-TCR CAR mRNA further includes an ON or OFF switch system which allows the modulation of the activity of the CAR expressing cell, the switch system is selected from the group consisting of epitope tagging, drug resistance, drug hypersensitivity; and CD52 inactivation combined to alemtuzumab selection.

In one embodiment, the anti-TCR CAR comprises an epitope-tagging domain, which can be bound by a monoclonal antibody in order to deplete the immune cells, in case of an adverse reaction.

In one embodiment, the anti-TCR CAR is a single-chain CAR (scCAR). The ssCAR has one of the following polypeptide structure The ssCAR comprises (a) an extra cellular ligand binding-domain comprising a VH and a VL from a monoclonal antibody directed against a TCR, a TCR subunit of a TCR associated protein, such as CD3; (b) a hinge chosen from the group consisting of CD8α, FcERIII gamma and IgG1; (c) a CD8a transmembrane domain; (d) a cytoplasmic domain including a CD3ζ signaling domain; and (e) a 4-1BB co-stimulatory domain.

The present invention relates to pharmaceutical compositions comprising at least one population temporarily expressing an anti-TCR CAR⁺ T cells.

The present invention relates to pharmaceutical compositions for use in the treatment of cancer, infection or immune disease.

It is contemplated a genetically modified cell comprising a plurality of CARs transiently co-expressed with an mRNA, wherein each CAR comprises a different antigen binding domain against a TCR antigen, a transmembrane domain, and an intracellular domain of a costimulatory molecule.

In one embodiment, the stability and the translational efficiency of the antigen-encoded mRNA in transiently transfected cells can be monitored by expansion or contraction of the adenosine bases, the poly(A) tail. In one embodiment, the nucleic acid sequence of the mRNA comprises a poly(A) tail comprising about 50. to 5000 adenosine bases (A), preferably 120 A.

In one embodiment, the nucleic acid sequence of the mRNA comprises a 3'UTR comprising at least one repeat of a 3'UTR derived from the human beta-globulin. In one embodiment, the mRNA includes one or more tandem copies of the b-globin 3'UTR as this element increased both mRNA and translation efficiency (Holtkamp, Blood, 2006, 108:4009-4017).

In one embodiment, the costimulatory molecule of the CAR is selected from the group consisting of CD27, CD28, 4-1BB, OX40, CD30, CD40, PD-1, lymphocyte function-associated antigen-1 (LFA-1), CD2, CD7, LIGHT, NKG2C, B7-H3, a ligand that specifically binds with CD83, and any combination thereof.

In one embodiment, the tumor antigen is an antigen associated with a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

The results presented herein demonstrate that administration of a TCR-negative CAR T cell of the present invention has lytic activity against a tumor isolated from patients. Thus, in one embodiment, the compositions of the present invention serve as a cellular therapy against a cancer or tumor.

The invention additionally includes a method of treating a human with cancer. The method comprises administering to a human an effective amount of a TCR negative CAR+ T cells obtained according to the present invention with undetectable level of TCR, preferably undetectable level by FACS analysis.

Thus, it is clear that the present invention provides a method to enrich a population of TCR-negative CAR+ expressing immune cells with (a) temporal control of cellular activation by degradation of the introduced mRNA encoding an anti-TCR CAR; (b) reversibility of the autoactivated anti-TCR CAR phenotype cells to the original phenotype anti-TC CAR⁻, and (c) limited potential for toxic side effects due to the persistence of highly activated CAR⁺ cells.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

The articles "a" and "an" are used herein to refer to one or to plurality (i.e., to at least one) of the grammatical object of the article. By way of example, "an element" means one element or plurality element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are often of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," or "VH" as used herein, refers to the larger of the two types of polypeptide chains present in all antibody molecules in their naturally occurring conformations.

An "antibody light chain," or "VL" as used herein, refers to the smaller of the two types of polypeptide chains present in all antibody molecules in their naturally occurring conformations. K and λ light chains refer to the two major antibody light chain isotypes.

The term "antigen" or "Ag" as used herein is defined as a molecule that provokes an immune response. This immune response may involve either antibody production, or the activation of specific immunologically competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of one, or more than one, gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

T cells and Activated T cells (include that this means CD3⁺ cells): T cells (also referred to as T lymphocytes)

belong to a group of white blood cells referred to as lymphocytes. Lymphocytes generally are involved in cell-mediated immunity. The "T" in "T cells" refers to cells derived from or whose maturation is influenced by the thymus. T cells can be distinguished from other lymphocytes types such as B cells and Natural Killer (NK) cells by the presence of cell surface proteins known as T cell receptors. The term "activated T cells" as used herein, refers to T cells that have been stimulated to produce an immune response (e.g., clonal expansion of activated T cells) by recognition of an antigenic determinant presented in the context of a Class II major histocompatibility (MHC) marker. T-cells are activated by the presence of an antigenic determinant, cytokines and/or lymphokines and cluster of differentiation cell surface proteins (e.g., CD3, CD4, CD8, the like and combinations thereof). Cells that express a cluster of differential protein often are said to be "positive" for expression of that protein on the surface of T-cells (e.g., cells positive for CD3 or CD 4 expression are referred to as CD3$^+$ or CD4$^+$). CD3 and CD4 proteins are cell surface receptors or co-receptors that may be directly and/or indirectly involved in signal transduction in T cells.

By "chimeric antigen receptor" or "CAR" is meant, for example, a chimeric polypeptide which comprises a polypeptide sequence that recognizes a target antigen (an antigen-recognition domain) linked to a transmembrane polypeptide and intracellular domain polypeptide selected to activate the T cell and provide specific immunity. Most commonly, the binding domain is derived from a Fab antibody fragment that has been fashioned into a single chain scFv via the introduction of a flexible linker between the antibody chains within the specificity domain. Other possible specificity domains can include the signaling portions of hormone or cytokine molecules, the extracellular domains of receptors, and peptide ligands or peptides isolated by library (e.g. phage) screening (see Ramos and Dotti, (2011) *Expert Opin Bio Ther* 11(7): 855). Flexibility between the signaling and the binding portions of the CAR may be a desirable characteristic to allow for more optimum interaction between the target and the binding domain, so often a hinge region is included. One example of a structure that can be used is the CH2-CH3 region from an immunoglobulin such as an IgG molecule. The signaling domain of the typical CAR comprises intracellular domains of the TCR-CD3 complex such as the zeta chain. Alternatively, the γ chain of an Fc receptor may be used. The transmembrane portion of the typical CAR can comprise transmembrane portions of proteins such as CD4, CD8 or CD28 (Ramos and Dotti, ibid). Characteristics of some CARs include their ability to redirect T-cell specificity and reactivity toward a selected target in a non-MHC-restricted manner. The non-MHC-restricted target recognition gives T-cells expressing CARs the ability to recognize a target independent of antigen processing, thus bypassing a major mechanism of tumor escape.

The "first generation" CARs often comprise a single internal signaling domain such as the CD3 zeta chain, however, they are somewhat ineffectual in the clinic, perhaps due to incomplete activation. To increase performance of T-cells bearing these CARs, second generation CARs have been generated with the ability of proving the T-cell additional activation signals by including another stimulatory domain, often derived from the intercellular domains of other receptors such as CD28, CD134/OX40, CD137/4-1BB, Lck, ICOS and DAP10. Additionally, third generation CARs have also been developed wherein the CAR contains three or more stimulatory domains (Ramos and Dotti, ibid).

In some instances, CAR can comprise an extracellular hinge domain, transmembrane domain, and optionally, an intracellular hinge domain comprising CD8 and an intracellular T-cell receptor signaling domain comprising CD28; 4-1BB, and CD3zeta. CD28 is a T-cell marker important in T-cell co-stimulation. CD8 is also a T-cell marker. 4-1BB transmits a potent costimulatory signal to T-cells, promoting differentiation and enhancing long-term survival of T lymphocytes. CD3zeta associates with TCRs to produce a signal and contains immunoreceptor tyrosine-based activation motifs (ITAMs). In other instances, CARs can comprise an extracellular hinge domain, transmembrane domain, and intracellular T-cell signaling domain comprising CD28 and CD3zeta. In further instances, CARs can comprise an extracellular hinge domain and transmembrane domain comprising CD8 and an intracellular T-cell receptor signaling domain comprising CD28 and CD3zeta.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "donor T cell" as used here refers to T cells that often are administered to a recipient to confer anti-viral and/or anti-tumor immunity following allogeneic stem cell transplantation. Donor T cells often are utilized to inhibit marrow graft rejection and increase the success of alloengraftment, however the same donor T cells can cause an alloaggressive response against host antigens, which in turn can result in graft versus host disease (GVHD). Certain activated donor T cells can cause a higher or lower GvHD response than other activated T cells. Donor T cells may also be reactive against recipient tumor cells, causing a beneficial graft vs. tumor effect.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced to an organism, cell, tissue or system that was produced outside an organism, cell, tissue or system.

The term "expression" as used herein is defined as the transcription and/or translation of a particular nucleotide sequence.

"Engineered cells" refers herein to cells having been engineered, e.g. by the introduction of an exogenous nucleic acid sequence or specific alteration of an endogenous gene sequence. An exogenous nucleic acid sequence that is introduced may comprise a wild type sequence of any species that may be modified. An engineered cell may comprise genetic modifications such as one or more mutations, insertions and/or deletions in an endogenous gene and/or insertion of an exogenous nucleic acid (e.g. a genetic construct) in the genome. An engineered cell may refer to a cell in isolation or in culture. Engineered cells may be "transduced cells" wherein the cells have been infected with e.g. an engineered virus. For example, a retroviral vector may be used, such as described in the examples, but other suitable viral vectors may also be contemplated such as lentiviruses. Non-viral methods may also be used, such as transfections or electroporation of DNA vectors. DNA vectors that may be used are transposon vectors. Engineered cells may thus also be "stably transfected cells" or "transiently transfected cells". Transfection refers to non-viral methods to transfer DNA (or RNA) to cells such that a gene is expressed. Transfection methods are widely known in the art, such as calcium phosphate transfection, PEG transfection, and liposomal or lipoplex transfection of nucleic acids. Such a transfection may be transient but may also be a stable transfection wherein cells can be selected that have the gene construct integrated in their genome.

The term "hyperproliferative disease" is defined as a disease that results from a hyperproliferation of cells. Exemplary hyperproliferative diseases include, but are not limited to, cancer or autoimmune diseases. Other hyperproliferative diseases may include vascular occlusion, restenosis, atherosclerosis, or inflammatory bowel disease.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some versions contain an intron(s).

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

Leader sequences may be added to enhance the stability of mRNA and result in more efficient translation. The leader sequence is usually involved in targeting the mRNA to the endoplasmic reticulum. Examples include the signal sequence for the HIV-1 envelope glycoprotein (Env), which delays its own cleavage, and the IgE gene leader sequence (Kutzler, M. A., and Weiner, D. B., 2008. Nature Rev. Gen. 9:776-88; Li, V., et al., 2000. Virology 272:417-28; Xu, Z. L., et al. 2001. Gene 272:149-56; Malin, A. S., et al., 2000. Microbes Infect. 2:1677-85; Kutzler, M. A., et al., 2005. J. Immunol. 175:112-125; Yang, J. S., et al., 2002. Emerg. Infect. Dis. 8:1379-84; Kumar, S., et al., 2006. DNA Cell Biol. 25:383-92; Wang, S., et al., 2006. Vaccine 24:4531-40). The IgE leader may be used to enhance insertion into the endoplasmic reticulum (Tepler, I, et al. (1989) J. Biol. Chem. 264:5912).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

AAV refers to viral particle derived from adeno associated virus, preferred are AAV6 as described in WO2017053729 A1 or in PA2017 70240.

Natural Killer cells (NK cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation. NK cells do not express T-cell antigen receptors (TCR) or Pan T marker CD3 or surface immunoglobulins (Ig) B cell receptors, but they usually express the surface markers CD16 (FCYRI I I) and CD56 in humans, NK1.1 or NK1.2 in C57BL/6 mice. Up to 80% of human NK cells also express CD8.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

Immunological checkpoint are molecules expressed by the immune system that either turn up a signal (co-stimulatory molecules) or turn down a signal usually essential in the immune response against an antigen. Many cancers protect themselves from the immune system by inhibiting the T cell signal.

Immune checkpoints genes may lead T-cell stimulation towards T-cell inhibition. PD1, short for programmed death receptor, and CTLA-4, short for cytotoxic T-lymphocyte-associated protein 4 and also called CD152, are for example two major key players. Upon T-cell activation, PDCD1 expression is induced in T-cells. The ligands for the PD1 receptor are PD1 ligand (PDL1 also known as B7-H1 and CD272) and PDL2 (also known as B7-DC and CD273), and are normally expressed in antigen presenting cells. PD1-PDL (PD1 ligand) coupling causes deactivation of the T-cell and is involved in inducing T-cell tolerance (see, Pardoll (2012) Nat Rev 12:252). It is thought that PD1 up-regulation is somehow tied to T-cell exhaustion (defined as a progressive loss of key effector functions) when T-cell dysfunction is observed in the presence of chronic antigen exposure as is the case in HIV infection. PD1 may also play a role in tumor-specific escape from immune surveillance. It has been demonstrated that PD1 is highly expressed in tumor-specific cytotoxic T lymphocytes (CTLs) in both chronic myelogenous leukemia (CML) and acute myelogenous leukemia (AML). PD1 is also up-regulated in melanoma infiltrating T lymphocytes (TILs) (see Dotti (2009) Blood 114 (8): 1457-58). Tumors have been found to express the PD1 ligand PD-L1 or, more rarely, the PD1 ligand PDL2 which, when combined with the up-regulation of PD1 in CTLs, may be a contributory factor in the loss in T-cell functionality and the inability of CTLs to mediate an effective anti-tumor response. Researchers have shown that in mice chronically infected with lymphocytic choriomeningitis virus (LCMV), administration of anti-PD1 antibodies blocked PD1-PDL interaction and was able to restore some T-cell functionality (proliferation and cytokine secretion), leading to a decrease in viral load (Barber et al (2006) Nature 439(9): 682-687).

Another immunological checkpoint gene, the CTLA-4 receptor, similar to the T-cell receptor co-stimulator CD28, interacts with the CD80 and CD86 ligands on antigen presenting cells. But while interaction of these antigens with CD28 causes activation of T-cells, interaction of CD80 or CD86 with CTLA-4 antagonizes T-cell activation by interfering with IL-2 secretion and IL-2 receptor expression, and by inhibiting the expression of critical cell cycle components. CTLA-4 is not found on the surface of most resting T-cells, but is up-regulated transiently after T-cell activation. Thus, CTLA-4 is also involved in the balance of activating and inhibiting T-cell activity (see Attia et al. (2005) J Clin Oncol. 23(25): 6043-6053). Initial clinical studies involving the use of CTLA 4 antibodies in subjects with metastatic melanoma found regression of the disease (Attia, ibid), but later studies found that subject treated with the antibodies exhibited side effects of the therapy (immune-related adverse events: rashes, colitis, hepatitis etc.) that seemed to be related to a breaking of self-tolerance. Analysis of this data suggested that greater tumor regression as a result of the anti-CTLA4 antibody correlated directly with a greater severity of immune-related adverse events (Weber (2007) Oncologist 12 (7): 864-872).

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-$\beta$, and/or reorganization of cytoskeletal structures, and the like.

A "stimulatory molecule," as the term is used herein, means a molecule on a T cell that specifically binds with a cognate stimulatory ligand present on an antigen presenting cell.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred to, or introduced into, the host cell. A "transfected" or "transformed" or "transduced" cell is one which has been transfected, transformed or transduced with exogenous nucleic acid. The cell includes the primary subject cell and its progeny.

Tumor infiltrating lymphocytes (TILs) refer to T cells having various receptors which infiltrate tumors and kill tumor cells in a targeted manor. Regulating the activity of the TILs using the methods of the present application would allow for more direct control of the elimination of tumor cells.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

BRIEF DESCRIPTION OF THE DRAWINGS

Embodiments are described herein with reference to the appended drawings, in which.

DETAILED DESCRIPTION OF THE INVENTION

Figure 1:
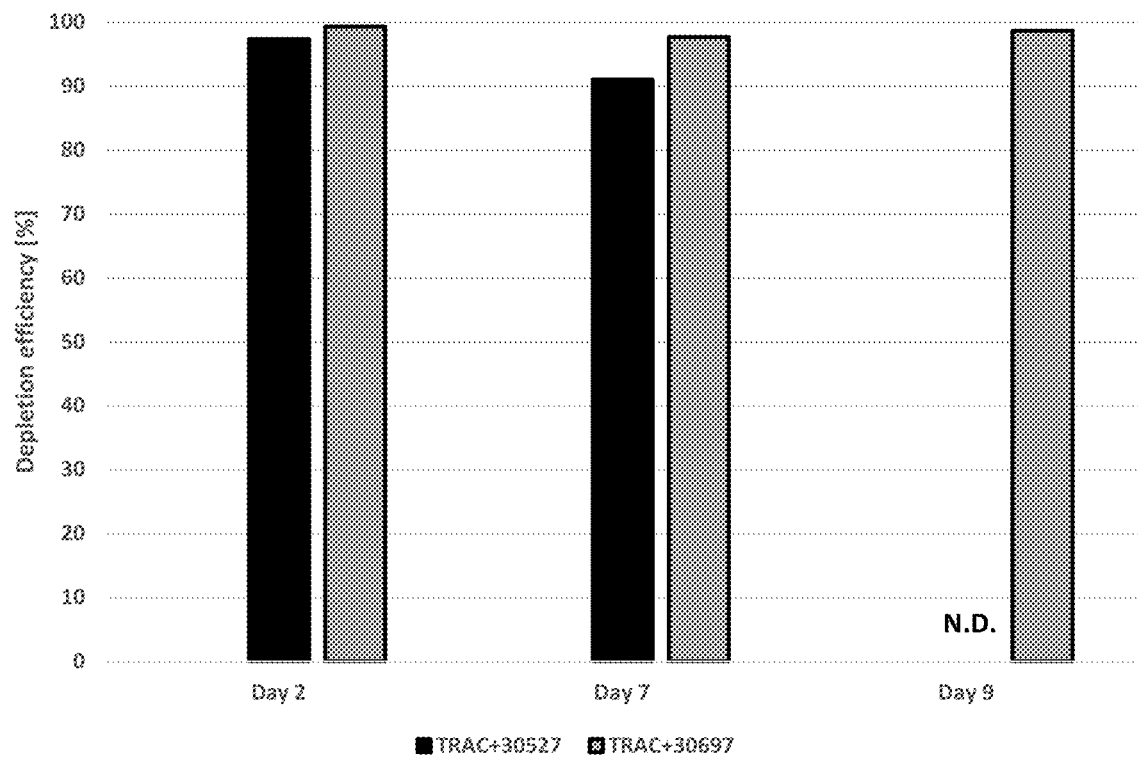
FIG. 1. Depicts the depletion efficiencies calculated after transfection of mRNA encoding an anti-TCR CAR used in the present invention into allogeneic cells comprising less than 10% TCR positive cells. D2 corresponds to an electroporation (EP) of CD3 CAR mRNA at D2 after the TRAC TALEN electroporation, and detection of cell surface expression of the TCR and CD3 by flow cytometry (FACS) performed 4 days after the CD3 CAR electroporation. D7=EP of CD3 CAR mRNA done at D7 after the TRAC TALEN EP, FACS of TCR and CD3 done 3 days after the CD3 CAR EP. D9=EP of CD3 CAR mRNA done at D9 after the TRAC TALEN EP, FACS of TCR and CD3 done 4 days after the CD3 CAR EP FIG. 2. Shows the depletion efficiency (%) using different doses of cells transiently expressing an anti-TCR CAR as compared to cells after TCR gene inhibition using a TALEN specific for the TRAC gene mRNA.

As described herein are new methods and compositions for making TCR-negative CAR⁺ immune cells less detrimental (e.g., tumor lysis syndrome, cytokine storm, off-target toxicity, graft versus host disease, GVHD) but sufficiently enriched in activated CAR⁺ cells before being administered to a patient to be more efficient. The inventors found that the T cell stimulatory capacity of TCR-negative CAR T cells can be greatly enhanced with a transiently expressed mRNA encoding a full length anti-TCR CAR, in particular of SEQ ID NO 12. The anti-TCR CAR-encoding mRNA expression is self-limited. That is, transfecting CAR⁺ immune T cells with the mRNA encoding the anti-TCR CAR for a limited time of about 1 to about 11 days, as presently herein, would allow for purification of TCR-negative CAR+ T cells and activation of the CAR⁺ T cells; following degradation of the anti-TCR CAR mRNA would allow the CAR⁺T-APC cell to return to its original CAR+ phenotype; the CAR⁺ phenotype persist longer. Unexpectedly, in an anti-TCR-CAR encoding mRNA dose-dependent manner, the population of the CAR⁺ T cells were enriched. As observed by the inventors, the enrichment of the CAR⁺ T cells was accompanied with an improved antitumor activity in vitro and less side effects An advantage of the present method is that there is no requirement to expand the CAR⁺ immune cells to support T cell proliferation and survival, which is in contrast to most studies reporting in vitro stimulations. Typically, subsequently to the step for introducing the CAR into the T cell by transduction, lentiviral transduction transduction AAV6 or electroporation, the T cells are expanded by cytokine treatment. By omitting exogenous cytokines, the CAR+ T cells are less activated. Another advantage is that there is no requirement to purify the CAR⁺ immune cells before being administered to a patient in needed thereof.

The cells may be T cells; tumor infiltrating T cells; natural killer-type T cells (NK-T), including CD56⁺ T cells and CD57⁺ T cells; TCR-expressing cells. T-cells include, but are not limited to, helper T-cells (e.g., CD4+ cells), cytotoxic T-cells (e.g., CD8+), memory T-cells, regulatory T-cells, tumor infiltrating lymphocytes (TILs, CD3+) and the like.

The engineered genetically modified cells included in the present invention are natural killer (NK) cells (αβTCR$^{negative}$/CD56⁺CD3$^{negative}$), hematopoietic stem cells.

The present invention relates generally to the use of autologous or allogeneic T cells that stably express a CAR, such as with a lentiviral vector or retroviral vector or AAV vector expressing a CAR. It is contemplated using cells RNA-engineered T cells in that the anti-TCR CAR is expressed for a limited time in the cell. It is also contemplated to include cells genetically engineered to stably express a CAR by nucleases such as TALEN®. In this later case the sequence of the CAR is integrated into the genome.

In one embodiment, the method for transiently expressing an anti-TCR CAR comprises:
  (a) providing cells;
  (b) transducing the cells with a CAR which is not an anti-TCR CAR,
  (c) transfecting the mRNA encoding anti-TCR CAR into the immune cell obtained from (b) to achieve transient expression of anti-TCR CAR on the cell surface, thus, for a limited time of about 1 to about 11 days the phenotype of these cells is anti-TCR CAR$^+$ T-following transient expression of the mRNA, the phenotype of the cell returns to CAR$^+$, (CAR+ which is not an anti-TCR CAR)
  (d) optionally, expanding the CAR$^+$ cells obtained from step (c), and
  (e) subsequently to the step (c), or (d), the TCR-negative CAR+ cells are administered to the patient or otherwise cryopreserved.

In another embodiment, the method for inducing a population of CAR$^+$ immune T cells comprises:
  (a) providing the immune T cell;
  (b) transfecting the mRNA encoding the anti-TCR CAR into the immune T cell to achieve transient expression of anti-TCR CAR on the cell surface,
  (c) transducing a CAR which is not an anti-TCR CAR into the immune T cell obtained from (b),
  (d) optionally, expanding the immune T cell,
  (e) subsequently to the step (c), or (d), the immune T cells are administered to the patient or otherwise cryopreserved.

In one embodiment, a range between 0.5 µg and 1 µg of mRNA encoding anti-TCR CAR is transfected into a range between $10^5$ and $10^7$ of immune cells.

In one embodiment, dosing of the mRNA encoding the antigen target of the CAR determines the rate and magnitude of the proliferation and activation of the anti-TCR CAR$^+$ immune cells. Thus, the method for autoactivating CAR$^+$ immune cells includes determining the optimal level of the autoactivation of the anti-TCR CAR$^+$ immune. The method comprises the steps of (a) applying a dose varying between 0.5 µg and 1.0 µg of the mRNA encoding the anti-TCR CAR; (b) determining the yield of autoactivated CAR expressing cell for each dose of the mRNA used in (a) for transfection; and (c) selecting the dose of mRNA capable of producing the highest yield of autoactivated cells from (b).

The inventors have determined a dose dependent for the mRNA encoding the anti-TCR CAR to enrich in TCR-negative CAR$^+$ T cells from the mixed immune cell population used for. In addition, the inventors have observed that the enrichment in the TCR-negative CAR$^+$ T cell population in the presence of the transiently anti-TCR CAR mRNA was greater when the cells were previously transduced at lower doses of lentiviral particles.

In a further experiment, the inventors investigated the effect of the mRNA encoding the anti-TCR CAR on the expression of CD4 and CD8. The results show that the transient expression of the mRNA, on the cell surface, does not change the CD4/CD8 ratio.

In a following experiment, the inventors analyzed whether the transiently expressed anti-TCR mRNA improved antitumor activity. While the results show that the transient expression of the anti-TCR mRNA does not modify the cytolytic activity of the anti-CD123 CAR used in the experiment, it appears that TCR-negative anti-CD123 CAR$^+$ T cells have a slightly improved antitumor activity in vitro.

In one embodiment, the population of autoactivated anti-TCR CAR$^+$ immune cells represent a range between 40% and 99%, preferably between 75% and 95% of the percentage of the total of immune cells, as determined using cell surface marker of T cell activation in anti-TCR CAR expressing cells.

The method of the invention may include additional steps of procuring the T cells from donors other than the recipient, thus, involving an allogeneic treatment. Accordingly, the method of the invention may include additional steps of procuring the T-cells from a donor and to inactivate genes thereof involved in MHC recognition and or being targets of immunosuppressive drugs such as described for instance in WO 2013/176915. T cell receptors (TCR) are cell surface receptors that participate in the activation of T cells in response to the presentation of antigen. The TCR is generally composed of two chains, alpha and beta, which assemble to form a heterodimer and associates with the CD3-transducing subunits to form the T-cell receptor complex present on the cell surface. In contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of Graft-versus-Host-Donor (GvHD) disease. It has been shown that normal surface expression of the TCR depends on the coordinated synthesis and assembly of all seven components of the complex (Ashwell and Klusner 1990). The inactivation of TCR alpha or TCR beta can result in the elimination of the TCR from the surface of T cells preventing recognition of alloantigen and thus GvHD. Mainly, GVHD is linked to the presence of alpha beta TCR. Thus, still according to the invention, engraftment of the TCR-negative CAR+T-cells may be improved by inactivating at least one gene encoding a TCR component. TCR is rendered not functional in the cells by inactivating TCR alpha gene and/or TCR beta gene(s).

It is contemplated that allogeneic cells, including "off-the-shelf" cryopreserved allogeneic engineered CAR$^+$ T cells, can be used with the methods described herein. Hence, it is preferable to further engineer the cells to make them non-alloreactive to ensure their proper engraftment. In one embodiment, the method for autoactivating CAR expressing immune cells as described herein includes inactivation of at least one gene involved in allogeneicity, such as TCR, beta2M or TAP-1; this additional step is performed subsequently to step (a) and before step (d) of the methods described herein. For example, endogenous T cell expression may be suppressed via methods such as e.g. RNAi via shRNA expression, zinc fingers, CRISPR, TALENS, or Meganucleases. The inventors have previously disclosed a method to genetically inactivate genes encoding T cell receptors by using specific TAL-nucleases, better known under the registered trademark TALEN® (Cellectis, 8, rue de la Croix Jarry, 75013 PARIS, FRANCE). This method allows the production of allogeneic T cells (WO 2013/176915). Thus, the autoactivated engineered CAR$^+$ T cells will have most, if not all, of the T cells expressing endogenous alpha beta T cell receptors removed and therefore any risk of endogenous alpha beta T cell receptors causing unwanted targeting may be avoided.

In immunocompetent hosts, allogeneic cells are normally rapidly rejected by the host immune system. It has been demonstrated that, allogeneic leukocytes present in non-irradiated blood products will persist for no more than 5 to 6 days. Thus, to prevent rejection of allogeneic cells, the host's immune system must be effectively suppressed. Glucocorticoid steroids are widely used therapeutically for immunosuppression. This class of steroid hormones binds to the glucocorticoid receptor (GR) present in the cytosol of T cells resulting in the translocation into the nucleus and the binding of specific DNA motifs that regulate the expression of a number of genes involved in the immunologic process. Treatment of T cells with glucocorticoid steroids results in reduced levels of cytokine production leading to T cell anergy and interfering in T cell activation. Alemtuzumab, also known as CAMPATH1-H®, is a humanized monoclonal antibody targeting CD52, a 12 amino acid glycosylphosphatidyl-inositol-(GPI) linked glycoprotein (Waldmann and Hale, 2005). CD52 is expressed at high levels on T and B lymphocytes and lower levels on monocytes while being absent on granulocytes and bone marrow precursors. Treatment with Alemtuzumab, a humanized monoclonal antibody directed against CD52, has been shown to induce a rapid depletion of circulating lymphocytes and monocytes. It is frequently used in the treatment of T cell lymphomas and in certain cases as part of a conditioning regimen for transplantation. However, in the case of adoptive immunotherapy the use of immunosuppressive drugs will also have a detrimental effect on the introduced therapeutic T cells. Therefore, to effectively use an adoptive immunotherapy approach in these conditions, the introduced cells would need to be resistant to the immunosuppressive treatment.

Thus, the methods as described herein for purifying TCR-negative CAR$^+$ immune cells with an anti-TCR mRNA transiently expressed include a step for inactivation of at least one gene involved in the immunosuppressive treatment of the recipient, as previously described by in the inventor in WO2015121454. For example, in one embodiment, in the case the immunosuppressive treatment of the recipient involves the humanized antibody targeting CD52 antigen, then the gene to be inactivated is the endogenous CD52 gene. The step for inactivation of the CD52 is performed subsequently to (a) and before step (d). As another embodiment, in the case the immunosuppressive treatment of the recipient involves a corticosteroid such as dexamethasone, then the gene to be inactivated is a glucocorticoid receptor (GR). The step for inactivation of the endogenous GR gene is performed subsequently to (a) and before step (d). As another embodiment, in the case the immunosuppressive treatment of the recipient involves FK506 also known as Tacrolimus or fujimycin, then the endogenous gene to be inactivated is a FKBP family gene member or a variant thereof. The step for inactivation of the endogenous FKBP family gene is performed subsequently to (a) and before step (d). As another embodiment, in the case the immunosuppressive treatment of the recipient involves cyclosporine, then the endogenous gene to be inactivated is a cyclophilin family gene member or a variant thereof. The step for inactivation of the endogenous cyclophilin family gene is performed subsequently to (a) and before step (d).

It is well documented that some patients acquire a resistance to the chemotherapeutic agents' activity. For example, kinase inhibitors are being used successfully to treat cancers; however, some patients acquire a resistance to the drug's activity (WO2008089388). The inventors have previously developed a method of engineering allogeneic T cells resistant to chemotherapeutic agents (WO2015075195; WO201515867; WO2015140268; WO2016120218). Moreover, drug resistance can also benefit from the ability to selectively expand the engineered T cell thereby avoiding the problems due to inefficient gene transfer to these cells.

In one embodiment, the methods as described herein for purifying TCR-negative CAR$^+$ immune cells with an anti-TCR mRNA transiently expressed as described herein, includes inactivation of at least one gene involved in drug resistance such as deoxycytidine kinase (dCk), hypoxanthine guanine phosphoribosyl transferase (HPRT), glucocorticoid receptor (GR) and CD52. The inactivation step is performed subsequently to step (a) and before step (d) of the methods described herein. For example, knocking out the CD52 gene makes donor T cells resistant to the lymphodepleting agent Alemtuzumab (CAMPATH-1H®). Alemtuzumab is a recombinant humanized IgG1 monoclonal antibody directed against human CD52 (hCD52), a 12 amino acid, 28 kD glycosylated glycosylphophatidylinositol (GPI)-linked cell surface protein (Hale et al., Tissue Antigens 35:118-27 (1990); Hale et at, 2001, supra; Waldmann and Hale 2005). CD52 is a cell surface protein expressed at high levels by both normal and malignant B and T lymphocytes (Hale et al., *J Biol regal Homeost Agents* 15:386-391 (2001); Huh et al., Blood 92: Abstract 4199 (1998); Elsner et al., *Blood* 88:4684-4693 (1996); Gilleece et al., Blood 82:807-812 (1993); Rodig et al., *Clin Cancer Res* 12:7174-7179 (2006); Ginaldi et al., *Leak Res* 22:185-191 (1998)). CD52 is expressed at lower levels by monocytes, macrophages, and eosinophils, with little expression found on mature natural killer (NK) cells, neutrophils, and hematological stem cells. Id. Treatment with Alemtuzumab has been shown to induce a rapid depletion of circulating lymphocytes and monocytes.

According to another aspect, the resistance to drugs can be conferred to a T cell by expressing a drug resistance gene. Variant alleles of several genes such as dihydrofolate reductase (DHFR), inosine monophosphate dehydrogenase 2 (IMPDH2), calcineurin or methylguanine transferase (MGMT) have been identified to confer drug resistance to a cell. For example, the drug resistant gene MGMT encoding human alkyl guanine transferase (hAGT) is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze et al, (1999) J. Pharmacol. Exp. Ther. 290: 1467-1474). P140KMGMT-based drug resistant gene therapy has been shown to confer chemoprotection to mouse, canine, rhesus macaques, and human cells, specifically hematopoetic cells (Zielske et al, (2003) J. Clin. Invest. 112:1561-1570; Pollok et al, (2003) Hum. Gene Ther. 14: 1703-1714; Gerull et al, (2007) Hum. Gene Ther. 18: 451-456; NeffFei a/., (2005) Blood 105:997-1002; Larochelle et al, (2009) J. Clin. Invest. 119: 1952-1963; Sawai et al, (2001) Mol. Ther. 3: 78-87). The step for inactivation for a gene is performed subsequently to step (a) and before step (d) of the methods described herein.

The activation of a T cell endowed with a CAR may be inhibited due to the engagement of immunological checkpoints designed to balance T cell activation with T-cell inhibition. Genes encoding immune checkpoints are known, such as, PDCD1 which expresses PD1 receptor (programmed death receptor), PDL1 ligand or CTLA-4 (cytotoxic T-lymphocyte-associated protein 4 also known as CD152). The PD1-PD-L1/PD-L2 interaction enables the tumor to escape action by the CAR-targeted T cell by deactivating the T cells and increasing apoptosis and cell exhaustion. For example, PD-1 is a receptor for B7-4 (B7-4 molecules are expressed on antigen presenting cells); B7-4 can inhibit immune cell activation upon binding to an inhibitory receptor on an immune cell. Thus, to prevent or reduce T cell inhibition, the present invention contemplates the use of inhibitors for immune checkpoints for PD1, PDL1 ligand or CTLA-4.

Thus, the methods as described herein for purifying TCR-negative CAR$^+$ immune cells with an anti-TCR mRNA transiently expressed include a step for inactivation of at least one gene involved as an immune checkpoint such as PDCD1, PDL1 ligand or CTLA-4. This additional step is performed subsequently to step (a) and before step (d). For example, treating the CAR+ T cells with PDCD and/or CTLA-4-specific nucleases or transcription factors, in which the PDCD or CTLA-4 gene(s) is (are) knocked out results in a T cell expressing a CAR of interest that is resistant to the PD1 ligand produced by the cancer cell, and thus is not subject to PD-1 mediated T cell exhaustion and/or resistant to CTLA-4 mediated T cell inhibition. Alternatively, the endodomain in a CAR may include an inhibitory signal (e.g., PD1) in a cell expressing the CAR such as e.g., a T cell or a natural killer (NK) cell. For example, the CAR may comprise an antigen binding domain selectively recognizing an antigen, and the endodomain may cause or promote the cell comprising the CAR to activate cell killing and also result in inducing an inhibitory signal in the cell.

As explained above, medical treatment with second or third generation of CAR$^+$ immune cells may in some cases lead to adverse side effects due to the uncontrolled T cell proliferation or activation, or activation against unpredicted antigens on healthy cells of the patient. Hence, in order to decrease the risk of direct toxicity and uncontrolled proliferation, the engineered TCR-negative CAR T cells in addition to the anti-TCR mRNA include a further genetic construct encoding e.g. a suicide gene or other gene that eliminate the transgenic cells as required, such as HSV-TK (reviewed in Bondanza et al., Blood 107, 1828-1836 (2006). Thus, in certain embodiments, the methods as described herein for purifying TCR-negative CAR$^+$ immune cells with an anti-TCR mRNA transiently expressed includes the introduction of a construct encoding an inducible suicide gene. The step of the introduction of a suicidal gene is performed subsequently to step (a) and before step (d) of the methods described herein.

The use of suicide genes for eliminating transformed or transduced cells is well-known in the art. Thus, in certain embodiments, the methods described herein contemplate an expression vector that encodes a CAR and that comprises an inducible suicide gene (e.g., caspase 9, herpes simplex virus, thymidine kinase (HSV-tk), cytosine deaminase (CD) and cytochrome P450).

One suicide gene for donor lymphocyte infusions is the thymidine kinase gene of herpes simplex virus type I (HSV-tk) in combination with its pro-drug, the antiviral substance ganciclovir, although it can be immunogenic (Bonini et al., (1997), Science 276:1719-1724); Bordignon et al., 1995; Tiberghin et al. 2001). Bonini et. al. teach that donor lymphocytes transduced with the HSV-TK suicide gene provide antitumor activity in patients for up to one year and elimination of the transduced cells is achieved using ganciclovir. Further, Gonzalez, et al. ((2004) J. Gene Med. 6:704-711) describe the targeting of neuroblastoma with cytotoxic T lymphocyte clones genetically modified to express a chimeric scFvFc: zeta immunoreceptor specific for an epitope on L1-CAM, wherein the construct further expresses the hygromycin thymidine kinase (HyTK) suicide gene to eliminate the transgenic clones.

In certain embodiments, the inducible suicide gene is non-immunogenic to humans, such as caspase 9 or caspase-8 or cytosine deaminase. For example, caspase-9 can be activated using a specific chemical inducer of dimerization (CID) (US20130071414). Budde et al. (2013) teach a CAR, i.e., CD20 CAR, combined with an inducible caspase 9 (iC9) suicide switch. In the application US 2014/0286987, the latter gene is made functional in the presence of the prodrug AP1903 (tacrolimus) by binding to the mutated FK506-binding protein (FKBP1). A clinical trial is ongoing sponsored by the company Bellicum in which the above capsase technology (CaspaCIDe®) is engineered into GD2 targeted third generation CAR T cells. A similar apoptosis-inducing system based on a multimerizing agent is described in the application WO 2014/152177.

In one embodiment, there is an immune cell comprising an expression vector that encodes a CAR (which is not an anti-TCR CAR), and in addition to the introduction of the antigen-encoding mRNA, further includes the RQR8 suicide gene allowing the depletion of the engineered immune cells in the event of undesirable effects. Philip et al (2014) describes the RQR8 system which is being used as compact marker/suicide gene allowing selection of transduced cells. RQR8 derives from the combination of target epitopes from both CD34 and CD20 antigens. This construct allows selection with the clinically approved CliniMACS® CD34 system (Miltenyi). Moreover, this RQR8 construct binds the widely used pharmaceutical antibody rituximab, resulting in selective depletion of transgene-expressing cells. Within this system, RQR8 is co-expressed with a CAR in a retroviral vector using the foot-and-mouth disease 2A peptide, resulting thereby into the expression of 2 independent transgenes (RQR8 and CAR) on the surface of the T-cells.

The suicide gene can be expressed from the same promoter as the CAR. Alternatively, the suicide can be expressed from another promoter: one promoter drives the expression of the CAR, while the suicide gene can be expressed from an independent promoter. Expression of the suicide gene from the same promoter as the CAR is preferred and can be accomplished using any well-known internal ribosome entry site (IRES) or self-cleaving 2a peptide encoding sequence. Known IRES sequences which can be used in the nucleic acid construct of a CAR include, but are not limited to, IRES from EMCV, c-myc, FGF-2, poliovirus and HTLV-1.

CAR T cells can promote acute adverse events after being transferred into patients. Among the well documented adverse events is graft-versus-host-disease (GvHD), on-target off-tumor activity or aberrant lymphoproliferative capacity due to vector derived insertional mutagenesis. Thus, in one embodiment, the extracellular binding domain of the CAR may comprise an epitope-tagging domain, which can be bound by monoclonal antibodies in order to deplete the immune cells. The inventors have previously described an mAb-driven sorting/depletion system, in which the extracellular binding domain (scFv) of the CAR is modified in such a way to allow both cell sorting and cell depletion, as described by the WO 2016120216 which is incorporated herein by reference. The structure of the system consists in inserting a selected epitope within the scFv; this epitope having a specificity to be recognized by a specific antibody (preferably mAb). Given the fact that mainly the external ligand binding domain of the CAR is modified to include the epitope, different CAR architectures can be envisioned: single-chain or multi-chain. The chimeric scFv of the invention, which is formed of the VH and VL polypeptides and the specific epitope(s) may itself have different structures depending on the position of insertion of the epitope and the use of linkers. Several epitope-mAb couples can be used to generate such system; in particular those already approved for medical use, such as CD20/ rituximab as a non-limiting example.

Drug hypersensitivity is unpredictable and remains an important clinical issue for CAR T cell therapy. It consists of a variety of phenotypes, mainly the cutaneous adverse reactions which range from milder skin reactions (e.g., exanthem, urticaria, and angioedema) to life-threatening adverse reactions. Thus, in one embodiment, the method for inducing CAR immune cells includes inactivation of at least one gene involved in drug hypersensitivity, such the genes encoding GGH (glucagon), RhoA (Ras homolog gene family, member A), CDK5, CXCR3, NR1H2, URG4, PARP14, AMPD3, CCDC38, NFU1 and CACNG5 protein. The inactivation step is performed subsequently to step (a) and before step (d) of the methods described herein.

Additional introduction of an ON or OFF switch system into the CAR+ immune cell of the present invention would allow the modulation of the activity of CAR into the cell, wherein the switch system is selected from the list of epitope tagging, drug resistance, drug hypersensitivity; and CD52 inactivation combined to Alemtuzumab selection. For example, knocking out the CD52 gene makes donor T-cells resistant to the lymphodepleting agent Alemtuzumab (an antibody against CD52). The step for introduction of an ON and OFF switch system carried out subsequently to step (a) and before step (d) of the methods described herein.

It is also contemplated a cell comprising a plurality of CARs transiently co-expressed with an mRNA, wherein each CAR comprises a different antigen binding domain against a TCR, a TCR subunit, a TCR-associated protein, a transmembrane domain, and an intracellular domain of a costimulatory molecule).

Also included in the invention is a composition for treating a mammal, preferably a human having a disease, disorder or condition associated with an elevated expression of a tumor antigen. The composition comprises administering to the mammal an effective amount of a TCR-negative CAR+ cells comprising a CAR which is not an anti-TCR CAR wherein the CAR comprises a binding domain, a transmembrane domain, and an intracellular domain of a costimulatory molecule.

The invention additionally includes compositions for treating a human with cancer or for administering to the human a TCR-negative CAR+ T cell comprising a CAR which is not an anti-TCR CAR.

Methods and Compositions
General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Electroporation-mediated mRNA transfection is a transient expression system. Successful electroporation of mRNA into primary T lymphocytes has now been used for efficient TCR gene transfer (Zhao, et al., 2006, Mol Ther 13(1):151-159; Zhao, et al., 2005, J. Immunol. 174(7):4415-4423). (Rabinovich, et al., 2009, Hum Gene Ther 20(1):51-61).

CARs

Typically, the expression of natural or synthetic nucleic acids encoding CARs is achieved by operably linking a nucleic acid encoding the CAR polypeptide or portions thereof to a promoter, and incorporating the construct into an expression vector. The vectors can be suitable for replication and integration into eukaryotes. Typical cloning vectors contain transcription and translation terminators, initiation sequences, and promoters useful for regulation of the expression of the desired nucleic acid sequence. The nucleic acid can be cloned into a number of types of vectors, including, but not limited to a plasmid, a phagemid, a phage derivative, an animal virus, and a cosmid. Vectors of particular interest include expression vectors, replication vectors, probe generation vectors, and sequencing vectors.

Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, lentivirus, adenoviruses, adeno-associated viruses and herpes viruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, retrovirus vectors are used. In some embodiments, adenovirus vectors are used. A number of adenovirus vectors are known in the art. In the preferred embodiment, lentivirus vectors are used. In the more preferred embodiment, AAV6 vectors are used.

Generally, in a CAR the nucleic acids encoding the scFvs are first constructed via a PCR approach and are sequence verified. They are linked to transmembrane domains, CD3ζ signaling moieties, co-stimulatory domains and introduced into the cells (e.g., via retroviral or lentiviral or other targeting/delivery mechanisms).

The CARs introduced into the immune cells according to the methods of described herein can adopt different design such as single-chain or multi-chain CARs. These different designs allow various strategies for improving specificity and binding efficiency towards the targeted pathological cells. Some of these strategies are illustrated in the figures of the present application. Single-chain CARs are the most classical version in the art. Multi-chain CAR architectures were previously developed by the applicant as allowing modulation of the activity of T-cells in terms of specificity and intensity. The multiple subunits can shelter additional co-stimulation domains or keep such domains at a distance, as well as other types of receptors, whereas classical single chain architecture can sometimes be regarded as too much sensitive and less permissive to multispecific interactions.

Single-Subunit CAR (ssCAR)

By way of example, single-chain CAR (scCAR), (or the Single-subunit CAR (ssCAR)) has one of the polypeptide structure selected from V1, V3 or V5, comprising (a) an extra cellular ligand binding-domain comprising VH and VL from a monoclonal antibody directed against a cell surface antigen target of said CAR; (b) a hinge chosen from the group consisting of CD8α, FcERIII gamma and IgG1; (c) a CD8α transmembrane domain; (d) a cytoplasmic domain including a CD3ζ signaling domain; and (e) a 4-1BB co-stimulatory domain.

In one embodiment, the CAR comprises the extracellular domain of a single chain variable domain of an anti-CD38 monoclonal antibody, as previously described by the inventors in WO2015121454.

In another embodiment, the CAR comprises the extracellular domain of a single chain variable domain of an anti-CD123 monoclonal antibody, as described previously.

In another embodiment, the CAR comprises the extracellular domain of a single chain variable domain of an anti-CD22 monoclonal antibody, as described previously.

In another embodiment, the CAR comprises the extracellular domain of a single chain variable domain of an anti-CS1 monoclonal antibody, as described previously.

In another embodiment, the CAR comprises the extracellular domain of a single chain variable domain of an anti-CLL-1 monoclonal antibody, as described previously.

In another embodiment, the CAR comprises the extracellular domain of a single chain variable domain of an anti-CD19 monoclonal antibody, as described previously (Carpenito, Milone et al. 2009, Milone, Fish et al. 2009).

In one embodiment, the CAR comprises the extracellular domain of a single chain variable domain of an anti-o acetyl GD2 monoclonal antibody.

In one embodiment, the antigen binding domain of the CAR binds one of the following antigens: CD123, CD19, CS1, CD38, CLL1, hsp70, CD22, ROR1, EGFRvIII, BCMA, CD33, FLT3, CD70, WT1, MUC16, PRAME, TSPAN10, ROR1, GD3.

It is known that signals generated through the TCR alone are insufficient for full activation of the T cell and that a secondary or co-stimulatory signal is also required. That is, the T cell activation can be said to be mediated by two distinct classes of cytoplasmic signaling sequence: those that initiate antigen-dependent primary activation though the TCR (primary cytoplasmic signaling sequences) and those that act in an antigen-independent manner to provide a secondary or co-stimulatory signal (secondary cytoplasmic signal sequences). Thus, with respect to the endodomain (or cytoplasmic) domain of a CAR, primary cytoplasmic signaling sequences that act in a stimulatory manner may contain signaling motifs which are known as immunoreceptor tyrosine-based activation motifs or ITAMs. In one embodiment, the endodomain of a CAR include those ITAMs derived from TCRζ, FcR gamma, FcR beta, CD3 gamma, CD3 delta, CD3 epsilon, CD5, CD22, CD79a, CD79b, and CD66d.

A costimulatory molecule is a cell surface molecule other than antigen receptors or their ligands that is required for an efficient response of lymphocytes to an antigen. In one embodiment, the endodomain domain of a CAR includes costimulatory molecules, such as, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like, and any combination thereof.

In one embodiment, the tumor antigen is an antigen associated with a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

Multi-Subunit CAR or Multichain CAR

Chimeric antigen receptors from the prior art introduced in T-cells have been formed of single chain polypeptides that necessitate serial appending of signaling domains. However, by moving signaling domains from their natural juxtamembrane position may interfere with their function. To overcome this drawback, the applicant recently designed a multi-chain CAR derived from FCERI to allow normal juxtamembrane position of all relevant signaling domains. In this new architecture, the high affinity IgE binding domain of FCERI alpha chain is replaced by an extracellular ligand-binding domain such as scFv to redirect T-cell specificity against cell targets and the N and/or C-termini tails of FCERI beta chain are used to place costimulatory signals in normal juxtamembrane positions.

Accordingly, the CAR expressed by the engineered T-cell according to the invention can be a multi-chain chimeric antigen receptor (CAR) particularly adapted to the production and expansion of engineered T-cells of the present invention. Such multi-chain CARs comprise at least two of the following components: a) one polypeptide comprising the transmembrane domain of FCERI alpha chain and an extracellular ligand-binding domain, b) one polypeptide comprising a part of N- and C-terminal cytoplasmic tail and the transmembrane domain of FCERI beta chain and/or c) at least two polypeptides comprising each a part of intracytoplasmic tail and the transmembrane domain of FCERI gamma chain, whereby different polypeptides multimerize together spontaneously to form dimeric, trimeric or tetrameric CAR.

According to such architectures, ligands binding domains and signaling domains are born on separate polypeptides. The different polypeptides are anchored into the membrane in a close proximity allowing interactions with each other. In such architectures, the signaling and costimulatory domains can be in juxtamembrane positions (i.e. adjacent to the cell membrane on the internal side of it), which is deemed to allow improved function of costimulatory domains. The multi-subunit architecture also offers more flexibility and possibilities of designing CARs with more control on T cell activation. For instance, it is possible to include several extracellular antigen recognition domains having different specificity to obtain a multi-specific CAR architecture. It is also possible to control the relative ratio between the different subunits into the multi-chain CAR. This type of architecture has been recently described by the applicant in PCT/US2013/058005 (WO2014/039523).

The assembly of the different chains as part of a single multi-chain CAR is made possible, for instance, by using the different alpha, beta and gamma chains of the high affinity receptor for IgE (FCERI) (Metzger, Alcaraz et al. 1986) to which are fused the signaling and co-stimulatory domains. The gamma chain comprises a transmembrane region and cytoplasmic tail containing one immunoreceptor tyrosine-based activation motif (ITAM) (Cambier 1995).

The multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multi-chain CAR. In another embodiment, the present invention relates to a population of multi-chain CARs comprising each one different extracellular ligand binding domains. In a particular, the present invention relates to a method of engineering immune cells comprising providing an immune cell and expressing at the surface of said cell a population of multi-chain CAR each one comprising different extracellular ligand binding domains. In another particular embodiment, the present invention relates to a method of engineering an immune cell comprising providing an immune cell and introducing into said cell polynucleotides encoding polypeptides composing a population of multi-chain CAR each one comprising different extracellular ligand binding domains. In a particular embodiment the method of engineering an immune cell comprises expressing at the surface of the cell at least a part of FCERI beta and/or gamma chain fused to a signal-transducing domain and several part of FCERI alpha chains fused to different extracellular ligand binding domains. In a more particular embodiment, said method comprises introducing into said cell at least one polynucleotide which encodes a part of FCERI beta and/or gamma chain fused to a signal-transducing domain and several FCERI alpha chains fused to different extracellular ligand binding domains. By population of multi-chain CARs, it is meant at least two, three, four, five, six or more multi-chain CARs each one comprising different extracellular ligand binding domains. The different extracellular ligand binding domains according to the present invention can preferably simultaneously bind different elements in target thereby augmenting immune cell activation and function.

The present invention also relates to an isolated immune cell which comprises a population of multi-chain CARs each one comprising different extracellular ligand binding domains.

The signal transducing domain or intracellular signaling domain of the multi-chain CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines.

In the present application, the term "signal transducing domain" refers to the portion of a protein which transduces the effector signal function signal and directs the cell to perform a specialized function.

Preferred examples of signal transducing domain for use in single or multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the multi-chain CAR can comprise the CD3zeta signaling domain, or the intracytoplasmic domain of the FCERI beta or gamma chains.

In particular embodiment the signal transduction domain of the multi-chain CAR of the present invention comprises a co-stimulatory signal molecule. A co-stimulatory molecule is a cell surface molecule other than an antigen receptor or their ligands that is required for an efficient immune response.

Ligand binding-domains can be any antigen receptor previously used, and referred to, with respect to single-chain CAR referred to in the literature, in particular scFv from monoclonal antibodies. Bispecific or multi-specific CARs as described in WO 2014/4011988 are incorporated by reference.

RNA

In general, the mRNA has both a cap on the 5' end and a 3' poly(A) tail which increase the ribosome binding, initiation of translation and stability mRNA in the cell. The read out (half life) is increased by a factor of at least 2 as compared to an mRNA without a 3' poly(A) tail.

Phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003)).

In general sequences downstream of a poly(A/T) stretch of 64-100 nucleotides results in good templates (Saeboe-Larssen et al., J. Immunol. Meth., 259:191-203 (2002); Boczkowski et al., Cancer Res., 60:1028-34 (2000); Elango et al., Biochem Riophys Res Commun., 330:958-966 2005). The RNA that can fold into a stem-loop structure followed by a track of uridine residues (Dunn and Studier, J. Mol. Biol., 166:477-535 (1983); Arnaud-Barbe et al., 1998 Nuc. Acids Res., 26:3550-54 (1998)), forming a type of "dynamic" terminator to prevent potential aberrant transcription: a 3' extension of the RNA transcript over a poly(A/T) stretch and transcription in the reverse direction will create a growing termination-like signal—an extended poly(U) stretch and a poly(A/U) hairpin.

Based on this, reversed PCR primers were designed with a 3' anchoring sequence downstream of the coding sequences of an anti-TCR or anti-CD3 CAR gene and a 5' 100 base stretch of poly(T).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (A). The examples below demonstrate that a 100 base-pair stretch of poly(A) is sufficient to enable efficient translation of an RNA transcript.

Poly(A) tails of RNAs can be further extended with the use of a poly(A) polymerase, such as E. coli polyA polymerase (E-PAP). Increasing the length of a poly(A) tail from 100 nucleotides to between 300 and 400 nucleotides results in about a two-fold increase in the translation efficiency of the RNA.

Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. Suitable ATP analogs include, but are not limited to, cordiocipin and 8-azaadenosine.

5' caps also provide stability to RNA molecules. In a preferred embodiment, RNAs produced by the methods disclosed herein include a 5' cap. The 5' cap may, for example, be m7G(5')ppp(5')G, m7G(5')ppp(5')A, G(5')ppp(5')G or G(5')ppp(5')A cap analogs, which are all commercially available. The 5' cap can also be an anti-reverse-cap-analog (ARCA) (also Stepinski, et al., RNA, 7:1468-95 (2001)) or any other suitable analog. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In addition, the method and means described in WO2017123242 A1 were applied to the mRNA of the present invention.

The RNAs provided herein can also contain an internal ribosome entry site (IRES) sequence. The IRES sequence may be any viral, chromosomal or artificially designed sequence which initiates cap-independent ribosome binding to mRNA and facilitates the initiation of translation.

Any solutes suitable for cell electroporation, which can contain factors facilitating cellular permeability and viability such as sugars, peptides, lipids, proteins, antioxidants, and surfactants can be included.

The introduction of an mRNA encoding an anti-TCR CAR into a genetically modified CAR+ immune cell to achieve temporarily expression of anti-TCR CAR on the cell surface has been shown to be beneficial to enrich CAR expressing immune cells before being administered to a patient.

In one embodiment, the introduced mRNA expresses on the cell surface the corresponding antigen recognized by a TCR, i.e., alpha TCR subunit, beta TCR subunit, CD3. Any antigen recognized by an anti-TCR CAR is within the purview of the invention. Thus, the template for the mRNA encoding CAR specific or the alpha beta TCR is designed to be directed to any antigen binding domain of the alpha beta TCR that was, or will be, transduced into the cell.

A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length, preferably 120 bases (SEQ ID NO: 11). RNA so produced can efficiently be delivered into different types of eukaryotic cells as well as into tissues and whole organisms using transfected cells as carriers or cell-free local or systemic delivery of encapsulated, bound or naked mRNA.

The tumor antigen may be purified and isolated from natural sources such as from primary clinical isolates, cell lines and the like. The cancer peptides may also be obtained by chemical synthesis or by recombinant DNA techniques known in the arts. Techniques for chemical synthesis are described in Steward et al. (1969); Bodansky et al. (1976); Meienhofer (1983); and Schroder et al. (1965). Furthermore, as described in Renkvist et al. (2001), there are numerous antigens known in the art. Other antigens, identified by antibodies and as detected by the Serex technology (see Sahin et al. (1997) and Chen et al. (2000)), are identified in the database of the Ludwig Institute for Cancer Research.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. Any DNA polymerase useful for PCR can be used in the methods disclosed herein. The reagents and polymerase are commercially available from a number of sources.

In one embodiment, the DNA to be used for PCR contains an open reading frame. The DNA can be from a naturally occurring DNA sequence from the genome of an organism. In one embodiment, the DNA is a full-length gene of interest or a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Thus, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. For example, 3' or 5' sequences from mRNA molecules which are stable (e.g., globin, actin, GAPDH, tubulin, histone, or citric acid cycle enzymes) can be incorporated into the 3' and/or 5' region of a sense mRNA nucleic acid molecule to increase the stability of the sense mRNA molecule. The 5' UTR can be derived from an RNA virus whose RNA genome is stable in cells. It is also known that AU-rich elements in 3' UTR sequences can decrease the stability of mRNA. Various nucleotide analogues can be used in the 3' or 5' UTR to impede exonuclease degradation of the mRNA. Therefore, 3' UTRs can be selected or designed to increase the stability of the transcribed RNA based on properties of UTRs that are well known in the art.

Kozak consensus sequence plays a role in the initiation of protein translation, and the inclusion of such a Kozak consensus sequence in the antigen-encoding mRNA nucleic acids of the present invention may further extend or prolong the activity of the mRNA nucleic acids (Kozak, M., Nucleic Acids Res 15 (20): 8125-48 (1987)). However, the Kozak consensus sequence does not appear to be required for all mRNAs to enable efficient translation. Thus, the 5' UTR may contain the Kozak sequence of the endogenous gene. Alternatively, when a 5' UTR that is not endogenous to the gene of interest is being added by PCR as described above, a consensus Kozak sequence can be redesigned by adding the 5' UTR sequence.

5' caps can also provide stability to RNA molecules. The 5' cap is provided using techniques known in the art and described herein (Cougot, et al, Trends in Biochem. Sci., 29:436-444 (2001); Stepinski, et al, RNA, 7:1468-95 (2001); Elango, et al, Biochim. Biophys. Res. Commun., 330:958-966 (2005)).

The stability and the translational efficiency of the antigen-encoded mRNA in transiently transfected (e.g., electroporation) cells can be monitored by expansion or contraction of the adenosine bases, the poly(A) tail. The poly A tail is thought to stabilize natural messengers and synthetic sense RNA. Therefore, in one embodiment a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase, such as E. coli polyA polymerase (E-PAP) (Yokoe, et al. Nature Biotechnology. 1996; 14:1252-1256). A transcription vector can also encode long poly(A) tails. Alternatively, the polyA/T segment of the transcriptional DNA template can be produced during PCR by using a reverse primer containing a poly(A) tail, such as 100T tail (size can be 50-5000 T), or after PCR by any other method, including, but not limited to, DNA ligation or in vitro recombination. Poly(A) may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

In one embodiment, the nucleic acid sequence of the mRNA comprises a poly(A) tail comprising about 50 to 5000 adenosine bases, preferably 120 A, (SEQ ID NO 11).

The RNAs can also contain an internal ribosome entry site (IRES) sequence. The IRES sequence may be any viral, chromosomal or artificially designed sequence which initiates cap-independent ribosome binding to mRNA and facilitates the initiation of translation.

In addition, suitable modifications include alterations in one or more nucleotides of a codon such that the codon encodes the same amino acid but is more stable than the codon found in the wild-type version of the nucleic acid. For example, an inverse relationship between the stability of RNA and a higher number of cytidines (C's) and/or uridines (U's) residues has been demonstrated, and RNA devoid of C and U residues have been found to be stable to most RNases (Heidenreich, et al. J Biol Chem 269, 2131-8 (1994)). In some embodiments, the number of C and/or U residues in an mRNA sequence is reduced. In an another embodiment, the number of C and/or U residues is reduced by substitution of one codon encoding a particular amino acid for another codon encoding the same or a related amino acid. Contemplated modifications to the mRNA nucleic acids of the present invention also include the incorporation of pseudo-uridines. The incorporation of pseudo-uridines into the mRNA nucleic acids of the present invention may enhance stability and translational capacity, as well as diminishing immunogenicity in vivo. (See, e.g., Karikó, K., et al., Molecular Therapy 16 (11): 1833-1840 (2008)). Substitutions and modifications to the nucleic acids of the present invention may be performed by methods readily known to one or ordinary skill in the art.

In one embodiment, the present invention includes synthetic RNA and RNA-like analogs encoding the antigen recognized by the CAR of the invention, i.e., synthesis of the antigen-encoding mRNA construct includes the incorporation of nucleotide/nucleoside derivatives or analogs. For example, one type of analog is LNA, such as beta-D-oxy-LNA, alpha-L-oxy-LNA, beta-D-amino-LNA and beta-D-thio-LNA, and beta-D-oxy-LNA. Methods of producing synthesized RNA are well known in the art, described, for example, in U.S. Pat. Nos. 8,242,248, 6,111,095, U.S. Patent Application Publication No.: 2010/0324278, U.S. Patent Application Publication No.: 2010/0137010, and PCT International Publication No.: WO 2007/031081, each of which is incorporated by reference.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

Delivery of the mRNA Encoding the Antigen Target Recognized by a CAR mRNA

The anti-TCR mRNA transfection methods of the invention are essentially transient and vector-free. Transfection using in vitro-transcribed mRNA can be accomplished by any means known in the art.

Electroporation-mediated administration into cells of nucleic acids including expression constructs utilizing any of the many available devices and electroporation systems known to those of skill in the art. Electroporation is used since it provides a powerful tool to introduce genes into both human and murine primary T lymphocytes (Zhao et al., "High-efficiency transfection of primary human and mouse T lymphocytes using RNA electroporation," Mol. Ther. 13(1):151-9, 2006. Epub 2005 Sep. 2). See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and U.S. Pat. No. 7,173,116. Apparatus for therapeutic application of electroporation are available commercially, e.g., the MedPulser™ DNA Electroporation Therapy System (Inovio/Genetronics, San Diego, Calif), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1.

In the preferred embodiment, the electroporation has been carried out by the inventors with the cytoPulse technology (also known as PulseAgile®) which allows, by use of pulsed electric fields, to transiently permeabilize living cells for delivery of material into the cells (U.S. Pat. No. 6,010,613 and WO 2004/083379).

In other embodiments, anti-TCR mRNAs can be delivered into the cells by calcium phosphate precipitation, lipofection, particle bombardment, microinjection, colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

The use of lipid formulations is contemplated for the introduction of the anti-TCR mRNAs into an immune cell (in vitro, ex vivo or in vivo). The mRNA associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid/RNA associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL.).

Engineered Genetically Modified CAR+ T-Cells

To generate a T cell population that expresses a CAR and in which an mRNA encoding anti-TCR CAR is transiently expressed on the cell surface, CAR containing T cells are generated. Cells (e.g., PBMCs, T-cells such as TILs, CD4+ or CD8+ cells) are purified from natural sources, for example, a metastatic melanoma patient, and cultured and/or expanded according to standard procedures. Cells may be stimulated, for example, as described in U.S. Patent Publication No. 20080311095. Cells are transduced with a CAR. Alternatively, the mRNA encoding anti-TCR CAR is introduced prior to the transduction with the CAR. Examples of CAR within the purview of the present inventions include an anti-CD38 CAR, an anti-CD19 CAR, an anti-CD123 CAR, an anti-CD30 CAR, or an anti-CD22 CAR. However, the invention should not be limited to these antigens as the target molecule. Rather, any CAR comprising an antigen binding domain directed against any target molecule can be used in the context of a transiently co-expressed mRNA encoding the anti-TCR CAR.

In the particular embodiments where the antigen marker is common to both the pathological cells and the immune cells, as in the case of the antigen CD38, the peripheral blood mononuclear cells (PBMC) are stimulated and first treated with a Transcription Activator Like Effector Nuclease (TALEN®) gene editing technology to inactivate the endogenous expression of the CD38 gene, and the cells rest for 2 days before being transduced with anti-CD38 CAR, as previously described in WO2015121454 (also described by Mathilde Dusseaux, Le Clerre D, Gouble A, Smith J, EHA Posters (2016), Cellectis SA Press Release Jun. 11, 2016, "Allogeneic TCR A/CD38 Double Knockout T Cells Bearing an Anti-CD38 Chimeric Antigen Receptor (CAR): An Improved Immunotherapy for the Treatment of T-Cell Acute Lymphoblas; Leukemia (T-ALL) and Multiple Myeloma (MM)), which references are herein incorporated by reference. That is, the inactivation of the endogenous CD38 gene occurs before either the transduction with the anti-CD38CAR or the transfection with the anti-TCR CAR-encoding mRNA.

In some embodiments, the CAR sequences are delivered into cells using a retroviral or lentiviral vector or an AAV vector. CAR-expressing retroviral and lentiviral vectors can be delivered into different types of eukaryotic cells as well as into tissues and whole organisms using transduced cells a carriers or cell-free local or systemic delivery of encapsulated, bound or naked vectors.

In the preferred embodiment, the methods described herein are used to evaluate personalized therapy. For example, for treatment of tumors, the patient's blood or cells is collected by an appropriate method such as apheresis, biopsy or venapuncture. The cells are cultured for at least 24 hours during which time the cells are transduced with an appropriate CAR-containing retroviral or lentiviral vector. An mRNA encoding the anti-TCR CAR is introduced into the cells and the anti-TCR CAR is transiently expressed on the cell surface, thus autoactivating the TCR$^+$ immune cells to proliferate upon binding with the anti-TCR CAR. The anti-TCR CAR+ immune cells can be stored frozen, if necessary.

Sources of Cells

Prior to expansion and genetic modification or other modification, a source of cells, e.g., T cells, can be obtained from a subject. The term "subject" is intended to include living organisms in which an immune response can be elicited (e.g., mammals). Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain aspects of the present disclosure, immune effector cells, e.g., T cells, can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe® 2991 cell processor, the Baxter CytoMate™, or the Haemonetics® Cell Saver 5) according to the manufacturer's instructions. After washing, the cells may be re-suspended in a variety of biocompatible buffers, such as, for example, Ca-free, Mg-free PBS, Plasma-Lyte® A, or other saline solution with or without buffer. Alternatively, the undesirable components of the apheresis sample may be removed and the cells directly re-suspended in culture media.

In the present invention, PBMC cryopreserved cells were thawed and washed as described herein and allowed to rest for one hour at room temperature prior to activation using the methods of the present invention.

It is contemplated to collect blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH®, anti-CD3 antibodies, CYTOXAN®, fludarabine, cyclosporin, FK506, rapamycin, mycophenolic acid, steroids, FR901228, and irradiation.

It is also contemplated that T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy.

In an embodiment, the NK cells are obtained from the subject. In another embodiment, the NK cells are an NK cell line, e.g., NK-92 cell line (Conkwest).

It is contemplated that hematopoietic cells may be used in the present invention.

Activation and Expansion of Temporarily Highly Activated $CAR^+$ T Cells.

In one particular embodiment, briefly, the cells were knocked out for the endogenous expression of the TCR gene, followed by a rest period of 2 days the cells were then transduced with a nucleic acid encoding anti-TCR CAR described herein, are expanded in the presence of interleukin-2 (IL-2) for a period of two days. In addition, the T-cells are engineered to co-express the RQR8 gene as a safety feature, with the aim of rendering them sensitive to the monoclonal antibody rituximab. RQR8 is a suicide gene that enable selective deletion of the transduced cells in vivo. Upon introduction of the anti-TCR CAR mRNA into the CAR T cells, the resulting cells are of phenotype anti-TCR $CAR^+$ T–. The cells are then expanded in culture for a period of 4 to 11 days. In one embodiment, the cells are expanded for a period of 4 days, for a period of 5 days, or for a period of 7 days.

Therapeutic Application

The efficacy of TCR-negative $CAR^+$ immune cells of the invention can be tested using art-recognized animal models for the particular indication of interest. For example, in the context of cancer, established cancer mouse models are widely available for the particular cancer of interest.

Ex vivo procedures are well known in the art. Briefly, cells are isolated from a mammal (preferably a human) and genetically modified (i.e., transduced or transfected in vitro) with a CAR and transiently with an mRNA encoding anti-TCR CAR in the cell surface, the cells may further include another modification as described herein. The modified cell can be administered to a mammalian recipient to provide a therapeutic benefit. The mammalian recipient may be a human and the genetically modified cell can be autologous with respect to the recipient. Alternatively, the cells can be allogeneic, syngeneic or xenogeneic with respect to the recipient.

Thus, the present invention includes a type of cellular therapy where T cells are genetically modified to express a chimeric antigen receptor (CAR) and to transiently co-express an mRNA encoding the anti-TCR CAR on the cell surface, resulting in the phenotype $CAR^+T$-APC. The therapy is achieved by infusing the TCR-negative $CAR^+$ T cells into a recipient in need thereof. The infused cells are able to kill cells which express the antigen to which the antigen-binding domain of the CAR binds, with no GVHD. In particular, the TCR-negative $CAR^+$ cells administered to the patient should not persist more than 20 days This is also safer than previously observed with cell having TCR+T cells.

Non-limiting examples of a cancer that can be treated by the present invention include brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof.

In a preferred embodiments the following cancers and there relapsed refractory forms can be treated by the composition of the invention: said cancer is selected from Acute myeloid leukemia (AML), Chronic myeloid leukemia (CML), Acute lymphoblastic leukemia (ALL), Hodgkin lymphoma (HL) (relapsed, refractory), Non-Hodgkin lymphoma (NHL) (relapsed, refractory), Neuroblastoma, Ewing sarcoma, Multiple myeloma, Myelodysplastic syndromes, BPDCN, Gliomas, other solid tumors, including pancreatic or lung cancer, bladder cancer, colon cancer, breast cancer.

Pharmaceutical Compositions

The present invention relates to pharmaceutical compositions comprising at least one population of TCR-negative $CAR^+$ immune cells. Such pharmaceutical compositions are contemplated for use in the treatment of cancer, infection or immune disease.

The genetically modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, $17^{th}$ ed., 1989).

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials. When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. CAR T cell compositions may also be administered multiple times at these dosages. The cells can be administered by using infusion techniques that are commonly known in immunotherapy (see, e.g., Rosenberg et al, New Eng. J. of Med. 319:1676, 1988). The optimal dosage and treatment regime for a particular patient can readily be determined by one skilled in the art of medicine by monitoring the patient for signs of disease and adjusting the treatment accordingly.

Delivery of Anti-TCR $CAR^+$ Immune Cells

In embodiments of the invention, cells generated by methods of the invention are delivered to a mammal. Cell delivery vehicles are known in the art and may be employed to deliver cells of the invention. T cells or NK modified with the methods of the present invention are usually infused intravenously or in body cavities site of specific disease and are re-suspended in saline solutions before infusion.

In one embodiment, there is no requirement to purify the expanded TCR-negative $CAR^+$ immune T cells before administering to a patient, i.e., the autoactivated $CAR^+$ immune cells are directly administered to a patient in need thereof.

Suitable doses for a therapeutic effect may be determined by standard means in the art. In specific embodiments, suitable doses are between about $10^6$ and about $10^9$ cells per dose, as an example, preferably in a series of dosing cycles. A preferred dosing regimen may comprise multiple one-week dosing cycles of escalating doses, starting at about $10^6$ cells on Day 0, increasing incrementally up to a target dose of about $10^9$ cells at a later time point. Suitable modes of administration include intravenous, intracavitary (for example by reservoir-access device), intraperitoneal, and direct injection into a tumor mass.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection. In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH®, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al, Cell 66:807-815, 1991; Henderson et al, Immun. 73:316-321, 1991; Bierer et al, Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH®. In another embodiment, the cell compositions of the present invention are administered following B-cell ablative therapy such as agents that react with CD20, e.g., Rituxan®. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for a relevant treatment modality can generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. The examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Transient anti-TCR expression to eliminate TCR-positive T cells from allogeneic cell preparations.

General Method
Anti-TCR CAR Sequences
Anti-CD3 CAR Sequence

The sequence of an anti-CD3 CAR, from the 5' to the 3', comprised: a sequence coding a signal peptide such as a signal peptide from the human CD8alpha used in the construction. This peptide is cleaved. In the construction, the anti-CD3 CAR sequence further comprises from 5' to 3': a sequence coding an anti CD3 scFV, a sequence coding a hinge domain, a sequence coding a CD8alpha transmembrane domain, a sequence coding a 4-1BB intracellular costimulation domain and a /CD3z intracellular activation domain. The sequence may be inserted into a plasmid containing in addition, a sequence coding a 2A element and a sequence coding a BFP reporter gene. This sequence can be further subcloned into a plasmid containing at the 5' extremity a T7 promoter at the 3' extremity a mouse hba 3'UTR and a 120-nucleotide-long polyA. The length of the poly A, nature of CAP, as well as the sequences in the promotor can be modified to extend or shorten the half life of the mRNA encoding the anti-TCR CAR as compared to a construct having a sequence of SEQ ID N°8 or 12:

Standard molecular biology technics such as PCR, enzymatic restriction digestion and ligation are applied to create all constructions.
Anti-TCR Alpha Beta CAR Sequence The sequence of an anti-TCR CAR, comprises at least from the 5' to the 3', a signal peptide sequence, a sequence coding (an anti-alpha TCR scFV, or an anti-beta TCR scFV, or an anti-alpha beta TCR scFV), a CD8alpha hinge domain, a CD8alpha transmembrane domain, a 4-1BB/CD3z costimulation and activation intracellular domain.

All individual constructs, mRNAs encoding an anti-TCR CAR and proteins products are all part of the present invention (SEQ ID NO 1 to SEQ ID NO 22, or combination thereof).

Example of Anti-CD3 CAR Sequence

The sequence of an anti-CD3 CAR was obtained by assembling, from the 5' to the 3', a signal sequence from the human CD8a (SEQ ID NO: 1), an anti CD3 scFV (SEQ ID NO: 2), a CD8a hinge domain (SEQ ID NO: 3), a CD8a transmembrane domain (SEQ ID NO: 4), a 4-1BB/CD3z co-stimulation and activation intracellular domain (SEQ ID NO: 5) into a plasmid containing a 2A element (SEQ ID NO: 6) and a BFP reporter gene (SEQ ID NO: 7), leading to 30527 (SEQ ID NO: 8). This sequence was further subcloned in a plasmid containing at the 5' a T7 promoter (SEQ ID NO: 9) and at the 3' a mouse hba 3'UTR (SEQ ID NO: 10) and a 120-nucleotide-long polyA (SEQ ID NO: 11) leading to sequence 30697 (SEQ ID NO: 12).

This construct resulted in the succession of the following amino acid sequences:
CD8 signal seq (SEQ ID NO: 15)
anti-CD3 scFv (SEQ ID NO: 16)
CD8 hinge (SEQ ID NO: 17)
CD8 trans (SEQ ID NO: 18)
41BB-CD3z (SEQ ID NO: 19)
2A (SEQ ID NO: 20)
BFP (SEQ ID NO: 21)
SEQ ID NO: 22 corresponds to the product obtained with plasmid 30527 (SEQ ID NO: 12).

All constructions alone or combined are part of the present invention.

Construction may be combined to other anti-TCR scfv.

Standard molecular biology technics such as PCR, enzymatic restriction digestion and ligation are applied to create all construction.

Transfection

Four days following activation, human T lymphocytes were transfected by electrotransfer using an AgilePulse MAX™ system (Harvard Apparatus): cells were pelleted and resuspended in cytoporation medium T at >28×10$^6$ cells/ml. 5×10$^6$ cells were mixed with 5 µg total TRAC TALEN mRNA (2.5 ug each of the left and right TALEN arms) into a 0.4 cm cuvette in triplicate. In parallel, two mock transfections (no mRNA) were performed. The electroporation consisted of two 0.1 ms pulses at 800 V followed by four 0.2 ms pulses at 130V. Following electroporation, cells were diluted into 2 mL culture medium and incubated at 37° C./5% CO$_2$. Separate aliquots of TRAC TALEN-transfected cells were again electroporated at days 2, 7, or 9 post TRAC TALEN transfection with 20 ug of anti-CD3 CAR mRNA produced with EPAP-mediated polyadenylation using the mMessage mMachine™ T7 Ultra kit (Thermo fisher scientific) from a PCR product (SEQ ID NO: 22) obtained from 30527 (SEQ ID NO: 8) and oligos1 (SEQ ID NO: 13) and oligo2 (SEQ ID NO: 14) or with 20 ug of anti-CD3 CAR MRNA obtained by T7 RNA polymerase transcription from a plasmid DNA template 30697 (SEQ ID NO: 12) containing, the mouse hba 3'UTR (SEQ ID NO: 10) and the 120-nucleotide-long polyA (SEQ ID NO: 11) after TALEN coding sequence and linearized downstream of the polyA.

Flow Cytometry

The detection of BFP for anti-CD3 CAR expression was performed 24 hours after each CD3 CAR mRNA electroporation. Cell viability was monitored using the efluor780 (ebioscience 65-0865-18) in PBS for 20 min 4° C., followed by a washing step with 2% FBS in PBS and fixed in PFA 4%. Two, three or four days later, the frequency of TCR and CD3-positive cells was assessed. Double labeling was done with anti human TCRab (Miltenyi) (specific for alpha beta TCR) and anti-human CD3 (Miltenyi) antibodies diluted into 2% FBS in PBS, EDTA 2 mM, azide 0.1% for 20 min at 4° C. followed by a washing step with 2% FBS in PBS, EDTA 2 mM azide 0.1%. Viability was assessed on the Vicell. Flow cytometry was performed using the MACSQUANT® (Miltenyi Biotec) and data analysis was performed with the FlowJo™ software. The collected data demonstrated a very efficient depletion of the anti-CD3 mRNA as 90 to 98% depletion of CD3/TCR positive cells was measured as compared cells that were treated with the TRAC TALEN alone (FIG. 1).

(NB: Electroporation of TRAC TALEN mRNA alone resulted in about 90% to 97% TCR reduction as compared to cells that were not electroporated with a TRAC TALEN; at day 4 post electroporation. The calculation of depletion deficiency (%) in FIG. 1 corresponds the decrease in alpha beta TCR expression at day 2 post transfection, with 0% corresponding to the level of alpha beta TCR in TRAC TALEN treated cells at day 2 post electroporation.

Upon transient expression of the anti-TCR CAR the level of alpha betaTCR was undetectable by FACS analysis at day 2, day 7 or day 9 post transfection of the anti-TCR CAR.

This suggested a complete elimination of TCR+ expressing cells in TCR deficient cells exposed to transient expression of anti-TCR CAR.

Coculture of TRAC TALEN PBMCs with TRAC TALEN/Anti-CD3 CAR mRNA PBMCs

Figure 2:
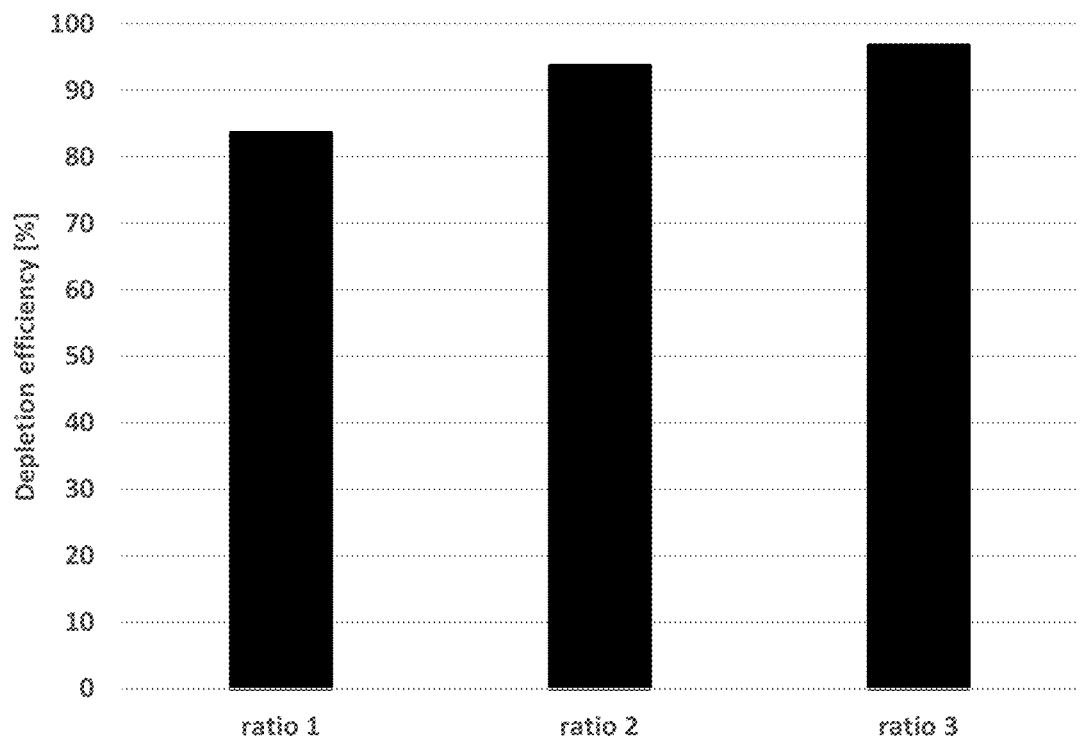

TRAC TALEN-treated cells were electroporated with anti-CD3 CAR mRNA (3'UTR-120A format) (SEQ ID NO: 12) 7 days post TALEN treatment. 24 h later, different ratios of TRAC TALEN only-treated cells and TRAC TALEN plus anti-CD3 CAR double treated cells were mixed at different ratios. After 48 hours of coculture, the TCR and CD3 surface expression were assessed as above (FIG. 2). A dose dependent effect of TRAC TALEN plus anti-CD3 CAR double treated cells is illustrated FIG. 2.

Transient Expression of Anti-TCR CAR in Cell Populations Comprising 60 to 5% TCR+ Cells Cells for the supply step are frozen human peripheral mononuclear cells, from individual healthy donors such as from leukapheresis, thawed before use and comprising more than 80% viable cells.

Cells Expressing Alpha Beta TCR

Any preparation of cells expressing alpha beta TCR may be used.

TALEN-Targeted CAR Gene Integration into the TRAC Locus.

After activation, cells were transfected or not by electrotransfer of 1 µg of mRNA encoding TRAC TALEN per million cells as above. 1.5h later, rAAV6 donor vector comprising a CAR was added or not to the culture at the multiplicity of infection of 3×10$^4$ vg/cell. The CAR could be any CAR (e.g., among those described here, preferably CD123, CD22, CS1, CLL-1 CAR) and CAR expression was assessed by flow cytometry on viable T cells using CD4, CD8, TCRαβ mAb, recombinant protein (full length target of the CAR) in combination with a live/dead cell marker.

The results show that the Integration of the CAR at the TRAC locus is highly efficient since the frequency of CAR$^+$ TCR$^-$ cells reached more than 40%.

Total cells or CAR$^+$ T cells cytolytic capacities towards antigen presenting cells were assessed in a flow-based cytotoxicity assay. The cell viability was measured after 4h or after an overnight coculture with CAR T cells at effector/target ratios set at 10:1, 5:1, 2:1 and 1:1 or 1:1, 0.5:1, 0.2:1 and 0.1:1 respectively.

The results show that the cytolytic activity of these cells was comparable to that of CAR expressing cells obtained by other method (classical transduction).

3 days after activation, T cells were transfected or not by electrotransfer of 1 µg of each mRNA encoding TRAC and CD52 TALEN per million cells.

The results show that this 2-in-1 strategy of TCR KO and CAR KI can be extended to the use of more than one TALEN. The integration of the CAR at the TRAC locus is highly efficient since the frequency of CAR$^+$ TCR$^-$ cells reached more than 47%. Importantly, no CAR expression was detected at the CD52 locus when T cells were transfected only with 1 µg of mRNA encoding CD52 TALEN. More than 80% of the population of CAR$^+$ T cells is knocked-out for both TCRαβ and CD52.

Purification of TCR negative cells resulted in mainly TCRαβ-negative (about 95 to 98%) while around 90% of unmodified T-cells were TCRαβ-positive, as expected.

Transient expression of the anti-TCR CAR (SEQ ID NO 8 or 12) in these cells resulted in undetectable level of TCR by flow cytometry (FACS) analysis.

In addition, the use of transiently expressing anti-TCR CAR T cells for depleting TCR+ T cells in organs before engraftment is performed here.

Further, transient expression of the anti-TCR CAR resulted in a total depletion of TCR+ cells from population expressing up to 60% of TCR+ cells.

When CAR T cells are transfected with mRNA encoding anti-TCR CAR there is a clear enrichment in the CAR negative cell population. This enrichment is dependent on the dose of mRNA transfected and thus the level of anti-TCR CAR transiently expressed on the surface of the CART cells. The frequency of CAR+ TCR− T cells increases over time but this increase is not dose dependent anymore.

When CART cells are transfected with mRNA encoding anti-TCR CAR there is a clear enrichment in the CAR positive cell population. The benefit observed when mRNA encoding the antigen is transfected is more important at lower doses of lentiviral particles when the frequency of CAR+ T cells is less than 5%, at MOI of 1 and 2.

An enrichment in CD8+ T cells is observed and is equivalent between cells that have been transfected and cells that have not been transfected and independent from the amount of mRNA.

The transient transfection of mRNA encoding the anti-TCR CAR does not modify the cytolytic activity of the CD38 CAR or CD123 CAR against target cells isolated from patient and used in this experiment. It even seems that CAR T cells tend to have a slightly improved antitumor activity in vitro (less standard deviation).

Example 2

Assessment of GVHD

To investigate whether expressing a mRNA encoding an anti-TCR CAR could improve the quality of allogeneic CAR T, in particular decreases the side effects due to the presence of TCR+ T cells, TCR negative cells were prepared as described above (example 1) and different doses were administered into mice for GVHD measurement.

The results show a dose dependent decrease in GVHD symptoms, in particular body weight loss and scratching, when CAR T cells were transfected with mRNA encoding an anti-TCR CAR and there is a clear enrichment in the CAR positive-TCR negative cell population by FACS. This enrichment is dependent on the dose of mRNA transfected and thus the level of anti-TCR CAR transiently expressed on the surface of the CAR T cells.

In human, TALEN®-engineered T cells preparations with less than 3% TCR-positive cells and more than 97% alpha beta TCR negative T cells were found to be less alloreactive than non engineered T cells (Grade 1, GVHD could be measured in reactive patients) and cells prepared according to the present invention were basically fully GVHD-free.

Kinetic Experiments

Kinetic experiments indicated that expression of the anti-CD3 CAR of the invention (SEQ ID NO 8 or 12) could be detected from 3 hours post transfection to up to 5 days (with the highest dose) and up to 7 days when human globin sequences were added to the constructions.

In volunteers, the cells obtained according to the process of the present invention induced no GVHD, regardless of the dose administered (up to $7 \times 10^7$ cells/kg body weight).

One or more illustrative embodiments have been described by way of example. It will be understood to persons skilled in the art that a number of variations and modifications can be made without departing from the scope of the invention as defined in the claims.

Figure 3:
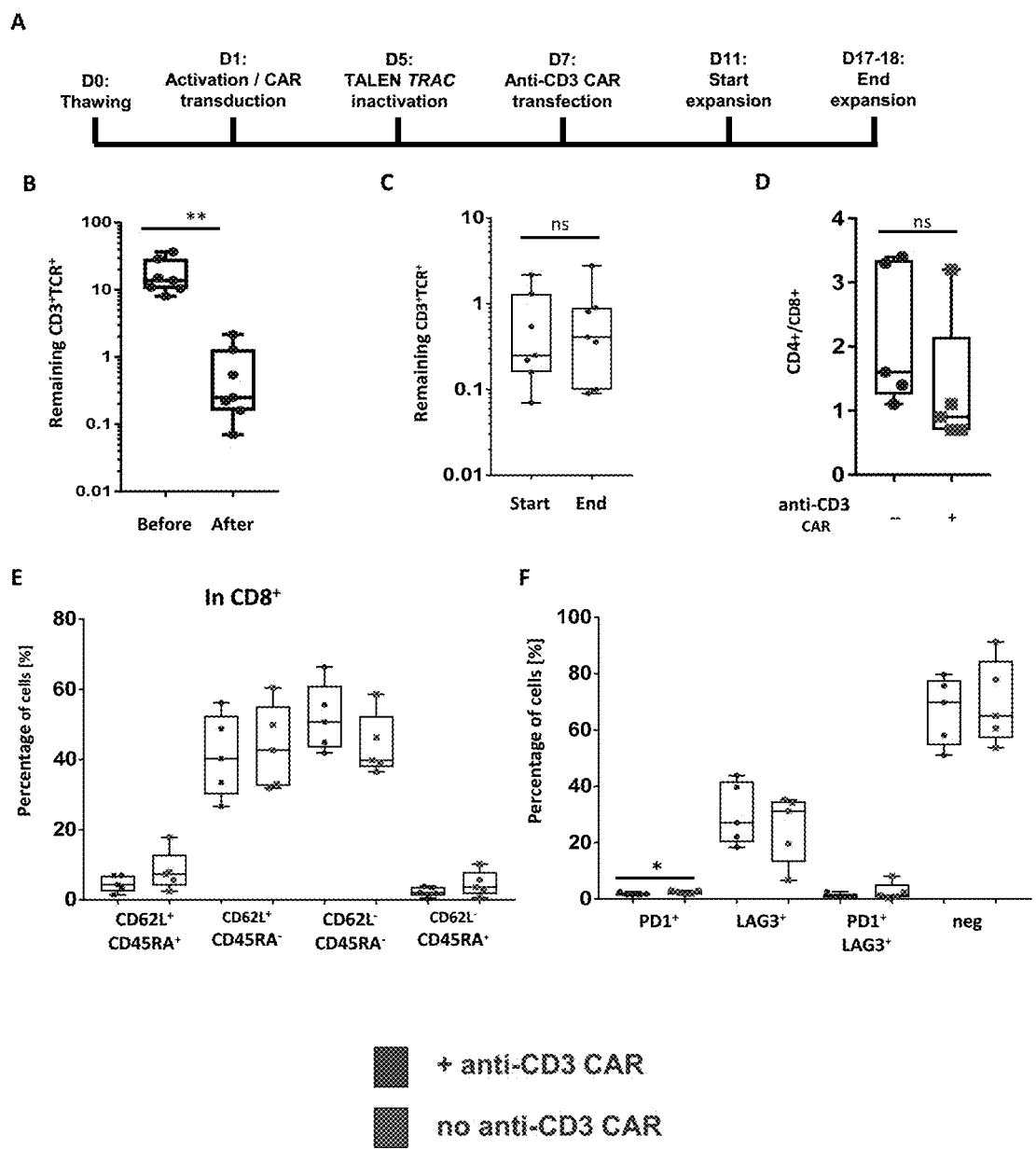
FIG. 3. Shows (A) a schematic representation of CD3+ TCRαβ+ population elimination. (B) Percentage of CD3+ TCRαβ+ cells after consecutive transfections of TRAC TALEN mRNA and anti-CD3 CAR mRNA spaced out by 48h. N=7, 5 independent T-cell donors. (C) Remaining CD3+TCRαβ+ cells at the start and end of the expansion phase. N=7, 5 independent T-cell donors. (D) CD4+/CD8+ ratio of the T-cell population at the endo of the expansion phase, with or without transfection of the anti-CD3 CAR mRNA. N=5, 5 independent T-cell donors. (E) CD62L/ CD45RA expression in the CD8+ population. (F) PD1 and LAG3 expression in the whole T-cell population. N=5, 5 independent T-cell donors. Significance is determined by a standard paired t-test, *=p≤0.05, **=p≤0.01.
Figure 5:
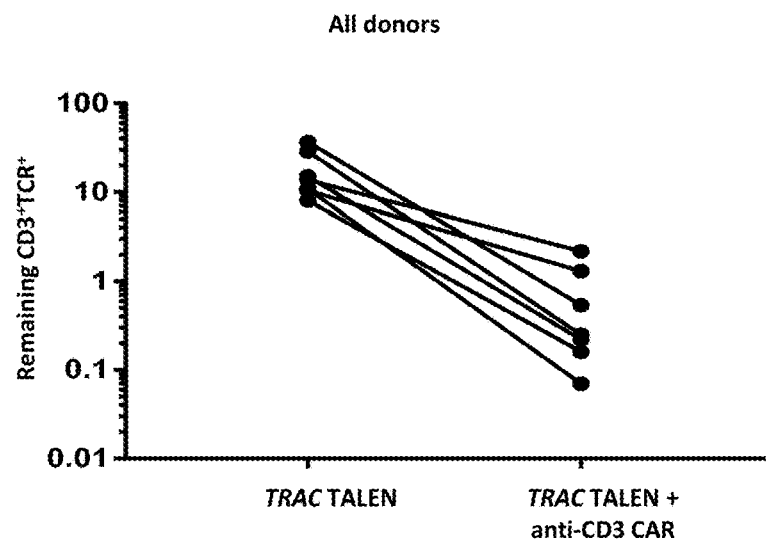
FIG. 5. (A) Represents the percentage of CD3+TCRαβ+ cells after consecutive transfections of TRAC TALEN mRNA and CD3 CAR mRNA (in absence of CD22 CAR) spaced out by 2, 7 and 9 days. (B) the percentage of CD3+TCRαβ+ cells after consecutive transfections of TRAC TALEN mRNA and CD3 CAR mRNA spaced out by 48 h from T-cell donor 1.
Figure 5:
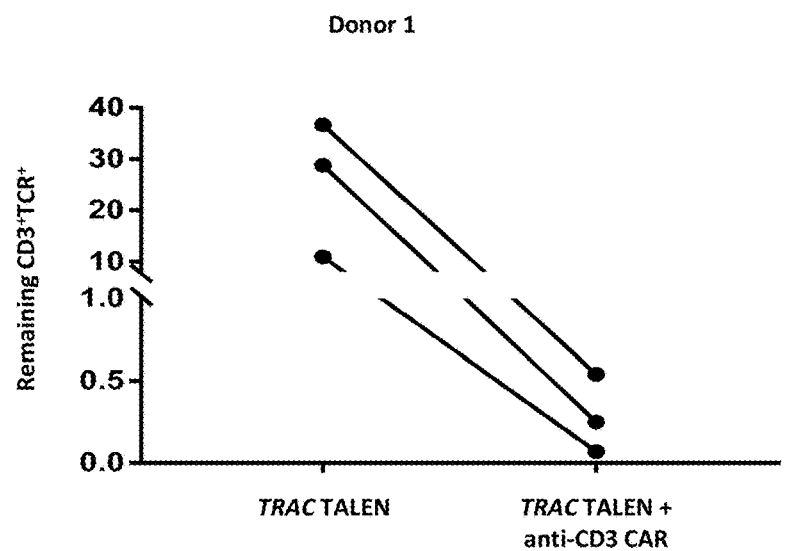

With the goal of developing such a CAR-based TCRαβ+ cell population depletion strategy, we focused first on monitoring the effects of transiently expressing a CD3 CAR (mRNA transfection) following TALEN based TCRαβ inactivation[1]. Independent of the CD3 CAR transfection time point (2, 7 or 9 days post TALEN treatment), we observed a substantial elimination of the remaining CD3+ TCRαβ+ population (starting from 6.5-10.4% of positive cells) down to 0.04-0.93% (median of 0.17%) in the CD3 CAR mRNA treated samples, corresponding to an overall 91-99% depletion efficiency (median of 97.7%, FIG. 5A). The next step was to assess the depletion capacities of transiently expressing CD3 CAR in T-cells stably expressing a CAR targeting a potential tumor antigen (CD22, lentiviral vectorization)[10]. Toward this goal we developed a protocol, starting from frozen PBMCs, to include a lentiviral particle transduction step (CD22 CAR integration) and two mRNA transfection steps. The first mRNA electroporation (TRAC TALEN) being followed 48h later by the CD3 CAR electroporation, a timing allowing to strongly reduce the TCRα/CD3 surface presentation (FIG. 3A). Four days post CD3 CAR electroporation, we observed a minimal residual CD3+ TCRαβ+ population (median CD3+ TCRαβ+: 0.25%, median depletion: 98.5%), indicating that the prior presence of a stably expressed antitumor CAR does not affect the depletion possibilities of the system. These engineered UCAR-T cell populations were then further expanded for 10 to 11 days in presence of IL-2. Post-expansion we did not observe any growth advantage or defect due to the previous CD3 CAR transient expression when considering the CD3+ TCRαβ+ cells (FIG. 3B), with the CD3+ TCRαβ+ population remaining unaffected (p-value: 0.756, FIG. 3C) and minimal (median: 0.41%). Overall, less than 1% of residual TCRαβ T-cells was obtained in four out of five donors tested (FIG. 3C). Furthermore, we also showed that within a given T-cell donor, efficient elimination of CD3+ TCRαβ+ (98.7-99.6% depletion) was obtained, independent of the starting percentage of CD3 positive cells obtained after gene editing (in the range 10-36%, FIG. 5B).

To analyze the impact of the transient expression of the CD3 CAR, we monitored three characteristics of the T-cell populations generated from the 5 individual donors: (i) CD4-to-CD8 ratio, (ii) T-cell differentiation, and (iii) exhaustion markers.

Figure 6:
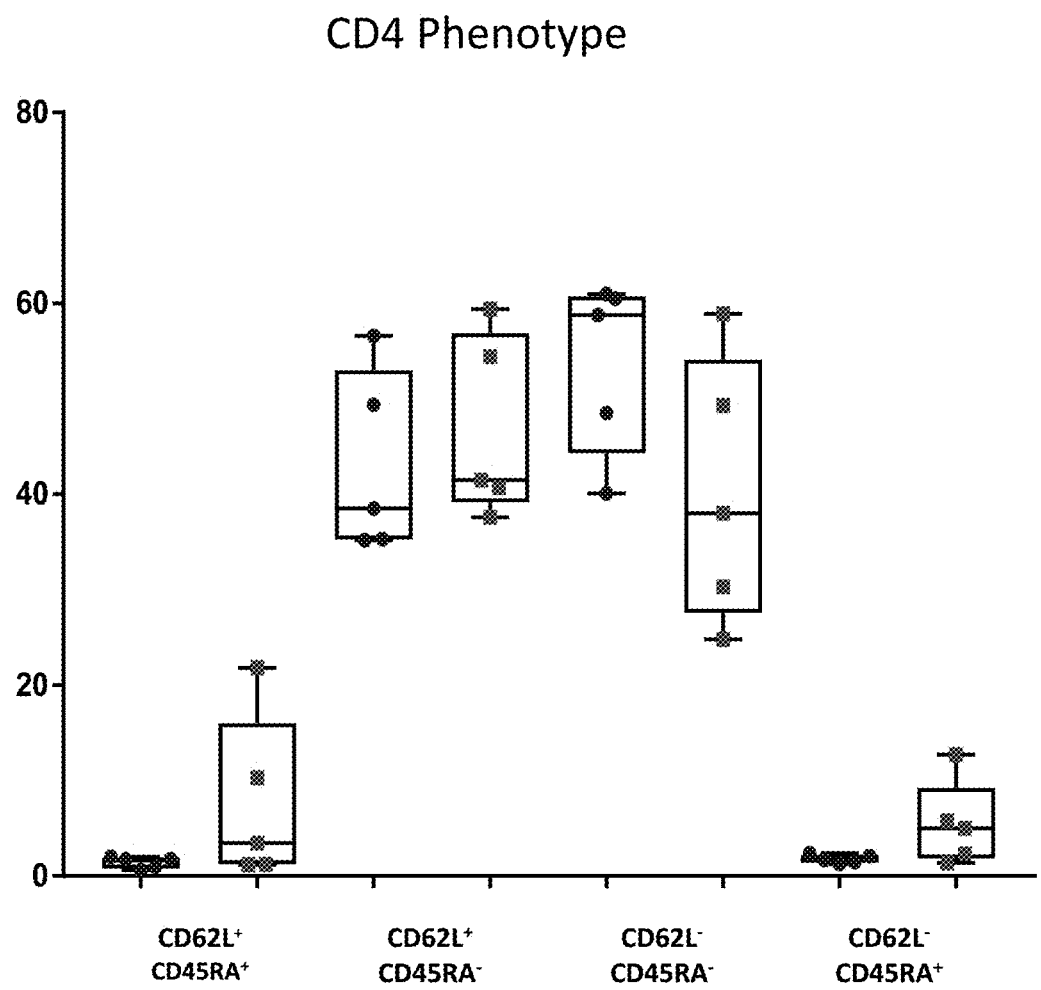
FIG. 6. CD62L/CD45RA expression in the CD4+ population with (red) or without (blue) transfection of the CD3 CAR mRNA. N=5, 5 independent T-cell donors.
Figure 7:
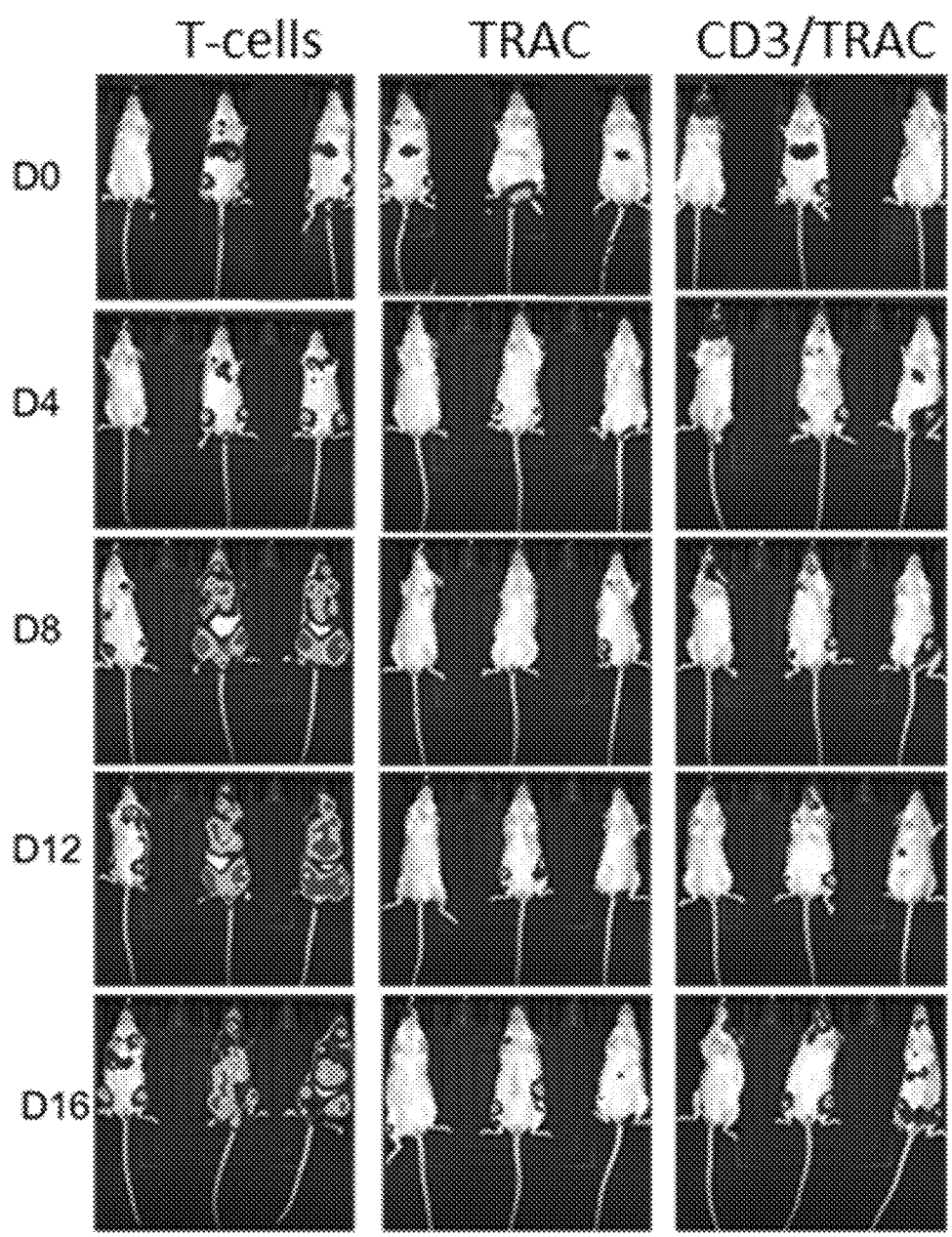
FIG. 7. Tumor burden (bioluminescent signal) of Raji-bearing mice treated with 10×10⁶ UCAR T-cells or UCAR T cells produced with or without CD3 CAR mRNA transfection.

The samples transfected with the CD3 CAR showed a moderate CD8+-biased skewing compared to untransfected samples, maintaining a balanced CD4+ and CD8+ ratio (FIG. 3D). When considering the degree of T-cell differentiation, in particular the proportion of terminal effector cells associated with reduced in vivo anti-tumor functions (CD45RA+ CD62L−)[11, 12], we did not notice any significant impact of the CD3 CAR (FIG. 3E, FIG. 6). In addition, both CD3 CAR transfected or untransfected T-cells contained large proportions of effector memory (CD45RA+CD62L−) and naïve/central memory cells (CD62L+) cells, associated with improved anti-tumor functions (FIG. 3E, FIG. 7). As the acquisition of an exhausted phenotype has also been previously associated with reduced in vivo functions, we monitored the surface expression of PD1 and LAG3, two well documented exhaustion markers[13]. Unexpectedly, we observed low frequencies of PD1, LAG3, or PD1/LAG3 co-expressing cells in the CD3 CAR treated samples (FIG. 3F), without substantial upregulation when compared to the untreated samples.

Figure 4:
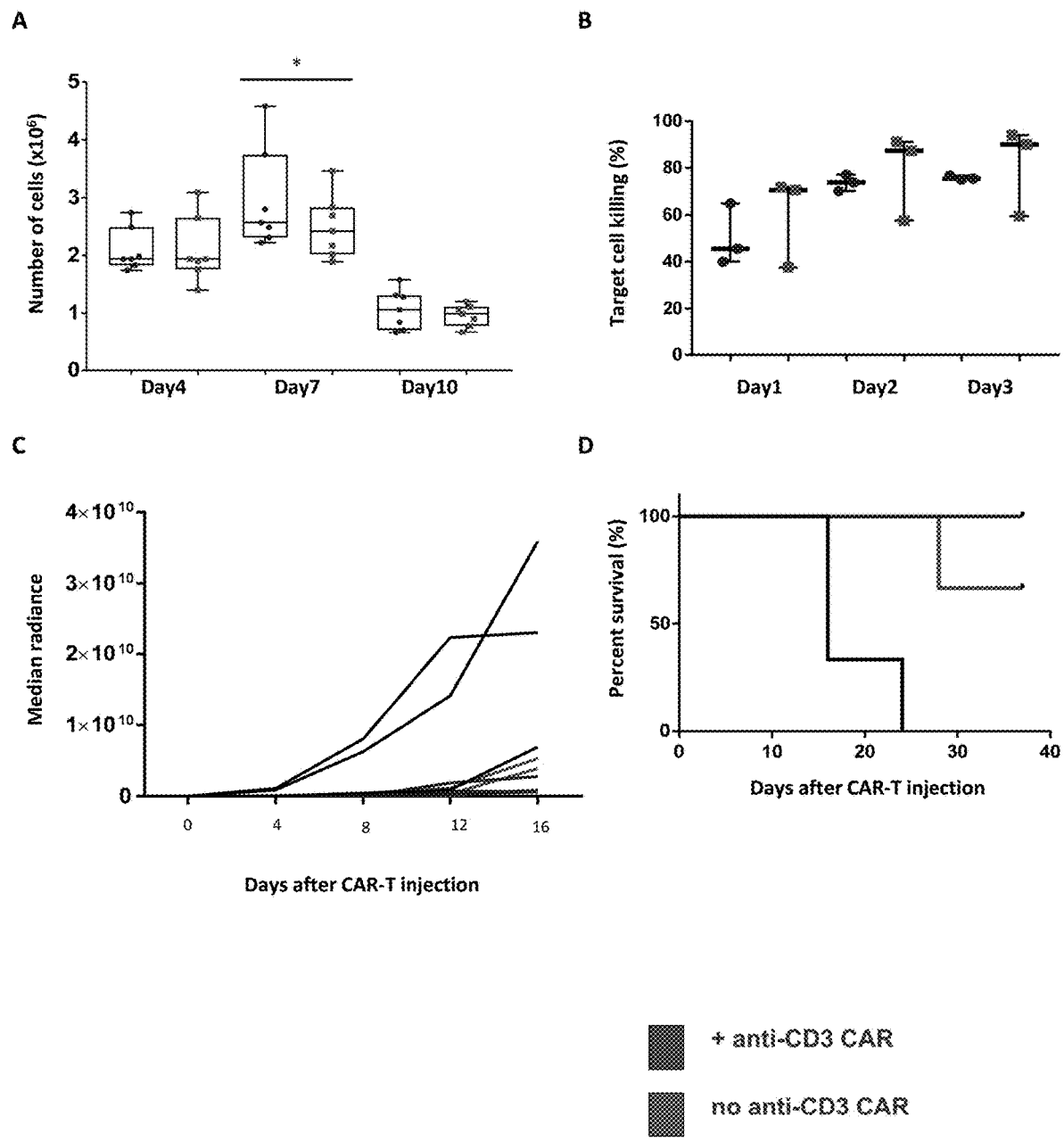
FIG. 4. Describes: (A) Antigen dependent proliferation, over a 10 day period, of CAR T-cells with or without transfection of the anti-CD3 CAR mRNA. N=7, 5 independent T-cell donors (B) Target cell killing over a period of 3 days. N=3. 3 independent T-cell donors. (C) Tumor burden (average radiance) of Raji-bearing mice treated with 5×10⁵ CAR T cells (produced with or without anti-CD3 CAR mRNA transfection). (D) Kaplan-Meier analysis of the mice survival. CAR T-cell from 1 donor. 3 mice per group. Significance is determined by a standard paired t-test, *=p≤0.05, **=p≤0.01.

Finally, we further closely assessed the fitness and function of the engineered CAR T-cells in vitro and in vivo. We first monitored the T-cell proliferation over a period of 10 days in response to a single stimulation with target cells expressing the appropriate antigen (CD22+, Raji) in the absence of IL2. This experimental setup did not reveal marked differences in the antigen dependent proliferative capacity of the T-cells treated or not with the CD3 CAR (FIG. 4A). Using engineered CAR T-cells from three donors, we performed an in vitro three days killing assay where the UCAR-T cells were challenged with target cells both days (luciferase expressing Raji cells). We found that for each donor, both samples, T-cell transfected with the CD3 CAR or not, were able to efficiently promote target cell killing to similar levels, as monitored by decrease of the target cell luciferase signal (FIG. 4B). As the in vitro functional studies did not reveal any marked and significant (p-values: 0.49 for day 1, 0.64 for day 2 and 0.67 for day 3) differences, we lastly investigated the functional properties of the engineered CAR T-cells in vivo using a human CD22+ lymphoma xenograft model (luciferase expressing Raji cells injected into mice). In this model, both engineered CAR T-cells (+/−CD3 CAR treatment) induced substantially delayed tumor progression and prolonged survival relative to control CAR (FIGS. 4C and 4D, FIG. 7). These findings being supported by a recent report by Qasim and colleagues[4], that demonstrates the feasibility to stably express a CD3-specific CAR in T-cells in an allogeneic setup against acute lymphoblastic leukemia (T-ALL), without affecting the fitness of the engineered cells.

In summary, we propose a novel methodology, broadly implementable, to eliminate residual TCRαβ+ cells at an early stage of the allogeneic CAR T-cell generation process to minimize, or prevent, risk of graft-versus-host-disease (GvHD). This straightforward, easy to implement, purification approach could reduce yield losses that results from mechanical purification and simplify cell handling prior to freezing of the final product. In addition to the generation of allogeneic "off-the-shelf" CAR T-cells for adoptive immunotherapies, we further envision the transient targeting of other specific surface antigens as an approach that can be extended to eliminate any minor population present within the starting material.

Methods

T-Cell Proliferation

T-cells were cultured in X-Vivo™ 15 (Lonza) supplemented with 5% human serum hAB (Gemini) and 20 ng/ml IL-2 (Miltenyi) at a density of $1 \times 10^6$ cells/ml.

mRNA Production mRNA was produced with EPAP-mediated polyadenylation using the mMessage mMachine™ T7 Ultra kit (Thermo fisher scientific) from a PCR product encoding the CD3 CAR or without EPAP-mediated polyadenylation or from a linearized plasmid DNA template, encoding the CD3 CAR, a mouse hba 3'UTR and a 120-nucleotide-long polyA.

Lentiviral Particle Production

Lentiviral particles were generated in 293 FT cells (ThermoFisher) cultured in RPMI 1640 Medium (ThermoFisher) supplemented with 10% FBS (Gibco), 1% HEPES (Gibco), 1% L-Glutamine (Gibco) and 1% Penicillin/Streptomycin (Gibco) using Opti-MEM™ medium (Gibco) and Lipofectamine™ 2000 (ThermoFisher) according to standard transfection procedures. 48 and/or 72 hours post transfection the supernatants were recovered and concentrated by ultracentrifugation.

T-Cell Transduction

Cryopreserved human PBMCs (ALLCELLS) were thawed and plated at $1 \times 10^6$ cells/ml in X-Vivo™ 15 media (Lonza) supplemented with 5% hAB serum (Gemini) or CTS™ Immune Cell SR (ThermoFisher) and 20 ng/ml IL-2 (Miltenyi Biotech) for overnight culture at 37° C. The next day, the PBMCs were activated using human T activator CD3/CD28 (Life Technology) in serum-free X-Vivo™ 15 media without IL-2. One million activated PBMCs (in 600 µl) were immediately incubated without removing the beads in an untreated 12-well plate pre-coated with 30 µg/ml RetroNectin® (Takara) in the presence of lentiviral particles encoding the CD22 targeting CAR for 2 h at 37° C. Six hundred microliters of 2× X-Vivo™ 15 media (X-Vivo™ 15, 10% hAB serum and 40 ng/ml IL-2) was added after 2 to 3 hours, and the cells were incubated at 37° C. for 72 h.

T-Cell Transfection

Four days following activation/transduction, human T lymphocytes were transfected by electrotransfer using an AgilePulse MAX™ system (Harvard Apparatus): cells were pelleted and resuspended in cytoporation medium T. $5 \times 10^6$ cells were mixed with 5 µg total TRAC TALEN mRNA (2.5 ug each of the left and right TALEN arms) into a 0.4 cm cuvette. Separate aliquots of TRAC TALEN or mock-transfected cells were again electroporated at different time points (days 2, 7, or 9 post TRAC TALEN transfection) with 20 ug of CD3 CAR mRNA. Engineered T-cells were then kept in culture up to 4 days before expansion for 6-7 days in G-Rex10 (Wilson Wolf) in 40 ml of complete X-Vivo™ 15 media.

Marker Surface Detection

The proportion of T-cells expressing the CAR at their surface was then quantified using the following antibodies: CD3: Clone BW264/56, Vioblue (Miltenyi #130-094-363), TCRαβ: Clone REA652, PE (Miltenyi #130-109-920), CD4: Clone VIT4, PEVio770 (Miltenyi #130-096-552), CD8: Clone SK1, BV510 (Biolegend #344732), CD62L: Clone 145/15, APC (Miltenyi #130-113-617), CD45RA: Clone T6D11, Vioblue (Miltenyi #130-113-360), PD1: Clone REA1165, PE (Miltenyi #130-120-388) and LAG3: Clone 11C3C65, BV421 (Biolegend #369313).

Antigen Dependent Proliferation

Raji cells were treated with 20 Gy using a CellRad X-ray irradiation system (Faxitron, Tucson, AZ, USA), washed twice, counted and 500,000 were plated with 500,000 T-cells (1:1) in duplicate into 1 ml final volume of X-Vivo™ 15 media with 5% hAB serum, but lacking IL-2, in a 24 well plate. At days 4 and 7, the cells were counted on the Vicell and passaged at 500,000 cells/0.5 ml media into a 48 well plate. At day 10, the cells were mixed and counted for the last time point.

Assessment of CAR Cytotoxicity

Transduced T-cells ($1.5 \times 10^6$ cells) were incubated in X-Vivo™ 15 media with 5% hAB serum, lacking IL-2 in a 3:1 (T-cells: Targets) ratio with target cells (Raji) presenting the CAR target antigen and expressing a luciferase ($0.5 \times 10^6$ cells) in a 12-well plate. After 24 h, the cells were collected and mixed, and 100 ul of cells was used for luciferase quantification (OneGlo™, Promega). The remainder of the cells were pelleted and resuspended in fresh X-vivo 15 media with 5% hAB serum, no IL-2, and an additional $0.5 \times 10^6$ target cells were added. This step was repeated for 2 consecutive days.

In Vivo Experiment Using NGS Xenograft Model (FIG. 7)

All procedures involving animals were performed in accordance with regulations and established guidelines and were reviewed and approved by the Cellectis Institutional Animal Care and Use Committee (IACUC).

NSG mice were injected with 0.25 $10^6$ CD22+ Raji target cells. The tumor cells were allowed to expand until mouse randomization, which was performed at day 4 based bioluminescence imaging (BLI) (XenoLight™ D-luciferin (PerkinElmer). The next day, mice were adoptively transferred (i.v.) with either $10 \times 10^6$ viable mock or CAR transduced T-cell treated or not with the CD3 CAR (3 mice per group). The mice were then re-imaged at Day 4, 8, 12 and 16.

REFERENCES

1. Poirot, L. et al. Multiplex Genome-Edited T-cell Manufacturing Platform for "Off-the-Shelf" Adoptive T-cell Immunotherapies. *Cancer Res* 75, 3853-3864 (2015).

2. Qasim, W. et al. Molecular remission of infant B-ALL after infusion of universal TALEN gene-edited CAR T cells. *Sci Transl Med* 9 (2017).
3. Valton, J. et al. A Multidrug-resistant Engineered CAR T Cell for Allogeneic Combination Immunotherapy. *Mol Ther* 23, 1507-1518 (2015).
4. Rasaiyaah, J., Georgiadis, C., Preece, R., Mock, U. & Qasim, W. TCRalphabeta/CD3 disruption enables CD3-specific antileukemic T cell immunotherapy. *JCI Insight* 3 (2018).
5. Provasi, E. et al. Editing T cell specificity towards leukemia by zinc finger nucleases and lentiviral gene transfer. *Nat Med* 18, 807-815 (2012).
6. Macleod, D. T. et al. Integration of a CD19 CAR into the TCR Alpha Chain Locus Streamlines Production of Allogeneic Gene-Edited CAR T Cells. *Mol Ther* 25, 949-961 (2017).
7. Hale, M. et al. Homology-Directed Recombination for Enhanced Engineering of Chimeric Antigen Receptor T Cells. *Mol Ther Methods Clin Dev* 4, 192-203 (2017).
8. Eyquem, J. et al. Targeting a CAR to the TRAC locus with CRISPR/Cas9 enhances tumour rejection. *Nature* 543, 113-117 (2017).
9. Georgiadis, C. et al. Long Terminal Repeat CRISPR-CAR-Coupled "Universal" T Cells Mediate Potent Anti-leukemic Effects. *Mol Ther* 26, 1215-1227 (2018).
10. Xiao, X., Ho, M., Zhu, Z., Pastan, I. & Dimitrov, D. S. Identification and characterization of fully human anti-CD22 monoclonal antibodies. *MAbs* 1, 297-303 (2009).
11. Gattinoni, L. et al. A human memory T cell subset with stem cell-like properties. *Nat Med* 17, 1290-1297 (2011).
12. Sommermeyer, D. et al. Chimeric antigen receptor-modified T cells derived from defined CD8+ and CD4+ subsets confer superior antitumor reactivity in vivo. *Leukemia* 30, 492-500 (2016).
13. Blackburn, S. D. et al. Coregulation of CD8+ T cell exhaustion by multiple inhibitory receptors during chronic viral infection. *Nat Immunol* 10, 29-37 (2009).

---

The invention claimed is:

1. A method for enriching for T Cell Receptor (TCR)-negative chimeric antigen receptor (CAR)-T cells during manufacturing of engineered CAR-T cells, the method comprising:
   a first disruption step comprising inactivating at least one gene encoding an endogenous TCR component in T cells from a donor by introducing into the T cells at least one mRNA encoding a rare cutting endonuclease specific for the at least one gene encoding the endogenous TCR component, wherein the rare cutting endonuclease is a TAL-effector protein or a CRISPR CAS9;
   a first transformation step comprising modifying the T cells by introducing at least one exogenous polynucleotide encoding a recombinant CAR into the genome of the T cells, wherein the first transformation step is performed before, after, or concomitantly with the first disruption step;
   followed by:
   a second transformation step comprising transiently expressing an anti-TCR complex CAR by introducing into the T cells a synthetic mRNA encoding the anti-TCR complex CAR;
   thereby producing a population of engineered CAR-T cells enriched for TCR-negative CAR-T cells.

2. The method of claim 1, wherein the anti-TCR complex CAR:
   is specific for an epitope of a TCR;
   is specific for an epitope of a TCR-associated protein;
   is specific for an epitope of a CD3 subunit;
   is specific for an epitope of a TCR subunit;
   is specific for a combination of TCR subunits;
   is specific for an epitope of a TCR alpha subunit;
   is specific for an epitope of a TCR beta 1 or TCR beta 2 subunit; or
   is specific for a (common) epitope of a TCR alpha beta subunit.

3. The method of claim 1, wherein the synthetic mRNA encoding the anti-TCR complex CAR comprises SEQ ID NO: 2, or a succession of the following sequences: SEQ ID NO: 1, SEQ ID NO: 2, SEQ ID NO: 3, SEQ ID NO: 4, and SEQ ID NO: 5.

4. The method of claim 1, wherein the first transformation step comprises, using an AAV6 viral vector to introduce the exogenous polynucleotide encoding the CAR.

5. The method of claim 1, further comprising a second disruption step comprising inactivating at least one gene selected from the group consisting of a beta 2 microglobulin gene, a gene conferring sensitivity or resistance to a drug, and a cytokine gene, by introducing into the cells at least one mRNA encoding the rare cutting endonuclease specific for the at least one gene.

6. The method of claim 1, wherein the T cells in the first disruption step comprise at least one of inflammatory T-lymphocytes, cytotoxic T-lymphocytes, regulatory T-lymphocytes, helper T-lymphocytes, and NK T cells.

7. The method of claim 1, wherein the CAR of the first transformation step is specific for a cell surface antigen target selected from the group consisting of: ROR1, EGFRVIII, BCMA, CD33, GD3, CD19, CD38, HSP70, CD30, FAP, HER2, CD79a, CD79b, CD123, CD22, CLL-1, MUC-1, GD2, O acetyl GD2, and CS1.

8. The method of claim 1, wherein said method further comprises:
   a step of inactivating at least one gene involved in alloreactivity selected from the group consisting of: beta2M, regulatory factor X-associated ankyrin-containing protein (RFXANK), regulatory factor 5 (RFX5), regulatory factor X-associated protein (RFXAP), class II transactivator (CIITA), and TAP-1, or a combination thereof, by introducing into the cells at least one mRNA encoding the rare cutting endonuclease specific for the at least one gene; and/or
   an additional disruption step of inactivating at least one gene selected from the group consisting of: PDL1, Programmed Death 1 (PD-1), Cytotoxic T-Lymphocyte Antigen 4 (CTLA-4), LAG3, Tim3, BTLA, BY55, TIGIT, B7H5, LAIR1, SIGLEC10, and 2B4, or a combination thereof; and/or
   a step of inactivating at least one gene involved in drug resistance selected from the group consisting of: deoxycytidine kinase (dCk), hypoxanthine guanine phosphoribosyl transferase (HPRT), glucocorticoid receptor (GR), and CD52, or a combination thereof, by introducing in the cells at least one mRNA encoding the rare cutting endonuclease specific for the at least one gene; and/or
   a step of inactivating at least one gene involved in drug hypersensitivity selected from the group consisting of: GGH, RhoA, CDK5, CXCR3, NR1H2, URG4, PARP14, AMPD3, CCDC38, NFU1 and CACNG5, or a combination thereof, by introducing in the cells at least one mRNA encoding a rare cutting endonuclease specific for the at least one gene.

9. A population of engineered CAR-T cells comprising TCR-negative CAR-T cells and cells transiently expressing an anti-TCR complex CAR obtained using the method of claim 1.

10. A population of engineered CAR-T cells obtained using the method of claim 1, wherein the population of cells comprises TCR-negative CAR-T cells and comprises less than 0.03% alpha beta TCR-positive cells.

11. A pharmaceutical composition comprising the population of cells comprising the TCR-negative CAR-T cells of claim 10, and a pharmaceutically acceptable vehicle.

12. The method of claim 1, wherein the population of cells enriched for TCR-negative CAR-T cells comprises 5% or less of alpha-beta-TCR-positive cells.

* * * * *